(12) United States Patent
Prakash et al.

(10) Patent No.: US 12,281,139 B2
(45) Date of Patent: *Apr. 22, 2025

(54) MOGROSIDES, METHODS OF OBTAINING THE SAME, AND USES

(71) Applicant: The Coca-Cola Company, Atlanta, GA (US)

(72) Inventors: Indra Prakash, Alpharetta, GA (US); Ma Gil, Atlanta, GA (US); Christopher Mercogliano, Atlanta, GA (US)

(73) Assignee: The Coca-Cola Company, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/049,646

(22) PCT Filed: Apr. 23, 2019

(86) PCT No.: PCT/US2019/028681
§ 371 (c)(1),
(2) Date: Oct. 22, 2020

(87) PCT Pub. No.: WO2019/209803
PCT Pub. Date: Oct. 31, 2019

(65) Prior Publication Data
US 2024/0270785 A1     Aug. 15, 2024

Related U.S. Application Data

(60) Provisional application No. 62/661,422, filed on Apr. 23, 2018.

(51) Int. Cl.
| | | |
|---|---|---|
| C07J 17/00 | (2006.01) |
| A23L 2/60 | (2006.01) |
| A23L 27/30 | (2016.01) |

(52) U.S. Cl.
CPC ............... *C07J 17/005* (2013.01); *A23L 2/60* (2013.01); *A23L 27/36* (2016.08)

(58) Field of Classification Search
None
See application file for complete search history.

(56) References Cited

FOREIGN PATENT DOCUMENTS

| | | |
|---|---|---|
| JP | 2003252895 | 9/2008 |
| WO | WO 2009023975 | 2/2009 |
| WO | WO 2015082012 | 6/2015 |
| WO | WO 2017075257 | 5/2017 |
| WO | WO 2017113649 | 7/2017 |

OTHER PUBLICATIONS

Li, F., Yang, F., Liu, X., Wang, L., Chen, B., Li, L., & Wang, M. (2017). Cucurbitane glycosides from the fruit of Siraitia grosvenori and their effects on glucose uptake in human HepG2 cells in vitro. Food chemistry, 228, 567-573. (Year: 2017).*
Niu, B., Ke, C. Q., Li, B. H., Li, Y., Yi, Y., Luo, Y., . . . & Ye, Y. (2017). Cucurbitane glucosides from the crude extract of Siraitia grosvenorii with moderate effects on PGC-1a promoter activity. Journal of Natural Products, 80(5), 1428-1435. (Year: 2017).*
Niu, B. et al., "Cucurbitane glucosides from the crude extract of Siraitia grosvenorii with moderate effects on PGC-la promoter activity", Journal of Natural Products, 2017, vol. 80, pp. 1428-1435.
International Search Report for PCT/US2019/028681, issued Sep. 4, 2019.

* cited by examiner

*Primary Examiner* — Dale R Miller
(74) *Attorney, Agent, or Firm* — King & Spalding

(57) ABSTRACT

Novel mogrosides and compositions comprising said novel mogrosides, including consumables, are provided herein. Methods of obtaining said novel mogrosides from either purification and/or bioconversion, are also provided.

20 Claims, 9 Drawing Sheets

MOGROSIDES, METHODS OF OBTAINING THE SAME, AND USES

CROSS REFERENCE TO RELATED APPLICATIONS

This application is a national phase application under 35 U.S.C. § 371 of International Application No. PCT/US2019/028681, filed Apr. 23, 2019, which claims priority to U.S. Provisional Application No. 62/661,422, filed Apr. 23, 2018. The contents of each of the above-identified applications is hereby fully incorporated herein by reference.

FIELD OF THE INVENTION

The present invention relates generally to novel mogrosides, as well as compositions comprising such novel mogrosides, including consumables. The present invention further extends to methods of obtaining the novel mogrosides by bioconversion and/or purification from, e.g. Luo Han Guo extract.

BACKGROUND OF THE INVENTION

Natural caloric sugars, such as sucrose, fructose and glucose, are utilized to provide a pleasant taste to beverages, foods, pharmaceuticals, and oral hygienic/cosmetic products. Sucrose, in particular, imparts a taste preferred by consumers. Although sucrose provides superior sweetness characteristics, it is disadvantageously caloric.

Non-caloric or low caloric sweeteners have been introduced to satisfy consumer demand. However, non- and low caloric sweeteners taste different from natural caloric sugars in ways that frustrate consumers. On a taste basis, non-caloric or low caloric sweeteners exhibit a temporal profile, maximal response, flavor profile, mouth feel, and/or adaptation behavior that differ from sugar. Specifically, non-caloric or low caloric sweeteners exhibit delayed sweetness onset, lingering sweet aftertaste, bitter taste, metallic taste, astringent taste, cooling taste and/or licorice-like taste. On a source basis, many non-caloric or low caloric sweeteners are synthetic sweeteners. Consumer desire for natural non-caloric or low caloric sweeteners that tastes like sucrose remains high.

Luo Han Guo is the common name for the sweet extract made from the fruit of Siraitia grosvenorii, a herbaceous perennial vine of the Cucurbitaceae family native to Southern China and Northern Thailand. Luo Han Guo extracts are nearly 250 times sweeter than sugar and are desirable as both non-caloric and natural in origin.

The sweetness of Luo Han Guo extract is generally attributed to mogrosides present at the level of about 1% by weight in the fleshy part of the fruit. Both the fresh and dried fruits are extracted to yield a powder that is 80% or more mogrosides. Yet, some mogrosides, such as mogroside III and mogroside IIE, can be tasteless or even bitter. Luo Han Guo extracts may also contain multiple impurities which possess undesirable organoleptic properties, which can affect the color, smell and taste profile of Luo Han Guo extract.

There remains a need for natural, non-caloric sweeteners. There remains a further need for methods for preparing and purifying mogrosides from Luo Han Guo extract.

SUMMARY OF THE INVENTION

In one aspect, novel derivatives of Mogroside V, Mogroside IIIE and Mogroside IV are provided. Mogroside V derivatives of the present invention belong to Formula I, Formula II or Formula III, described hereinbelow. Mogroside IIIE derivatives of the present invention belong to Formula IV and Formula V, described hereinbelow. Mogroside IV derivatives of the present invention belong to Formula VII and Formula VIII described hereinbelow. In a further aspect, the present invention is a composition comprising at least one mogroside of the present invention described herein. In a particular embodiment, the present invention is a composition comprising at least one isolated and purified mogroside described herein.

In one embodiment, the present invention is a sweetener composition comprising at least one mogroside of the present invention described herein. In a particular embodiment, the present invention is a sweetener composition comprising at least one isolated and purified mogroside of the present invention described herein.

In yet another embodiment, the present invention is a consumable comprising at least one mogroside of the present invention described herein. Suitable consumables include, but are not limited to, liquid-based or dry consumables, such as, for example, pharmaceutical compositions, edible gel mixes and compositions, dental compositions, foodstuffs, beverages and beverage products.

In another aspect, the present invention is a method of preparing a mogroside of the present invention (also referred to as a "target mogroside") comprising contacting a medium comprising a starting mogroside selected from Mogroside IV, Mogroside V and Mogroside IIIE with a biocatalyst, thereby producing a composition comprising the target mogroside.

The medium can further comprise, e.g. co-substrates for the biocatalyst to act as a glucose source. Exemplary co-substrates include, but are not limited to, sucrose, glucose-1-fluoride, dextrin, soluble starch and UDP-glucose.

The biocatalyst can be a purified enzyme, a crude lysate or a whole cell suspension. Alternatively, the biocatalyst can be provided in the form of cells or microorganism.

The identity of the starting mogroside and the biocatalyst determines the identity of the target mogroside.

The target mogroside can be separated from the medium to provide a separated target mogroside composition, which can optionally be subsequently purified, to provide a purified target mogroside composition comprising at least about 80% by weight of the target mogroside. Purification can be affected by any means known to one of skill in the art including, but not limited to, crystallization, separation by membranes, centrifugation, extraction (liquid or solid phase), chromatographic separation, HPLC (preparative or analytical) or a combination of such methods.

The present invention also provides methods of purifying a mogroside of the present invention comprising (i) passing a solution comprising a source material comprising a mogroside of the present invention through a HPLC column and (ii) eluting fractions comprising a mogroside of the present invention to provide a purified mogroside composition comprising a mogroside of the present invention in at least about 80% by weight. Exemplary source materials include, but are not limited to, mixtures of mogrosides, Luo Han Guo extract (commercial or prepared), and compositions resulting from the bioconversion processes described herein.

DETAILED DESCRIPTION OF THE INVENTION

Figure 1:
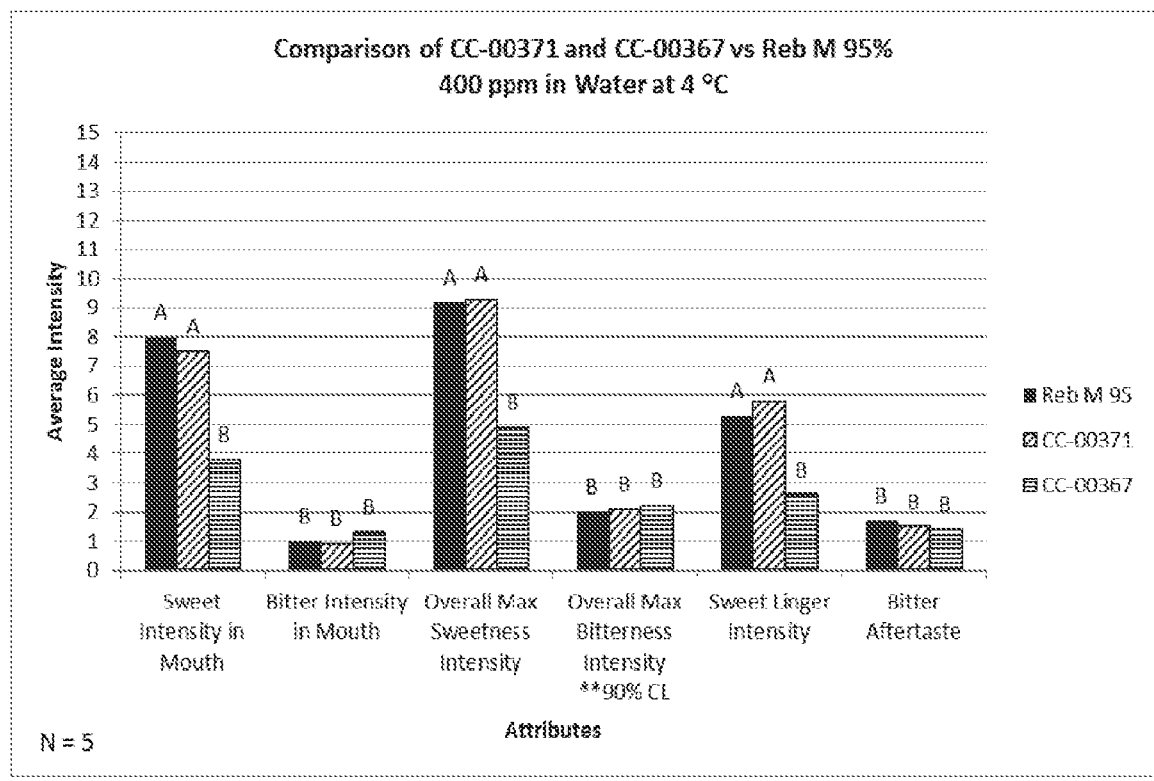
FIG. 1: Taste attribute comparison of CC-00371 and CC-00367 compared to Reb M 95% (all at 400 ppm) in water at 4° C.

The present invention relates generally to novel mogrosides, in particular derivatives of mogroside V, mogroside IIIE, and mogroside IV, that are useful as sweeteners.

The present invention further extends to methods of obtaining the novel mogrosides described herein, either by purification from Luo Han Guo extracts or by bioconversion from other mogrosides.

The present invention also relates to compositions (including consumables) comprising the novel mogrosides, as well as methods for enhancing the sweetness of consumables using these novel mogroside and compositions.

I. Compounds

In one aspect, the present invention provides novel mogroside compounds.

Mogroside V has the following structure:

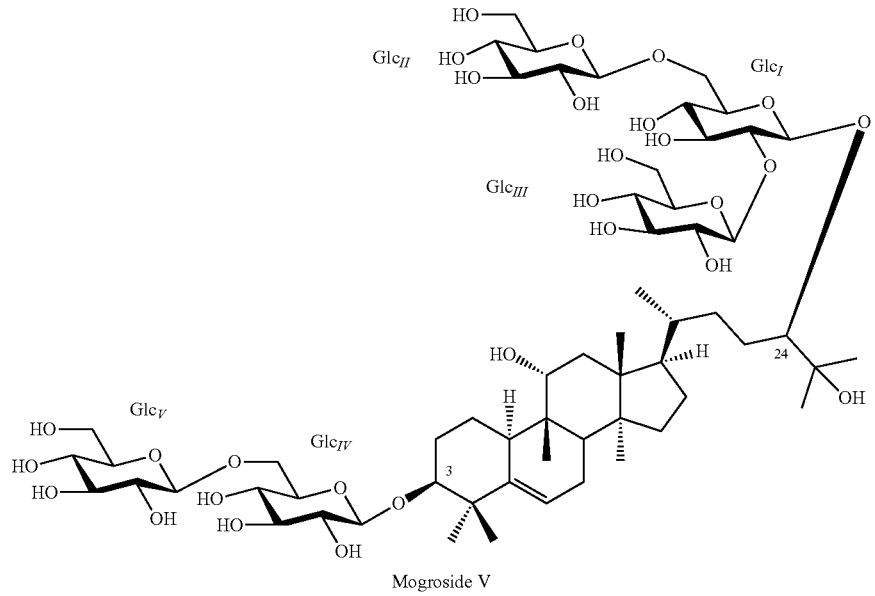

Mogroside V

Mogroside V contains five glucose units pendant to the mogrol core. All of the linkages between the core and the glucose substituents at C24 and C3 as well as linkages between glucose units are β-linkages. There are β1→6 linkages between (i) GlcI and GlcII and (ii) GlcIV and GlcV. There is a β1→2 linkage between GlcI and GlcIII.

Novel compounds of the present invention that are derivatives of Mogroside V also contain GlcI-IV in the same configuration as Mogroside V, with additional glucose substituents on either GlcII, GlcIII or GlcV.

The present invention provides novel mogrosides of Formula I:

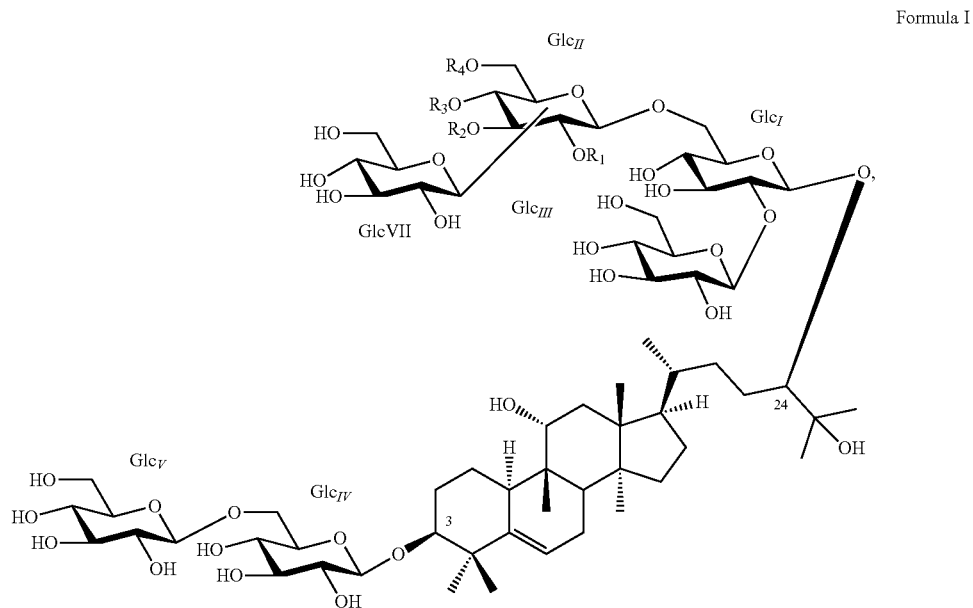

Formula I wherein GlcII and GlcVII are bonded at one of the $R_1$, $R_2$, $R_3$ or $R_4$ positions, and the other positions are hydrogen.

The bond between GlcII and GlcVII can be an α- or β-linkage. More particularly, the bonds can be selected from β-(1,2)-linkages, β-(1,3)-linkages, ρ-(1,4)-linkages, ρ-(1,6)-linkages, α-(1,2)-linkages, α-(1,3)-linkages, α-(1,4)-linkages, α-(1,6)-linkages.

In a particular embodiment, the mogroside of Formula I is selected from the following:

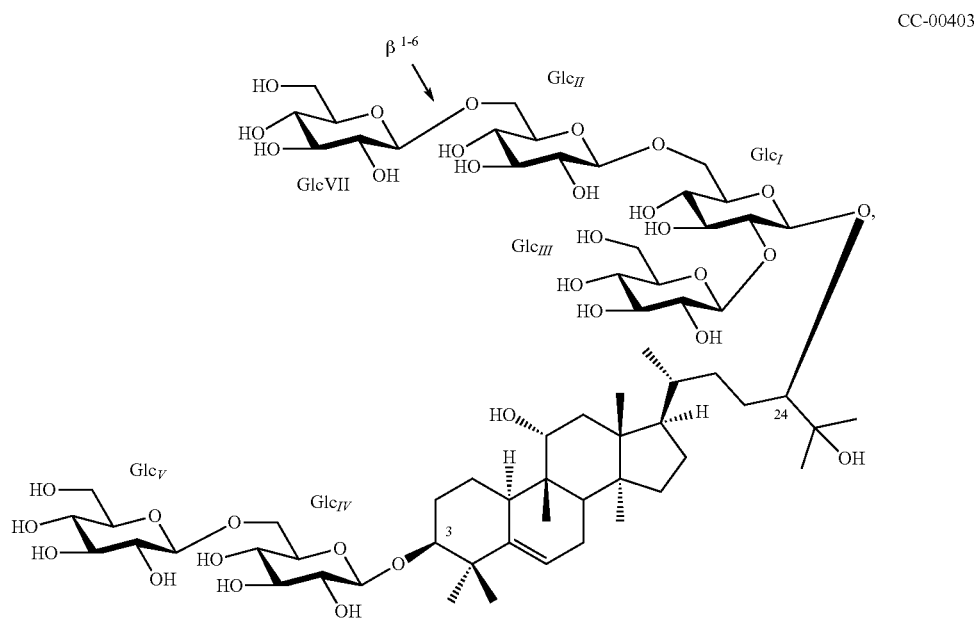

-continued
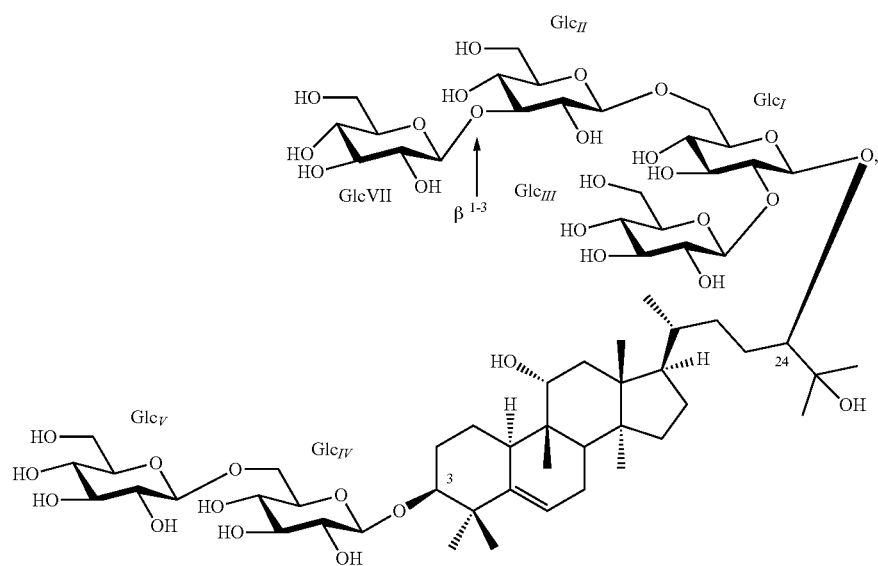
CC-00371
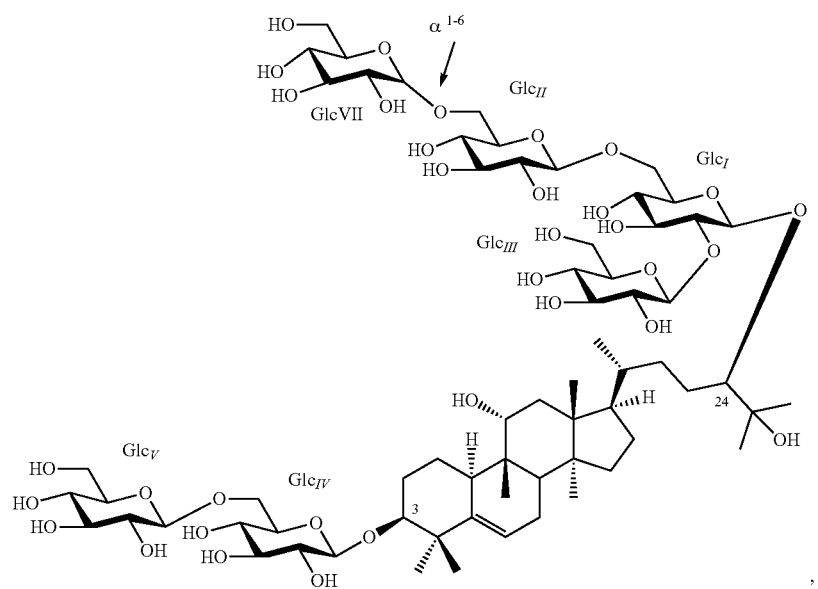
CC-00417
, and

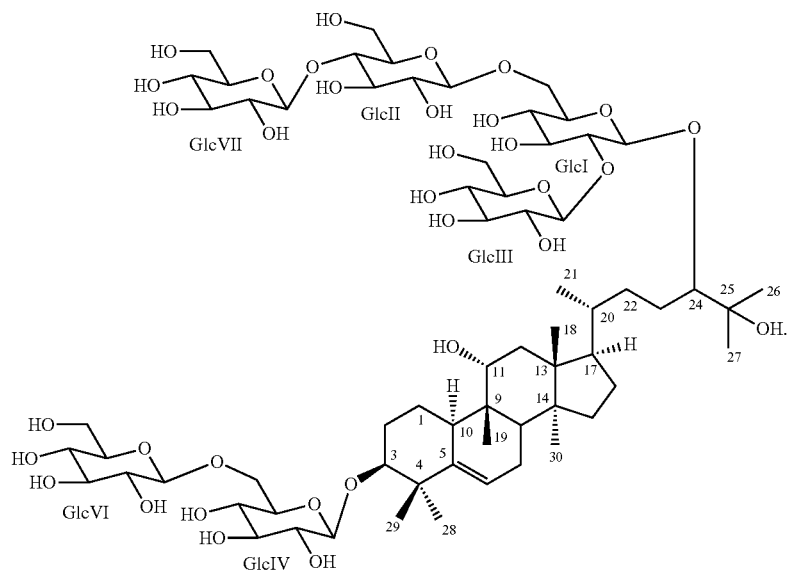

The present invention also provides novel mogrosides of Formula II:

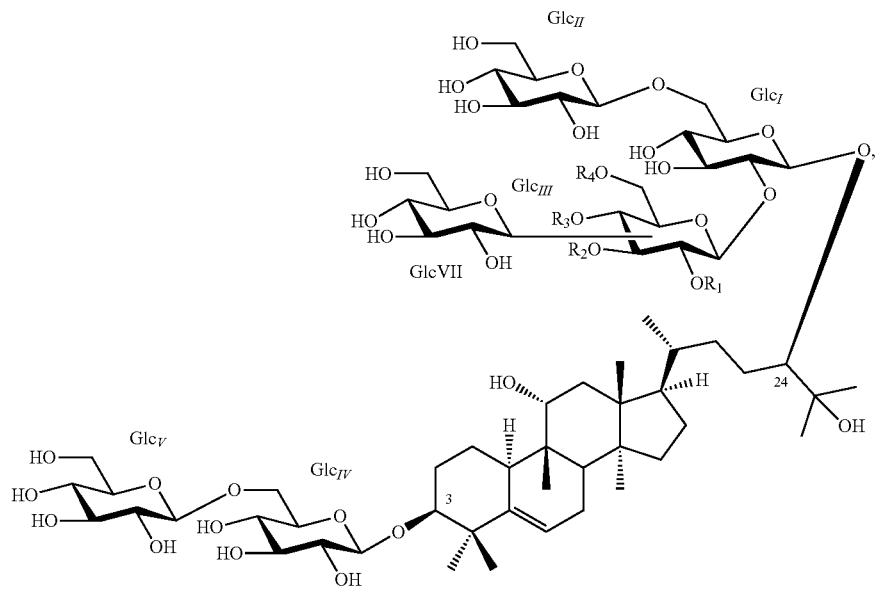

Formula II wherein GlcIII and GlcVII are bonded at one of the $R_1$, $R_2$, $R_3$ or $R_4$ positions, and the other positions are hydrogen.

The bond between GlcIII and GlcVII can be an α- or β-linkage. More particularly, the bonds can be selected from β-(1,2)-linkages, β-(1,3)-linkages, β-(1,4)-linkages, β-(1,6)-linkages, α-(1,2)-linkages, α-(1,3)-linkages, α-(1,4)-linkages, α-(1,6)-linkages.

In a particular embodiment, the mogroside of Formula II is the following:

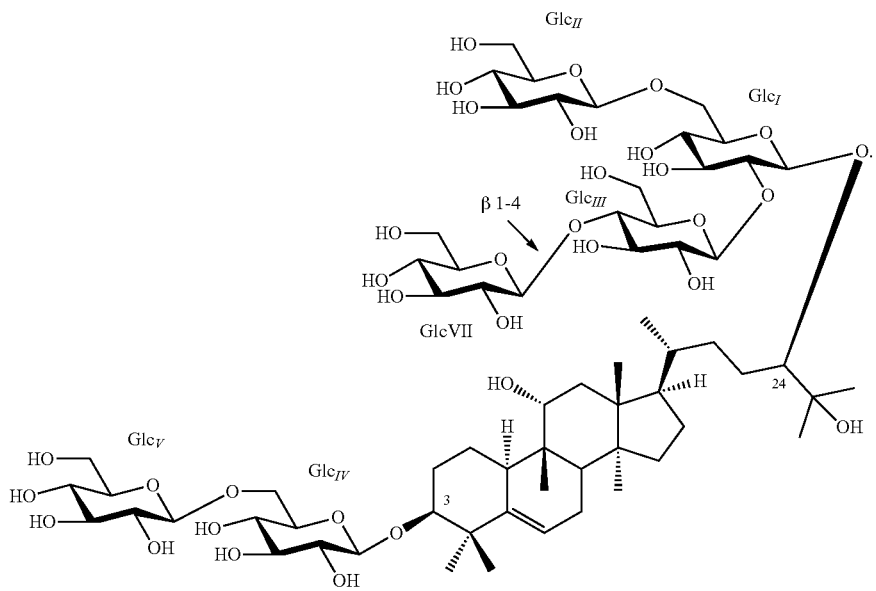

The present invention also provides a novel mogroside of Formula III:

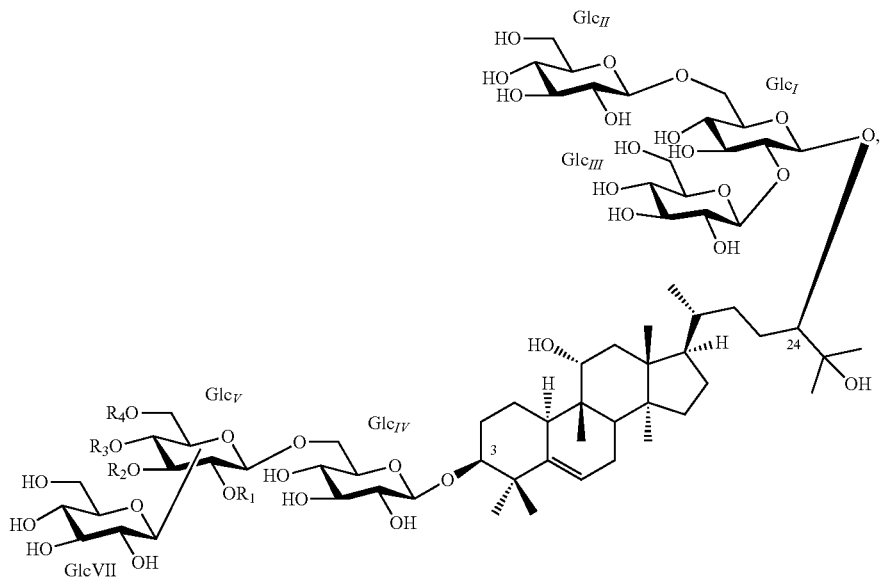

Formula III wherein GlcV and GlcVII are bonded at one of the $R_1$, $R_2$, $R_3$ or $R_4$ positions, and the other positions are hydrogen.

The bond between GlcV and GlcVII can be an α- or β-linkage. More particularly, the bonds can be selected from β-(1,2)-linkages, β-(1,3)-linkages, β-(1,4)-linkages, β-(1,6)-linkages, α-(1,2)-linkages, α-(1,3)-linkages, α-(1,4)-linkages, α-(1,6)-linkages.

In a particular embodiment, the mogroside of Formula III is selected from the following:
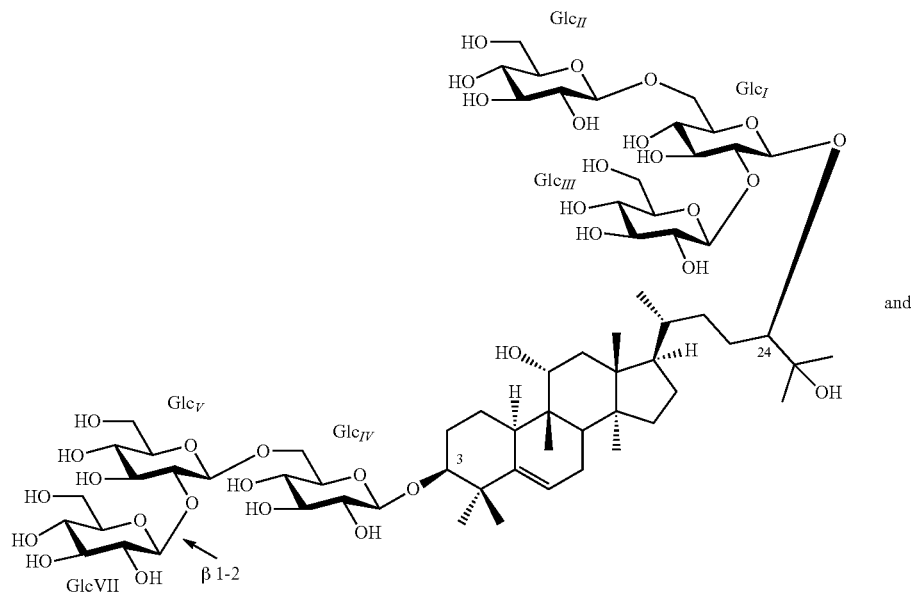
CC-00401
and
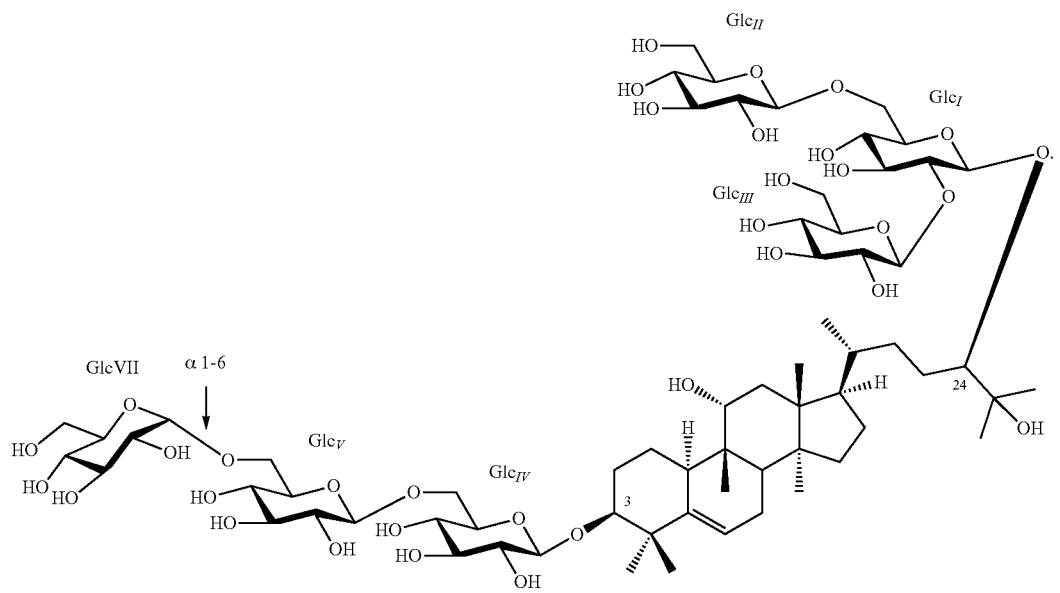
CC-00436

Mogroside IIIE has the following structure:

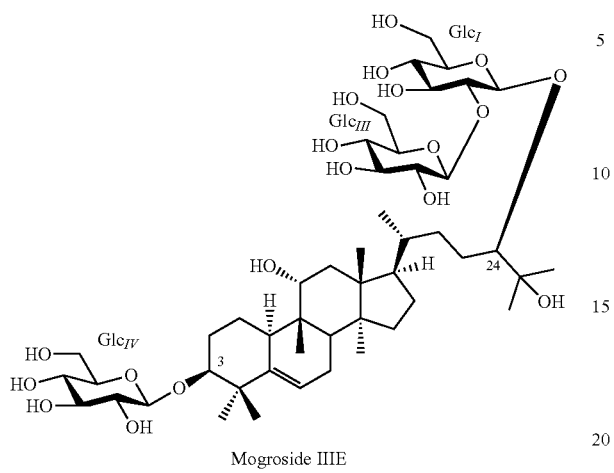

Mogroside IIIE

Mogroside IIIE contains three glucose units pendant to the mogrol core. All of the linkages between the core and the glucose substituents at C24 and C3 as well as linkages between glucose units, are β-linkages. There is a β1→2 linkage between GlcI and GlcIII. Novel compounds of the present invention that are derivatives of Mogroside IIIE also contain GlcI, GlcIII and GlcIV in the same configuration as Mogroside IIIE, with additional glucose substituents on GlcIII.

The present invention provides novel mogrosides of Formula IV:

Formula IV

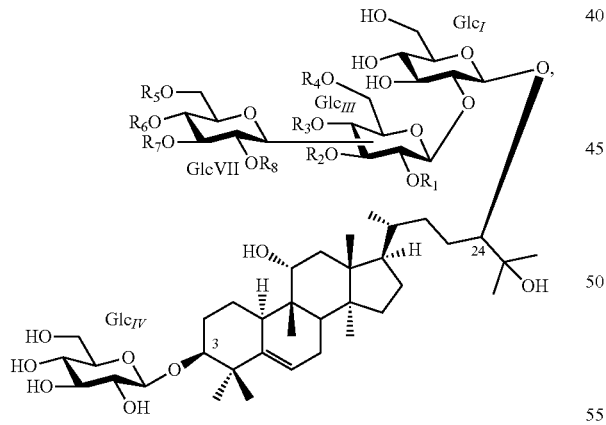

wherein GlcIII and GlcVII are bonded at one of the $R_1$, $R_2$, $R_3$ or $R_4$ positions, and the other positions are hydrogen; and wherein $R_5$, $R_6$, $R_7$ and $R_8$ are each independently selected from hydrogen and glucose.

The bond between GlcIII and GlcVII can be an α- or β-linkage. More particularly, the bonds can be selected from β-(1,2)-linkages, β-(1,3)-linkages, β-(1,4)-linkages, β-(1,6)-linkages, α-(1,2)-linkages, α-(1,3)-linkages, α-(1,4)-linkages, α-(1,6)-linkages.

In a particular embodiment, one of $R_5$, $R_6$, $R_7$ or $R_8$ is glucose. The linkage between the glucose at one of $R_5$, $R_6$, $R_7$ or $R_8$ and GlcVII can be an α- or β-linkage.

In a particular embodiment, the mogroside of Formula IV is selected from the following:

CC-00434

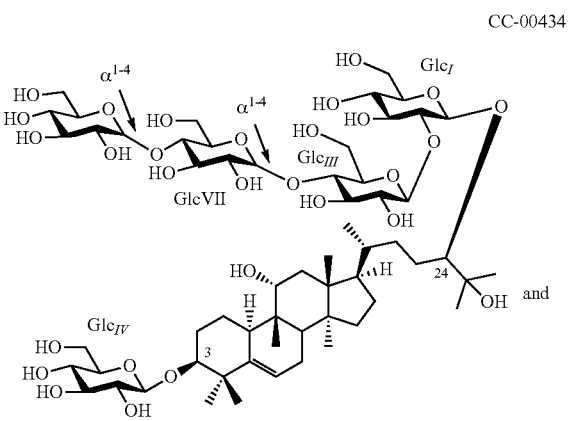

and

CC-00478

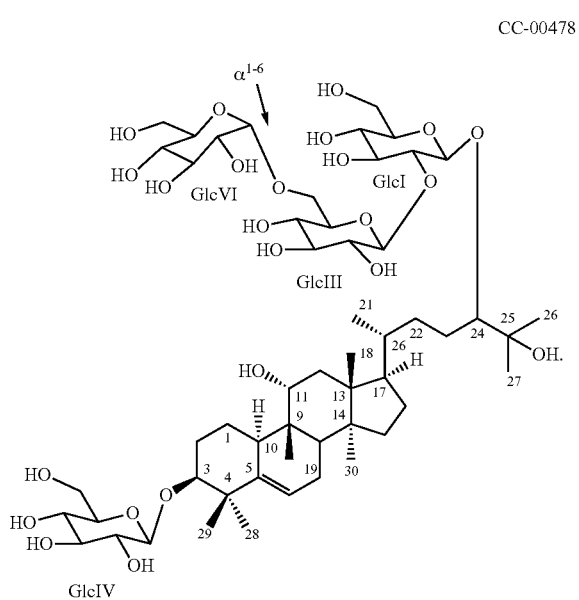

In another embodiment, the present invention provides mogrosides of Formula V:

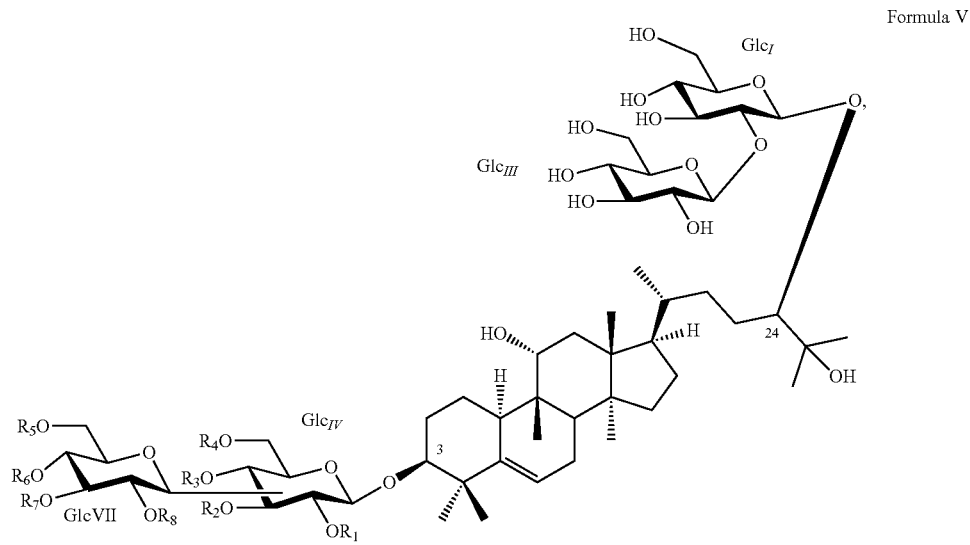

Formula V wherein GlcIV and GlcVII are bonded at one of the $R_1$, $R_2$, $R_3$ or $R_4$ positions, and the other positions are hydrogen; and wherein $R_5$, $R_6$, $R_7$ and $R_8$ are each independently selected from hydrogen and glucose.

The bond between GlcIV and GlcVII can be an α- or β-linkage. More particularly, the bonds can be selected from β-(1,2)-linkages, β-(1,3)-linkages, β-(1,4)-linkages, β-(1,6)-linkages, α-(1,2)-linkages, α-(1,3)-linkages, α-(1,4)-linkages, α-(1,6)-linkages.

In a particular embodiment, one of $R_5$, $R_6$, $R_7$ or $R_8$ is glucose. The linkage between the glucose at one of $R_5$, $R_6$, $R_7$ or $R_8$ and GlcVII can be an α- or β-linkage.

In a particular embodiment, the mogroside of Formula V is selected from the following:

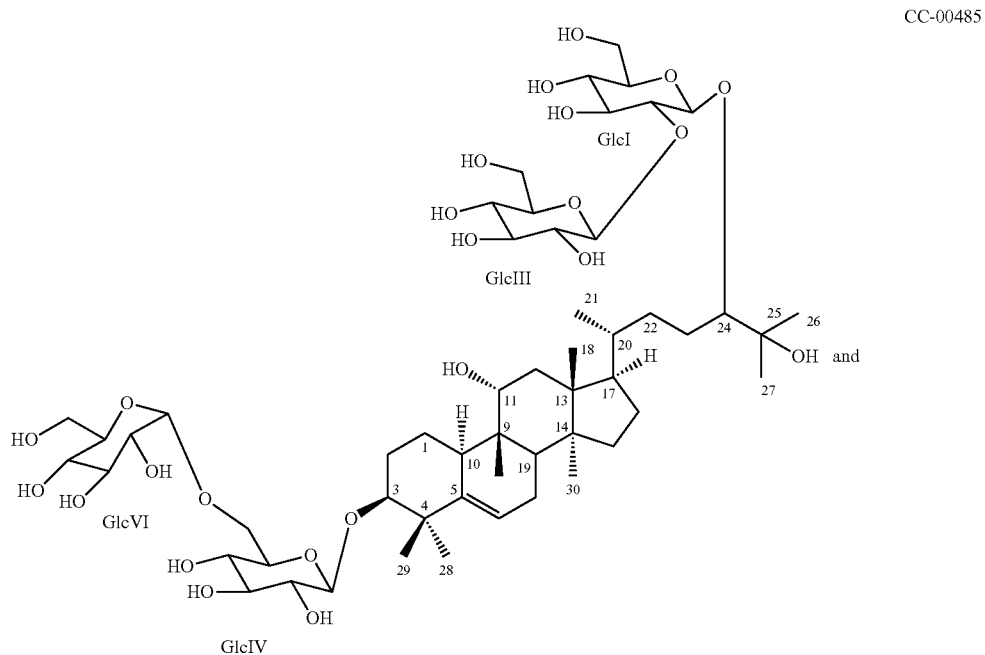

and

-continued

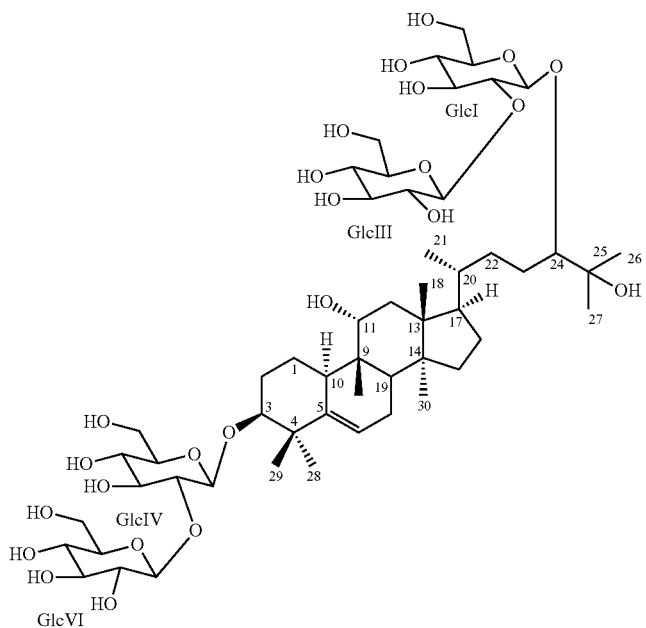

Mogroside IV has the following structure:

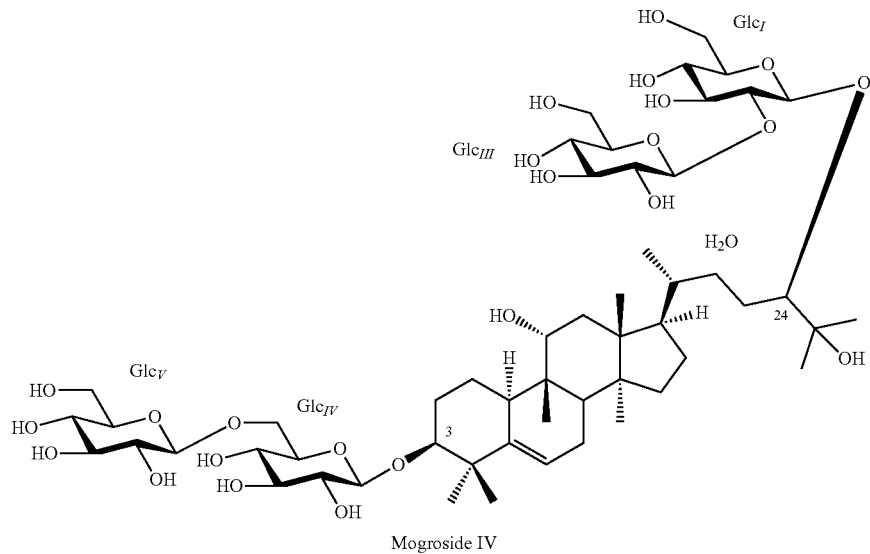

Mogroside IV

Mogroside IV contains four glucose units pendant to the mogrol core. All of the linkages between the core and the glucose substituents at C24 and C3 as well as linkages between glucose units, are β-linkages.

Novel compounds of the present invention that are derivatives of Mogroside IV also contain GlcI, GlcIII, GlcIV and GlcV in the same configuration as Mogroside IV, with additional glucose substituents.

The present invention provides novel mogrosides of Formula VI:

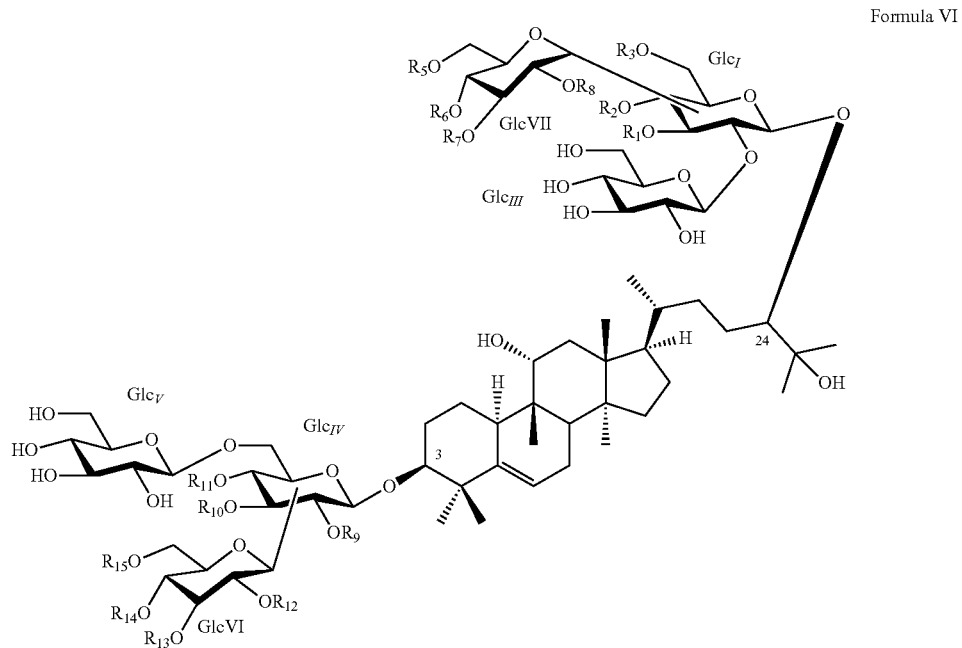

Formula VI wherein GlcI and GlcVII are bonded at one of the $R_1$, $R_2$ or $R_3$ positions and the other positions are hydrogen; GlcIV and GlcVI are bonded at one of the $R_9$, $R_{10}$ or $R_{11}$ positions and the other positions are hydrogen; and $R_5$, $R_6$, $R_7$, $R_8$, $R_9$, $R_{12}$, $R_{13}$, $R_{14}$ and $R_{15}$ are each independently selected from hydrogen and glucose.

The bond between (i) GlcI and GlcVII and (ii) GlcIV and GlcVI can be an α- or β-linkage. More particularly, the bonds can be selected from β-(1,2)-linkages, β-(1,3)-linkages, β-(1,4)-linkages, β-(1,6)-linkages, α-(1,2)-linkages, α-(1,3)-linkages, α-(1,4)-linkages, α-(1,6)-linkages.

In a particular embodiment, the mogroside of Formula VI is the following:

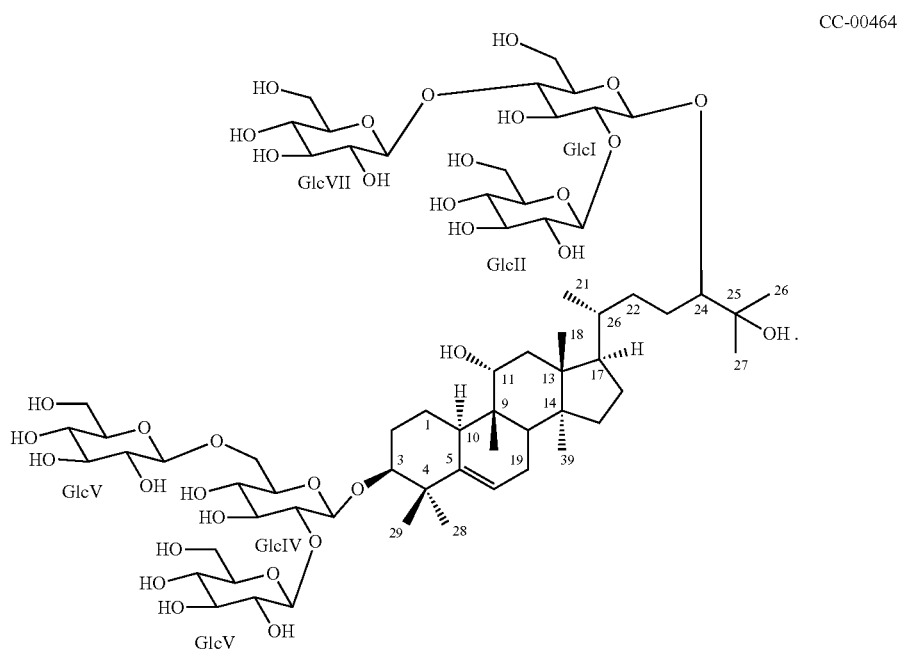

In another embodiment, the present invention provides mogrosides of Formula VII:

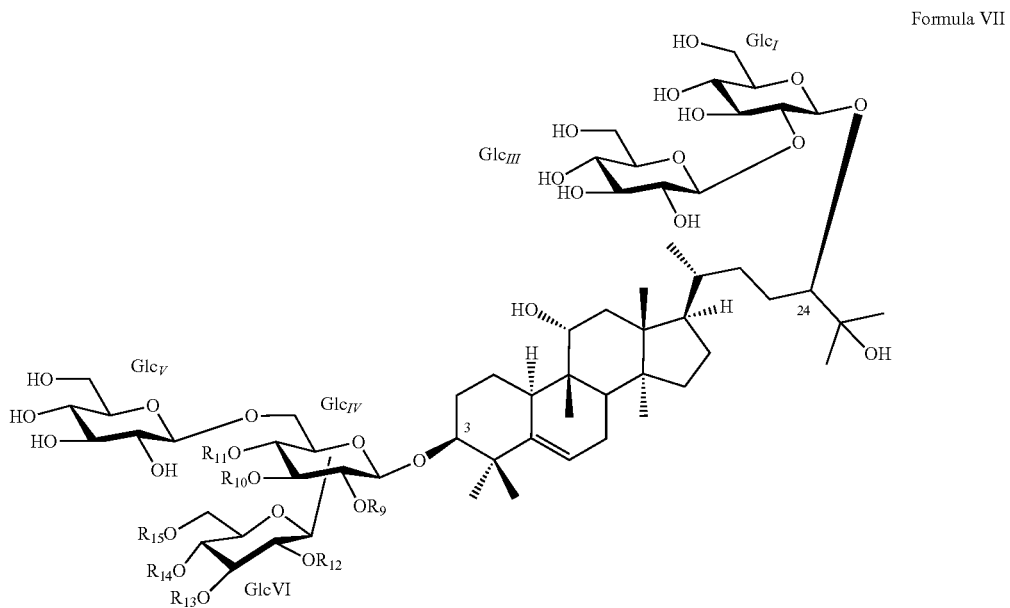

Formula VII wherein GlcIV and GlcVI are bonded at one of the $R_9$, $R_{10}$ or $R_{11}$ positions and the other positions are hydrogen; and $R_{12}$, $R_{13}$, $R_{14}$ and $R_{15}$ are each independently selected from hydrogen and glucose.

The bond between GlcIV and GlcVI can be an α- or β-linkage. More particularly, the bonds can be selected from β-(1,2)-linkages, β-(1,3)-linkages, β-(1,4)-linkages, β-(1,6)-linkages, α-(1,2)-linkages, α-(1,3)-linkages, α-(1,4)-linkages, α-(1,6)-linkages.

In a particular embodiment, the mogroside of Formula VII is the following:

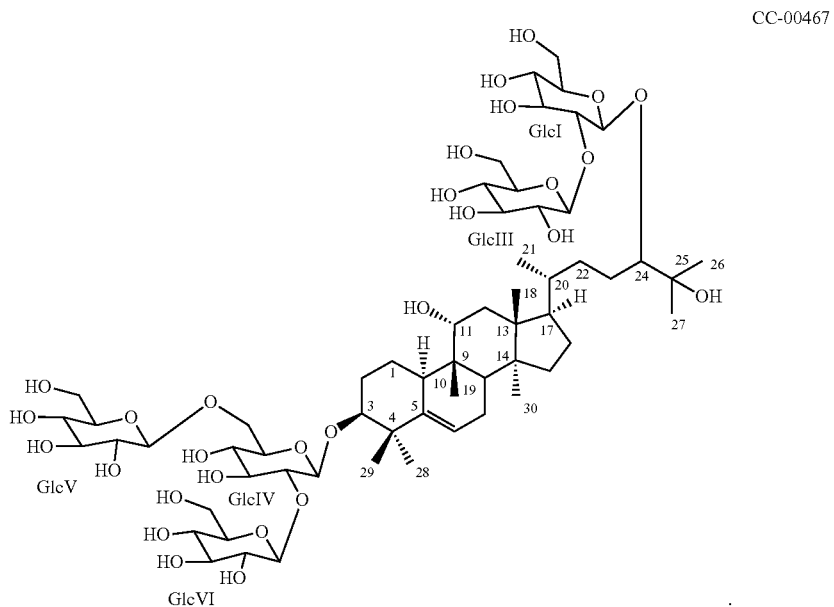

CC-00467

In another embodiment, the present invention provides mogrosides of Formula VIII:

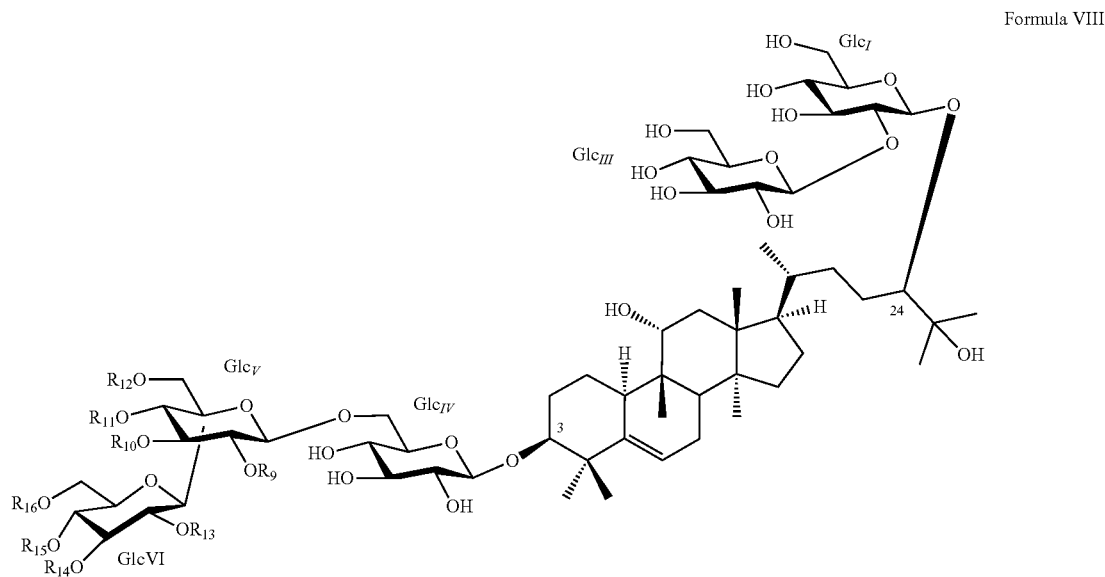

Formula VIII wherein GlcV and GlcVI are bonded at one of the $R_9$, $R_{10}$, $R_{11}$ or $R_{12}$ positions and the other positions are hydrogen; and $R_{13}$, $R_{14}$, $R_{15}$ and $R_{16}$ are each independently selected from hydrogen and glucose.

The bond between GlcV and GlcVI can be an α- or β-linkage. More particularly, the bonds can be selected from β-(1,2)-linkages, β-(1,3)-linkages, β-(1,4)-linkages, β-(1,6)-linkages, α-(1,2)-linkages, α-(1,3)-linkages, α-(1,4)-linkages, α-(1,6)-linkages.

In a particular embodiment, the mogroside of Formula VIII is the following:

In exemplary embodiments, the mogroside of the present invention is isolated and purified. The term "isolated and purified", as used herein, means that the mogroside is about 90% by weight or greater on a dry basis, i.e. is greater than 90% pure. The remainder of the mixture is typically other mogrosides and/or Luo Han Guo extract. In more specific embodiments, the mogroside of the formulae described herein has a purity of about 95% or greater, 96% or greater, about 97% or greater, about 98% or greater or about 99% or greater.

In some embodiments, the mogroside of the present invention is sweet. The sweetness of a given composition is typically measured with reference to a solution of sucrose.

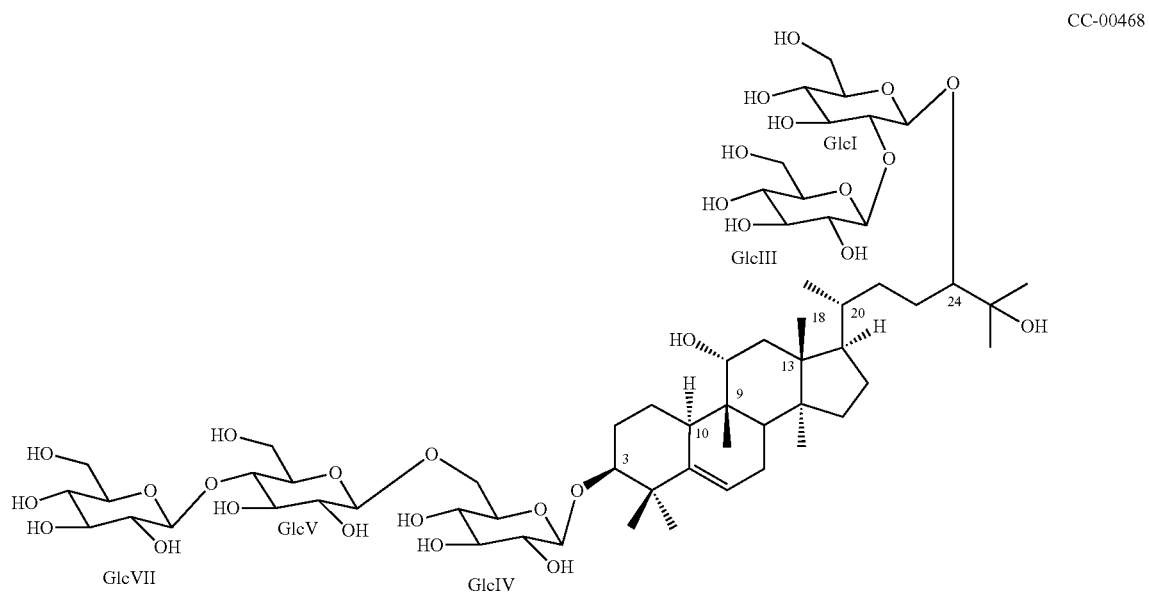

CC-00468

See generally "A Systematic Study of Concentration-Response Relationships of Sweeteners," G. E. DuBois, D. E.

Walters, S. S. Schiffman, Z. S. Warwick, B. J. Booth, S. D. Pecore, K. Gibes, B. T. Carr, and L. M. Brands, in *Sweeteners: Discovery, Molecular Design and Chemoreception*, D. E. Walters, F. T. Orthoefer, and G. E. DuBois, Eds., American Chemical Society, Washington, DC (1991), pp 261-276.

The sweetness of a non-sucrose sweetener can be measured against a sucrose reference by determining the non-sucrose sweetener's sucrose equivalence (SE). Typically, taste panelists are trained to detect sweetness of reference sucrose solutions containing between 1-15% sucrose (w/v). Other non-sucrose sweeteners are then tasted at a series of dilutions to determine the concentration of the non-sucrose sweetener that is as sweet as a given percent sucrose reference. For example, if a 1% solution of a sweetener is as sweet as a 10% sucrose solution, then the sweetener is said to be 10 times as potent as sucrose, and has 10% sucrose equivalence.

In one embodiment, the mogroside is present in an amount that, when added to a consumable, provides a sucrose equivalence of greater than about 2% (w/v), such as, for example, greater than about 3%, about 4%, about 5%, about 6%, about 7%, about 8%, about 9%, about 10%, about 11%, about 12%, about 13% or about 14%.

The amount of sucrose, and thus another measure of sweetness, in a reference solution may be described in degrees Brix (° Bx). One degree Brix is 1 gram of sucrose in 100 grams of solution and represents the strength of the solution as percentage by weight (% w/w) (strictly speaking, by mass). In one embodiment, the mogroside of the present invention is present in an amount that, when added to a consumable, provides a sweetness equivalent from about 0.50 to 14 degrees Brix, such as, for example, about 5 degrees Brix, about 6 degrees Brix, about 7 degrees Brix, about 8 degrees Brix, about 9 degrees Brix or about 10 degrees Brix or more.

In exemplary embodiments, an isolated and purified mogroside of the present invention has about 30% or more sweetness compared to the partially purified mogroside or Luo Han Guo extract, such as, for example, about 40% or more, about 50% or more, about 60% or more, about 70% or more, about 80% or more or about 90% or more.

In other exemplary embodiments, an isolated and purified mogroside of the present invention has at least about 30% less bitterness (the taste stimulated by certain substances such as quinine, caffeine and sucrose octa-acetate) compared the partially purified mogroside or Luo Han Guo extract, such as, for example, at least about 40%, at least about 50%, at least about 60%, at least about 70%, at least about 80% or at least about 90%. In a particular embodiment, the isolated and purified mogroside of the present invention has substantially no bitterness. Methods of measuring bitterness of a compound are known in the art.

In still other exemplary embodiments, an isolated and purified mogroside of the present invention has at least about 30% less sweet lingering aftertaste (the intensity of the sweet taste after expectoration) compared to the partially purified mogroside or mogroside or Luo Han Guo extract, such as, for example, at least about 50%, at least about 60%, at least about 70%, at least about 80% or at least about 90%. In a particular embodiment, the isolated and mogroside of the present invention has substantially no sweet lingering aftertaste. Methods of measuring sweet lingering aftertaste are known in the art.

In yet other exemplary embodiments, an isolated and purified mogroside of the present invention has at least about 30% less metallic taste (taste associated with metals, tinny or iron) compared to the partially purified mogroside or Luo Han Guo extract, such as, for example, at least about 50%, at least about 60%, at least about 70%, at least about 80% or at least about 90%. In a particular embodiment, the isolated and purified mogroside of the present invention has substantially no metallic taste.

In exemplary embodiments, an isolated and purified mogroside of the present invention exhibits a maximal response (maximum sweetness (% SE) achieved with increasing concentration of compound) that is at least about 30% greater compared to the partially purified mogroside or Luo Han Guo extract, such as, for example, at least about 40% greater, at least about 50% greater, at least about 60% greater, at least about 70% greater, at least about 80% greater or at least about 90% greater. Methods of measuring the maximal response of a compound are known in the art. In one embodiment, the method is an in vitro cell assay. In some embodiments, the cell is expressing a sweet taste receptor or a dimer of sweet taste receptor.

In other exemplary embodiments, an isolated and purified mogroside of the present invention exhibits a sweetness onset (the time until maximum sweetness is experienced) that is at least about 30% shorter than the partially purified mogroside or Luo Han Guo extract, such as, for example, at least about 40% short, at least about 50% shorter, at least about 60% shorter, at least about 70% shorter, at least about 80% shorter or at least about 90% shorter. Methods of measuring sweetness onset are known in the art. In one embodiment, the method is an in vitro cell assay. In some embodiments, the cell is expressing a sweet taste receptor or a dimer of sweet taste receptor.

II. Compositions

The present invention includes compositions comprising at least one mogroside of the present invention. "Composition," as the term is used herein, refers to a mixture of at least one mogroside of the present invention and at least one other substance, wherein the mogroside is admixed with the at least one other substance. As used herein, "admix" means to mingle or add to something else, but in any case, requires an active step.

In a particular embodiment, the at least one other substance does not occur and/or is not admixed with the mogroside in nature, i.e. the Luo Han Guo extract. As such, the compositions contemplated by the present invention do not occur in nature.

In one embodiment, the present invention is a composition comprising at least one mogroside of the present invention, provided as part of a mixture. In a particular embodiment, the mixture is selected from the group consisting of consisting of a mixture of mogrosides, a Luo Han Guo extract, by-products of other mogrosides' isolation and purification processes, a commercially available Luo Han Guo extract or any combination thereof.

In one embodiment, the mixture contains at least mogroside of the present invention in an amount that ranges from about 1% to about 99% by weight on a dry basis, such as, for example, about 5% to about 99% by weight on a dry basis, from about 10% to about 99%, from about 20% to about 99%, from about 30% to about 99%, from about 40% to about 99%, from about 50% to about 99%, from about 60% to about 99%, from about 70% to about 99%, from about 80% to about 99% and from about 90% to about 99%. In a particular embodiment, the mixture contains at least one mogroside of the present invention in an amount greater than about 90% by weight on a dry basis, for example, greater than about 91%, greater than about 92%, greater than about 93%, greater than about 94%, greater than about 95%, greater than about 96%, greater than about 97%, greater than about 98% and greater than about 99%.

In a particular embodiment, the mixture is a Luo Han Guo an extract.

The mixture may contain one or more additional mogrosides, i.e., mogrosides that are not the novel mogrosides of the present invention, including, but not limited to, grosmogroside I, mogroside IA, mogroside IE, 11-oxomogroside IA, mogroside II, mogroside II A, mogroside II B, mogroside II E, 7-oxomogroside II E, mogroside III, Mogroside IIe, 11-deoxymogroside III, mogroside IV, 11-oxomogroside IV, 11-oxomogroside IV A, mogroside V, isomogroside V, 11-deoxymogroside V, 7-oxomogroside V, 11-oxomogroside V, isomogroside V, mogroside VI, mogrol, 11-oxomogrol, siamenoside I, mogro-3-O-[β-D-glucopyranoside]-24-O-{[β-D-glucopyranosyl-(1→2)]-[α-D-glucopyranosyl-(1→6)]-β-D-glucopyranoside} and combinations thereof.

In one embodiment, the present invention is a composition comprising at least one mogroside described herein provided as a pure compound, i.e. >99% purity on a dry basis.

The mogroside of the present invention may be present in the composition in an amount effective to provide a concentration of mogroside of the present invention from about 1 ppm to about 10,000 ppm when the composition is added to a consumable, such as, for example, from about 1 ppm to about 4,000 ppm, from about 1 ppm to about 3,000 ppm, from about 1 ppm to about 2,000 ppm, from about 1 ppm to about 1,000 ppm.

In another embodiment, the mogroside of the present invention is present in the composition in an amount effective to provide a concentration of mogroside of the present invention from about 10 ppm to about 1,000 ppm when the composition is added to a consumable, such as, for example, from about 10 ppm to about 800 ppm, from about 50 ppm to about 800 ppm, or from about 50 ppm to about 600 ppm.

Sweetener Compositions

In some embodiments, the mogroside of the present invention is sweet. Accordingly, the present invention also provides a sweetener composition comprising at least one mogroside of the present invention. "Sweetener composition," as the term is used herein, refers to a mixture of at least one mogroside of the present invention and at least one other substance, wherein the at least one mogroside is admixed with the at least one other substance.

In a particular embodiment, the at least one other substance does not occur and/or is not admixed with the mogroside in nature. As such, the sweetener compositions contemplated by the present invention do not occur in nature. In one embodiment, the at least one other substance modulates the taste profile of the at least one mogroside to provide a composition with a more sucrose-like taste profile compared to the mogroside in nature and (if applicable) the at least one other substance in nature. For example, in certain embodiments the composition exhibits one or more of the following characteristics: improved sweetness potency, improved mouthfeel, decreased sweetness linger, decreased bitterness and/or decreased metallic taste.

In certain exemplary embodiments, the sweetener composition comprises at least one purified mogroside of this invention.

In one embodiment, the mogroside of the present invention is the sole sweetener in the sweetener composition, i.e. the mogroside is the only compound present in the sweetener composition that provides a detectable sweetness.

In further embodiments, the sweetener composition comprising at least one mogroside of the present invention in combination with at least one additional sweetener. In a particular embodiment, the at least one additional sweetener does not occur with the mogroside in nature. In a more particular embodiment, a sweetener composition comprises at least one purified mogroside at least one additional sweetener that does not occur with the mogroside in nature.

The amount of the mogroside of the present invention in the sweetener composition may vary. In one embodiment, the mogroside of the present invention is present in a sweetener composition in any amount to impart the desired sweetness when the sweetener composition is added to a consumable. In a particular embodiment, the mogroside of the present invention is present in a concentration above its threshold sweetness recognition concentration.

In one embodiment, the mogroside of the present invention is present in the sweetener composition in an amount effective to provide a sucrose equivalence of greater than about 2% (w/v) when the sweetener composition is added to a consumable, such as, for example, greater than about 3%, about 4%, about 5%, about 6%, about 7%, about 8%, about 9%, about 10%, about 11%, about 12%, about 13% or about 14%.

In some embodiments, the mogroside of the present invention is present in the sweetener composition in an amount that, when added to a consumable, will provide a concentration of the mogroside of the present invention from about 1 ppm to about 100 ppm, such as, for example, from about 1 ppm to about 90 ppm, from about 5 ppm to about 80 ppm, from about 5 ppm to about 70 ppm, from about 5 ppm to about 60 ppm, from about 5 ppm to about 50 ppm, from about 5 ppm to about 40 ppm, from about 5 ppm to about 30 ppm, from about 5 ppm to about 20 ppm, or 5 ppm to about 15 ppm.

In other embodiments, a mogroside of the present invention is present in the sweetener composition in an amount that, when added to a consumable, will provide a concentration of the mogroside of the present invention greater than about 10 ppm, such as, for example, greater than about 20 ppm, about 30 ppm, about 40 ppm, about 50 ppm, about 60 ppm, about 70 ppm, about 80 ppm, about 90 ppm, about 100 ppm, about 200 ppm, about 300 ppm, about 400 ppm, about 500 ppm, about 600 ppm, about 700 ppm, about 800 ppm or about 900 ppm.

In still other embodiments, a mogroside of the present invention is present in the sweetener composition in an amount that, when added to a consumable, will provide a concentration of the mogroside of the present invention from about 1 ppm to about 1,000 ppm, such as, for example, from about 10 ppm to about 1,000 ppm, from about 20 ppm to about 1,000 ppm, from about 30 ppm to about 1,000 ppm, from about 30 ppm to about 1,000 ppm, from about 40 ppm to about 1,000 ppm, from about 50 ppm to about 1,000 ppm, from about 60 ppm to about 1,000 ppm, from about 70 ppm to about 1,000 ppm, from about 80 ppm to about 1,000 ppm, from about 90 ppm to about 1,000 ppm, from about 100 ppm to about 1,000 ppm, from about 200 ppm to about 1,000 ppm, from about 300 ppm to about 1,000 ppm, from about 400 ppm to about 1,000 ppm, from about 500 ppm to about 1,000 ppm, from about 600 ppm to about 1,000 ppm, from about 700 ppm to about 1,000 ppm, from about 800 ppm to about 1,000 ppm, from about 900 ppm to about 1,000 ppm or from about 50 ppm to about 600 ppm.

In one embodiment, the sweetener is at least one natural high-potency sweetener. As used herein, the phrase "natural high potency sweetener" refers to any sweetener found naturally in nature and characteristically has a sweetness potency greater than sucrose, fructose, or glucose, yet has less calories. The natural high potency sweetener can be provided as a pure compound or, alternatively, as part of an extract.

In another embodiment, the sweetener is at least one synthetic sweetener. As used herein, the phrase "synthetic sweetener" refers to any composition which is not found naturally in nature and characteristically has a sweetness potency greater than sucrose, fructose, or glucose, yet has less calories.

In still other embodiments, combinations of natural high potency sweeteners and synthetic sweeteners are contemplated.

In other embodiments, the sweetener is at least one carbohydrate sweetener. Suitable carbohydrate sweeteners are selected from, but not limited to, the group consisting of sucrose, glyceraldehyde, dihydroxyacetone, erythrose, threose, erythrulose, arabinose, lyxose, ribose, xylose, ribulose, xylulose, allose, altrose, galactose, glucose, gulose, idose, mannose, talose, fructose, psicose, sorbose, tagatose, mannoheptulose, sedoheltulose, octolose, fucose, rhamnose, arabinose, turanose, sialose and combinations thereof.

Other suitable sweeteners include rebaudioside A, rebaudioside B, rebaudioside C, rebaudioside D, rebaudioside E, rebaudioside F, rebaudioside I, rebaudioside H, rebaudioside L, rebaudioside K, rebaudioside J, rebaudioside M, rebaudioside N, rebaudioside O, dulcoside A, dulcoside B, rubusoside, *stevia*, stevioside, mogroside IV, mogroside IVA, mogroside V, mogroside VI, mogroside IIIE, Isomogrosdie V, siamenoside I, monatin and its salts (monatin SS, RR, RS, SR), curculin, glycyrrhizic acid and its salts, thaumatin, monellin, mabinlin, brazzein, hernandulcin, phyllodulcin, glycyphyllin, phloridzin, trilobatin, baiyunoside, osladin, polypodoside A, pterocaryoside A, pterocaryoside B, mukurozioside, phlomisoside I, periandrin I, abrusoside A, steviolbioside, hesperitin and cyclocarioside I, sugar alcohols such as erythritol, sucralose, potassium acesulfame, acesulfame acid and salts thereof, aspartame, alitame, saccharin and salts thereof, neohesperidin dihydrochalcone, cyclamate, cyclamic acid and salts thereof, neotame, advantame, glucosylated steviol glycosides (GSGs) and combinations thereof.

In a particular embodiment, the sweetener is at least one calorie-providing carbohydrate sweetener. Accordingly, incorporation of the sweetness enhancer reduces the quantity of the calorie-providing carbohydrate sweetener that must be used in a given consumable to achieve a particular SE, thereby allowing the preparation of reduced-calorie consumables.

In one embodiment, the sweetener is a caloric sweetener or mixture of caloric sweeteners. In another embodiment, the caloric sweetener is selected from sucrose, fructose, glucose, high fructose corn/starch syrup, a beet sugar, a cane sugar, and combinations thereof.

In another embodiment, the sweetener is a rare sugar selected from allulose, sorbose, lyxose, ribulose, xylose, xylulose, D-allose, L-ribose, D-tagatose, L-glucose, L-fucose, L-arabinose, turanose, kojibiose and combinations thereof.

In still another embodiment, the sweetener is a mixture of at least one natural high potency sweeteners and at least one carbohydrate sweetener. In yet another embodiment, the sweetener is a mixture of at least one synthetic sweetener and at least one carbohydrate sweetener. In a further embodiment, the sweetener is at least one natural high potency sweetener, at least one synthetic sweetener and at least one carbohydrate sweetener.

In exemplary embodiments, a sweetener composition comprising at least one isolated and purified mogroside of the present invention has about 30% or more sweetness compared to a corresponding sweetener composition comprising partially purified mogroside or Luo Han Guo extract, such as, for example, about 40% or more, about 50% or more, about 60% or more, about 70% or more, about 80% or more or about 90% or more.

In other exemplary embodiments, a sweetener composition comprising at least one isolated and purified mogroside of the present invention has at least about 30% less bitterness (the taste stimulated by certain substances such as quinine, caffeine and sucrose octa-acetate) compared to a corresponding composition comprising partially purified mogroside or Luo Han Guo extract, such as, for example, at least about 40%, at least about 50%, at least about 60%, at least about 70%, at least about 80% or at least about 90%. In a particular embodiment, a sweetener composition comprising at least one isolated and purified mogroside of the present invention has substantially no bitterness. Methods of measuring bitterness of a compound are known in the art In still other exemplary embodiments, a sweetener composition comprising at least one isolated and purified mogroside of the present invention has at least about 30% less sweet lingering aftertaste (the intensity of the sweet taste after expectoration) compared to a corresponding sweetener composition comprising partially purified mogroside or Luo Han Guo extract, such as, for example, at least about 50%, at least about 60%, at least about 70%, at least about 80% or at least about 90%. In a particular embodiment, a sweetener composition comprising at least one isolated and purified mogroside of the present invention has substantially no sweet lingering aftertaste. Methods of measuring sweet lingering aftertaste are known in the art.

In yet other exemplary embodiments, a sweetener composition comprising at least one isolated and purified mogroside of the present invention has at least about 30% less metallic taste (taste associated with metals, tinny or iron) compared to a corresponding sweetener composition comprising partially purified mogroside or Luo Han Guo extract, such as, for example, at least about 50%, at least about 60%, at least about 70%, at least about 80% or at least about 90%. In a particular embodiment, a sweetener composition comprising at least one isolated and purified mogroside of the present invention has substantially no metallic taste.

In exemplary embodiments, a sweetener composition comprising at least one isolated and purified mogroside of the present invention exhibits a maximal response (maximum sweetness (% SE) achieved with increasing concentration of compound) that is at least about 30% greater compared to a corresponding sweetener composition comprising partially purified mogroside or Luo Han Guo extract, such as, for example, at least about 40% greater, at least about 50% greater, at least about 60% greater, at least about 70% greater, at least about 80% greater or at least about 90% greater. Methods of measuring the maximal response of a compound are known in the art.

In other exemplary embodiments, a sweetener composition comprising at least one isolated and purified mogroside of the present invention exhibits a sweetness onset (the time until maximum sweetness is experienced) that is at least about 30% shorter than a sweetener composition comprising partially purified mogroside or Luo Han Guo extract, such as, for example, at least about 40% short, at least about 50% shorter, at least about 60% shorter, at least about 70% shorter, at least about 80% shorter or at least about 90% shorter. Methods of measuring sweetness onset are known in the art.

Additives

The compositions may comprise, in addition to at least one mogroside of the present invention, one or more additives and/or functional ingredients, detailed herein below.

Exemplary additives include, but not limited to, carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, caffeine, flavorants and flavoring ingredients, astringent compounds, proteins or protein hydrolysates, surfactants, emulsifiers, plant extracts, flavonoids, alcohols, polymers and combinations thereof.

In one embodiment, the composition further comprises one or more polyols. The term "polyol", as used herein, refers to a molecule that contains more than one hydroxyl group. A polyol may be a diol, triol, or a tetraol which contains 2, 3, and 4 hydroxyl groups respectively. A polyol also may contain more than 4 hydroxyl groups, such as a pentaol, hexaol, heptaol, or the like, which contain 5, 6, or 7 hydroxyl groups, respectively. Additionally, a polyol also may be a sugar alcohol, polyhydric alcohol, or polyalcohol which is a reduced form of carbohydrate, wherein the carbonyl group (aldehyde or ketone, reducing sugar) has been reduced to a primary or secondary hydroxyl group.

Non-limiting examples of polyols in some embodiments include maltitol, mannitol, sorbitol, lactitol, xylitol, isomalt, propylene glycol, glycerol (glycerin), threitol, galactitol, palatinose, reduced isomalto-oligosaccharides, reduced xylo-oligosaccharides, reduced gentio-oligosaccharides, reduced maltose syrup, reduced glucose syrup, and sugar alcohols or any other carbohydrates capable of being reduced which do not adversely affect taste.

Suitable amino acid additives include, but are not limited to, aspartic acid, arginine, glycine, glutamic acid, proline, threonine, theanine, cysteine, cystine, alanine, valine, tyrosine, leucine, arabinose, trans-4-hydroxyproline, isoleucine, asparagine, serine, lysine, histidine, ornithine, methionine, carnitine, aminobutyric acid (α-, β-, and/or δ-isomers), glutamine, hydroxyproline, taurine, norvaline, sarcosine, and their salt forms such as sodium or potassium salts or acid salts. The amino acid additives also may be in the D- or L-configuration and in the mono-, di-, or tri-form of the same or different amino acids. Additionally, the amino acids may be α-, β-, γ- and/or δ-isomers if appropriate. Combinations of the foregoing amino acids and their corresponding salts (e.g., sodium, potassium, calcium, magnesium salts or other alkali or alkaline earth metal salts thereof, or acid salts) also are suitable additives in some embodiments. The amino acids may be natural or synthetic. The amino acids also may be modified. Modified amino acids refers to any amino acid wherein at least one atom has been added, removed, substituted, or combinations thereof (e.g., N-alkyl amino acid, N-acyl amino acid, or N-methyl amino acid). Non-limiting examples of modified amino acids include amino acid derivatives such as trimethyl glycine, N-methyl-glycine, and N-methyl-alanine. As used herein, modified amino acids encompass both modified and unmodified amino acids. As used herein, amino acids also encompass both peptides and polypeptides (e.g., dipeptides, tripeptides, tetrapeptides, and pentapeptides) such as glutathione and L-alanyl-L-glutamine. Suitable polyamino acid additives include poly-L-aspartic acid, poly-L-lysine (e.g., poly-L-α-lysine or poly-L-ε-lysine), poly-L-ornithine (e.g., poly-L-α-ornithine or poly-L-ε-ornithine), poly-L-arginine, other polymeric forms of amino acids, and salt forms thereof (e.g., calcium, potassium, sodium, or magnesium salts such as L-glutamic acid mono sodium salt). The poly-amino acid additives also may be in the D- or L-configuration. Additionally, the poly-amino acids may be α-, β-, γ-, δ-, and ε-isomers if appropriate. Combinations of the foregoing poly-amino acids and their corresponding salts (e.g., sodium, potassium, calcium, magnesium salts or other alkali or alkaline earth metal salts thereof or acid salts) also are suitable additives in some embodiments. The poly-amino acids described herein also may comprise co-polymers of different amino acids. The poly-amino acids may be natural or synthetic. The poly-amino acids also may be modified, such that at least one atom has been added, removed, substituted, or combinations thereof (e.g., N-alkyl poly-amino acid or N-acyl poly-amino acid). As used herein, poly-amino acids encompass both modified and unmodified poly-amino acids. For example, modified poly-amino acids include, but are not limited to, poly-amino acids of various molecular weights (MW), such as poly-L-α-lysine with a MW of 1,500, MW of 6,000, MW of 25,200, MW of 63,000, MW of 83,000, or MW of 300,000.

Suitable sugar acid additives include, but are not limited to, aldonic, uronic, aldaric, alginic, gluconic, glucuronic, glucaric, galactaric, galacturonic, and salts thereof (e.g., sodium, potassium, calcium, magnesium salts or other physiologically acceptable salts), and combinations thereof.

Suitable nucleotide additives include, but are not limited to, inosine monophosphate ("IMP"), guanosine monophosphate ("GMP"), adenosine monophosphate ("AMP"), cytosine monophosphate (CMP), uracil monophosphate (UMP), inosine diphosphate, guanosine diphosphate, adenosine diphosphate, cytosine diphosphate, uracil diphosphate, inosine triphosphate, guanosine triphosphate, adenosine triphosphate, cytosine triphosphate, uracil triphosphate, alkali or alkaline earth metal salts thereof, and combinations thereof. The nucleotides described herein also may comprise nucleotide-related additives, such as nucleosides or nucleic acid bases (e.g., guanine, cytosine, adenine, thymine, uracil).

Suitable organic acid additives include any compound which comprises a —COOH moiety, such as, for example, C2-C30 carboxylic acids, substituted hydroxyl C2-C30 carboxylic acids, butyric acid (ethyl esters), substituted butyric acid (ethyl esters), benzoic acid, substituted benzoic acids (e.g., 2,4-dihydroxybenzoic acid), substituted cinnamic acids, hydroxyacids, substituted hydroxybenzoic acids, anisic acid substituted cyclohexyl carboxylic acids, tannic acid, aconitic acid, lactic acid, tartaric acid, citric acid, isocitric acid, gluconic acid, glucoheptonic acids, adipic acid, hydroxycitric acid, malic acid, fruitaric acid (a blend of malic, fumaric, and tartaric acids), fumaric acid, maleic acid, succinic acid, chlorogenic acid, salicylic acid, creatine, caffeic acid, bile acids, acetic acid, ascorbic acid, alginic acid, erythorbic acid, polyglutamic acid, glucono delta lactone, and their alkali or alkaline earth metal salt derivatives thereof. In addition, the organic acid additives also may be in either the D- or L-configuration.

Suitable organic acid additive salts include, but are not limited to, sodium, calcium, potassium, and magnesium salts of all organic acids, such as salts of citric acid, malic acid, tartaric acid, fumaric acid, lactic acid (e.g., sodium lactate), alginic acid (e.g., sodium alginate), ascorbic acid (e.g., sodium ascorbate), benzoic acid (e.g., sodium benzoate or potassium benzoate), sorbic acid and adipic acid. The examples of the organic acid additives described optionally may be substituted with at least one group chosen from hydrogen, alkyl, alkenyl, alkynyl, halo, haloalkyl, carboxyl, acyl, acyloxy, amino, amido, carboxyl derivatives, alkylamino, dialkylamino, arylamino, alkoxy, aryloxy, nitro, cyano, sulfo, thiol, imine, sulfonyl, sulfenyl, sulfinyl, sulfamyl, carboxalkoxy, carboxamido, phosphonyl, phosphinyl, phosphoryl, phosphino, thioester, thioether, anhydride, oximino, hydrazino, carbamyl, phosphor or phosphonato.

Suitable inorganic acid additives include, but are not limited to, phosphoric acid, phosphorous acid, polyphosphoric acid, hydrochloric acid, sulfuric acid, carbonic acid, sodium dihydrogen phosphate, and alkali or alkaline earth metal salts thereof (e.g., inositol hexaphosphate Mg/Ca).

Suitable bitter compound additives include, but are not limited to, caffeine, quinine, urea, bitter orange oil, naringin, quassia, and salts thereof.

Suitable flavorants and flavoring ingredient additives include, but are not limited to, vanillin, vanilla extract, mango extract, cinnamon, citrus, coconut, ginger, viridiflorol, almond, menthol (including menthol without mint), grape skin extract, and grape seed extract. "Flavorant" and "flavoring ingredient" are synonymous and can include natural or synthetic substances or combinations thereof. Flavorants also include any other substance which imparts flavor and may include natural or non-natural (synthetic) substances which are safe for human or animals when used in a generally accepted range. Non-limiting examples of proprietary flavorants include Döhler™ Natural Flavoring Sweetness Enhancer K14323 (Döhler™, Darmstadt, Germany), Symrise™ Natural Flavor Mask for Sweeteners 161453 and 164126 (Symrise™, Holzminden, Germany), Natural Advantage™ Bitterness Blockers 1, 2, 9 and 10 (Natural Advantage™, Freehold, New Jersey, U.S.A.), and Sucramask™ (Creative Research Management, Stockton, California, U.S.A.).

Suitable polymer additives include, but are not limited to, chitosan, pectin, pectic, pectinic, polyuronic, polygalacturonic acid, starch, food hydrocolloid or crude extracts thereof (e.g., gum acacia senegal (Fibergum™), gum acacia seyal, carageenan), poly-L-lysine (e.g., poly-L-α-lysine or poly-L-ε-lysine), poly-L-ornithine (e.g., poly-L-α-ornithine or poly-L-ε-ornithine), polypropylene glycol, polyethylene glycol, poly(ethylene glycol methyl ether), polyarginine, polyaspartic acid, polyglutamic acid, polyethylene imine, alginic acid, sodium alginate, propylene glycol alginate, and sodium polyethyleneglycolalginate, sodium hexametaphosphate and its salts, and other cationic polymers and anionic polymers.

Suitable protein or protein hydrolysate additives include, but are not limited to, bovine serum albumin (BSA), whey protein (including fractions or concentrates thereof such as 90% instant whey protein isolate, 34% whey protein, 50% hydrolyzed whey protein, and 80% whey protein concentrate), soluble rice protein, soy protein, protein isolates, protein hydrolysates, reaction products of protein hydrolysates, glycoproteins, and/or proteoglycans containing amino acids (e.g., glycine, alanine, serine, threonine, asparagine, glutamine, arginine, valine, isoleucine, leucine, norvaline, methionine, proline, tyrosine, hydroxyproline, and the like), collagen (e.g., gelatin), partially hydrolyzed collagen (e.g., hydrolyzed fish collagen), and collagen hydrolysates (e.g., porcine collagen hydrolysate).

Suitable surfactant additives include, but are not limited to, polysorbates (e.g., polyoxyethylene sorbitan monooleate (polysorbate 80), polysorbate 20, polysorbate 60), sodium dodecylbenzenesulfonate, dioctyl sulfosuccinate or dioctyl sulfosuccinate sodium, sodium dodecyl sulfate, cetylpyridinium chloride (hexadecylpyridinium chloride), hexadecyltrimethylammonium bromide, sodium cholate, carbamoyl, choline chloride, sodium glycocholate, sodium taurodeoxycholate, lauric arginate, sodium stearoyl lactylate, sodium taurocholate, lecithins, sucrose oleate esters, sucrose stearate esters, sucrose palmitate esters, sucrose laurate esters, and other emulsifiers, and the like.

Suitable flavonoid additives are classified as flavonols, flavones, flavanones, flavan-3-ols, isoflavones, or anthocyanidins. Non-limiting examples of flavonoid additives include, but are not limited to, catechins (e.g., green tea extracts such as Polyphenon™ 60, Polyphenon™ 30, and Polyphenon™ 25 (Mitsui Norin Co., Ltd., Japan), polyphenols, rutins (e.g., enzyme modified rutin Sanmelin™ AO (San-fi Gen F.F.I., Inc., Osaka, Japan)), neohesperidin, naringin, neohesperidin dihydrochalcone, and the like.

Suitable alcohol additives include, but are not limited to, ethanol.

Suitable astringent compound additives include, but are not limited to, tannic acid, europium chloride ($EuCl_3$), gadolinium chloride ($GdCl_3$), terbium chloride ($TbCl_3$), alum, tannic acid, and polyphenols (e.g., tea polyphenols).

Exemplary functional ingredients include, but are not limited to, saponins, antioxidants, dietary fiber sources, fatty acids, vitamins, glucosamine, minerals, preservatives, hydration agents, probiotics, prebiotics, weight management agents, osteoporosis management agents, phytoestrogens, long chain primary aliphatic saturated alcohols, phytosterols and combinations thereof.

In certain embodiments, the functional ingredient is at least one saponin. As used herein, the at least one saponin may comprise a single saponin or a plurality of saponins as a functional ingredient for the composition provided herein. Saponins are glycosidic natural plant products comprising an aglycone ring structure and one or more sugar moieties. Non-limiting examples of specific saponins for use in particular embodiments of the invention include group A acetyl saponin, group B acetyl saponin and group E acetyl saponin. Several common sources of saponins include soybeans, which have approximately 5% saponin content by dry weight, soapwort plants (*Saponaria*), the root of which was used historically as soap, as well as alfalfa, aloe, asparagus, grapes, chickpeas, *yucca*, and various other beans and weeds. Saponins may be obtained from these sources by using extraction techniques well known to those of ordinary skill in the art. A description of conventional extraction techniques can be found in U.S. Pat. Appl. No. 2005/0123662, the disclosure of which is expressly incorporated by reference.

In certain embodiments, the functional ingredient is at least one antioxidant. As used herein "antioxidant" refers to any substance which inhibits, suppresses, or reduces oxidative damage to cells and biomolecules. Examples of suitable antioxidants for embodiments of this invention include, but are not limited to, vitamins, vitamin cofactors, minerals, hormones, carotenoids, carotenoid terpenoids, non-carotenoid terpenoids, flavonoids, flavonoid polyphenolics (e.g., bioflavonoids), flavonols, flavones, phenols, polyphenols, esters of phenols, esters of polyphenols, nonflavonoid phenolics, isothiocyanates, and combinations thereof. In some embodiments, the antioxidant is vitamin A, vitamin C, vitamin E, ubiquinone, mineral selenium, manganese, melatonin, α-carotene, β-carotene, lycopene, lutein, zeanthin, crypoxanthin, reservatol, eugenol, quercetin, catechin, gossypol, hesperetin, curcumin, ferulic acid, thymol, hydroxytyrosol, tumeric, thyme, olive oil, lipoic acid, glutathinone, gutamine, oxalic acid, tocopherol-derived compounds, butylated hydroxyanisole (BHA), butylated hydroxytoluene (BHT), ethylenediaminetetraacetic acid (EDTA), tert-butylhydroquinone, acetic acid, pectin, tocotrienol, tocopherol, coenzyme Q10, zeaxanthin, astaxanthin, canthaxantin, saponins, limonoids, kaempfedrol, myricetin, isorhamnetin, proanthocyanidins, quercetin, rutin, luteolin, apigenin, tangeritin, hesperetin, naringenin, erodictyol, flavan-3-ols (e.g., anthocyanidins), gallocatechins, epicatechin and its gallate forms, epigallocatechin and its gallate forms (ECGC) theaflavin and its gallate forms, thearubigins, isoflavone, phytoestrogens, genistein, daidzein, glycitein, anythocyanins, cyaniding, delphinidin, malvidin, pelargonidin, peonidin, petunidin, ellagic acid, gallic acid, salicylic acid, rosmarinic acid, cinnamic acid and its derivatives (e.g., ferulic acid), chlorogenic acid, chicoric acid, gallotannins, ellagitannins, anthoxanthins, betacyanins and other plant pigments, silymarin, citric acid, lignan, antinutrients, bilirubin, uric acid, R-α-lipoic acid, N-acetylcysteine, emblicanin, apple extract, apple skin extract (applephenon), rooibos extract red, rooibos extract, green, hawthorn berry extract, red raspberry extract, green coffee antioxidant (GCA), *aronia* extract 20%, grape seed extract (VinOseed), cocoa extract, hops extract, mangosteen extract, mangosteen hull extract, cranberry extract, pomegranate extract, pomegranate hull extract, pomegranate seed extract, hawthorn berry extract, pomella pomegranate extract, cinnamon bark extract, grape skin extract, bilberry extract, pine bark extract, pycnogenol, elderberry extract, mulberry root extract, wolfberry (gogi) extract, blackberry extract, blueberry extract, blueberry leaf extract, raspberry extract, turmeric extract, citrus bioflavonoids, black currant, ginger, acai powder, green coffee bean extract, green tea extract, and phytic acid, or combinations thereof. In alternate embodiments, the antioxidant is a synthetic antioxidant such as butylated hydroxytolune or butylated hydroxyanisole, for example. Other sources of suitable antioxidants for embodiments of this invention include, but are not limited to, fruits, vegetables, tea, cocoa, chocolate, spices, herbs, rice, organ meats from livestock, yeast, whole grains or cereal grains.

Particular antioxidants belong to the class of phytonutrients called polyphenols (also known as "polyphenolics"), which are a group of chemical substances found in plants, characterized by the presence of more than one phenol group per molecule. A variety of health benefits may be derived from polyphenols, including prevention of cancer, heart disease, and chronic inflammatory disease and improved mental strength and physical strength, for example. Suitable polyphenols for embodiments of this invention include catechins, proanthocyanidins, procyanidins, anthocyanins, quercerin, rutin, reservatrol, isoflavones, curcumin, punicalagin, ellagitannin, hesperidin, naringin, citrus flavonoids, chlorogenic acid, other similar materials and combinations thereof.

In particular embodiments, the antioxidant is a catechin such as, for example, epigallocatechin gallate (EGCG). In another embodiment, the antioxidant is chosen from proanthocyanidins, procyanidins or combinations thereof. In particular embodiments, the antioxidant is an anthocyanin. In still other embodiments, the antioxidant is chosen from quercetin, rutin or combinations thereof. In yet other embodiments, the antioxidant is reservatrol. In still further embodiments, the antioxidant is an isoflavone. In yet further embodiments, the antioxidant is curcumin. In other embodiments, the antioxidant is chosen from punicalagin, ellagitannin or combinations thereof. In still other embodiments, the antioxidant is chlorogenic acid.

In certain embodiments, the functional ingredient is at least one dietary fiber source. Numerous polymeric carbohydrates having significantly different structures in both composition and linkages fall within the definition of dietary fiber. Such compounds are well known to those skilled in the art, non-limiting examples of which include non-starch polysaccharides, lignin, cellulose, methylcellulose, the hemicelluloses, β-glucans, pectins, gums, mucilage, waxes, inulins, oligosaccharides, fructooligosaccharides, cyclodextrins, chitins and combinations thereof. Although dietary fiber generally is derived from plant sources, indigestible animal products such as chitins are also classified as dietary fiber. Chitin is a polysaccharide composed of units of acetylglucosamine joined by β(1-4) linkages, similar to the linkages of cellulose.

In certain embodiments, the functional ingredient is at least one fatty acid. As used herein, "fatty acid" refers to any straight chain monocarboxylic acid and includes saturated fatty acids, unsaturated fatty acids, long chain fatty acids, medium chain fatty acids, short chain fatty acids, fatty acid precursors (including omega-9 fatty acid precursors), and esterified fatty acids. As used herein, "long chain polyunsaturated fatty acid" refers to any polyunsaturated carboxylic acid or organic acid with a long aliphatic tail. As used herein, "omega-3 fatty acid" refers to any polyunsaturated fatty acid having a first double bond as the third carbon-carbon bond from the terminal methyl end of its carbon chain. In particular embodiments, the omega-3 fatty acid may comprise a long chain omega-3 fatty acid. As used herein, "omega-6 fatty acid" any polyunsaturated fatty acid having a first double bond as the sixth carbon-carbon bond from the terminal methyl end of its carbon chain.

Suitable omega-3 fatty acids for use in embodiments of the present invention can be derived from algae, fish, animals, plants, or combinations thereof, for example. Examples of suitable omega-3 fatty acids include, but are not limited to, linolenic acid, alpha-linolenic acid, eicosapentaenoic acid, docosahexaenoic acid, stearidonic acid, eicosatetraenoic acid and combinations thereof. In some embodiments, suitable omega-3 fatty acids can be provided in fish oils, (e.g., menhaden oil, tuna oil, salmon oil, bonito oil, and cod oil), microalgae omega-3 oils or combinations thereof. In particular embodiments, suitable omega-3 fatty acids may be derived from commercially available omega-3 fatty acid oils such as Microalgae DHA oil (from Martek, Columbia, MD), OmegaPure (from Omega Protein, Houston, TX), Marinol C-38 (from Lipid Nutrition, Channahon, IL), Bonito oil and MEG-3 (from Ocean Nutrition, Dartmouth, NS), Evogel (from Symrise, Holzminden, Germany), Marine Oil, from tuna or salmon (from Arista Wilton, CT), OmegaSource 2000, Marine Oil, from menhaden and Marine Oil, from cod (from OmegaSource, RTP, NC).

Suitable omega-6 fatty acids include, but are not limited to, linoleic acid, gamma-linolenic acid, dihommo-gamma-linolenic acid, arachidonic acid, eicosadienoic acid, docosadienoic acid, adrenic acid, docosapentaenoic acid and combinations thereof.

Suitable esterified fatty acids for embodiments of the present invention may include, but are not limited to, monoacylglycerols containing omega-3 and/or omega-6 fatty acids, diacylglycerols containing omega-3 and/or omega-6 fatty acids, or triacylglycerols containing omega-3 and/or omega-6 fatty acids and combinations thereof.

In certain embodiments, the functional ingredient is at least one vitamin. Suitable vitamins include vitamin A, vitamin D, vitamin E, vitamin K, vitamin B1, vitamin B2, vitamin B3, vitamin B5, vitamin B6, vitamin B7, vitamin B9, vitamin B12, and vitamin C.

Various other compounds have been classified as vitamins by some authorities. These compounds may be termed pseudo-vitamins and include, but are not limited to, compounds such as ubiquinone (coenzyme Q10), pangamic acid, dimethylglycine, taestrile, amygdaline, flavanoids, para-aminobenzoic acid, adenine, adenylic acid, and s-methyl-methionine. As used herein, the term vitamin includes pseudo-vitamins. In some embodiments, the vitamin is a fat-soluble vitamin chosen from vitamin A, D, E, K and combinations thereof. In other embodiments, the vitamin is a water-soluble vitamin chosen from vitamin B1, vitamin B2, vitamin B3, vitamin B6, vitamin B12, folic acid, biotin, pantothenic acid, vitamin C and combinations thereof.

In certain embodiments, the functional ingredient is glucosamine, optionally further comprising chondroitin sulfate.

In certain embodiments, the functional ingredient is at least one mineral. Minerals, in accordance with the teachings of this invention, comprise inorganic chemical elements required by living organisms. Minerals are comprised of a broad range of compositions (e.g., elements, simple salts, and complex silicates) and also vary broadly in crystalline structure. They may naturally occur in foods and beverages, may be added as a supplement, or may be consumed or administered separately from foods or beverages.

Minerals may be categorized as either bulk minerals, which are required in relatively large amounts, or trace minerals, which are required in relatively small amounts. Bulk minerals generally are required in amounts greater than or equal to about 100 mg per day and trace minerals are those that are required in amounts less than about 100 mg per day.

In one embodiment, the mineral is chosen from bulk minerals, trace minerals or combinations thereof. Non-limiting examples of bulk minerals include calcium, chlorine, magnesium, phosphorous, potassium, sodium, and sulfur. Non-limiting examples of trace minerals include chromium, cobalt, copper, fluorine, iron, manganese, molybdenum, selenium, zinc, and iodine. Although iodine generally is classified as a trace mineral, it is required in larger quantities than other trace minerals and often is categorized as a bulk mineral.

In a particular embodiment, the mineral is a trace mineral, believed to be necessary for human nutrition, non-limiting examples of which include bismuth, boron, lithium, nickel, rubidium, silicon, strontium, tellurium, tin, titanium, tungsten, and vanadium.

The minerals embodied herein may be in any form known to those of ordinary skill in the art. For example, in a particular embodiment the minerals may be in their ionic form, having either a positive or negative charge. In another particular embodiment the minerals may be in their molecular form. For example, sulfur and phosphorous often are found naturally as sulfates, sulfides, and phosphates.

In certain embodiments, the functional ingredient is at least one preservative. In particular embodiments of this invention, the preservative is chosen from antimicrobials, antioxidants, antienzymatics or combinations thereof. Non-limiting examples of antimicrobials include sulfites, propionates, benzoates, sorbates, nitrates, nitrites, bacteriocins, salts, sugars, acetic acid, dimethyl dicarbonate (DMDC), ethanol, and ozone. In one embodiment, the preservative is a sulfite. Sulfites include, but are not limited to, sulfur dioxide, sodium bisulfite, and potassium hydrogen sulfite. In another embodiment, the preservative is a propionate. Propionates include, but are not limited to, propionic acid, calcium propionate, and sodium propionate. In yet another embodiment, the preservative is a benzoate. Benzoates include, but are not limited to, sodium benzoate and benzoic acid. In a still further embodiment, the preservative is a sorbate. Sorbates include, but are not limited to, potassium sorbate, sodium sorbate, calcium sorbate, and sorbic acid. In a yet further embodiment, the preservative is a nitrate and/or a nitrite. Nitrates and nitrites include, but are not limited to, sodium nitrate and sodium nitrite. In another embodiment, the at least one preservative is a bacteriocin, such as, for example, nisin. In a further embodiment, the preservative is ethanol. In still another embodiment, the preservative is ozone. Non-limiting examples of antienzymatics suitable for use as preservatives in particular embodiments of the invention include ascorbic acid, citric acid, and metal chelating agents such as ethylenediaminetetraacetic acid (EDTA).

In certain embodiments, the functional ingredient is at least one hydration agent. In a particular embodiment, the hydration agent is an electrolyte. Non-limiting examples of electrolytes include sodium, potassium, calcium, magnesium, chloride, phosphate, bicarbonate, and combinations thereof. Suitable electrolytes for use in particular embodiments of this invention are also described in U.S. Pat. No. 5,681,569, the disclosure of which is expressly incorporated herein by reference. In one embodiment, the electrolyte is obtained from their corresponding water-soluble salt. Non-limiting examples of salts for use in particular embodiments include chlorides, carbonates, sulfates, acetates, bicarbonates, citrates, phosphates, hydrogen phosphates, tartrates, sorbates, citrates, benzoates, or combinations thereof. In other embodiments, the electrolytes are provided by juice, fruit extracts, vegetable extracts, tea, or teas extracts.

In particular embodiments of this invention, the hydration agent is a carbohydrate to supplement energy stores burned by muscles. Suitable carbohydrates for use in particular embodiments of this invention are described in U.S. Pat. Nos. 4,312,856, 4,853,237, 5,681,569, and 6,989,171, the disclosures of which are expressly incorporated herein by reference. Non-limiting examples of suitable carbohydrates include monosaccharides, disaccharides, oligosaccharides, complex polysaccharides or combinations thereof. Non-limiting examples of suitable types of monosaccharides for use in particular embodiments include trioses, tetroses, pentoses, hexoses, heptoses, octoses, and nonoses. Non-limiting examples of specific types of suitable monosaccharides include glyceraldehyde, dihydroxyacetone, erythrose, threose, erythrulose, arabinose, lyxose, ribose, xylose, ribulose, xylulose, allose, altrose, galactose, glucose, gulose, idose, mannose, talose, fructose, psicose, sorbose, tagatose, mannoheptulose, sedoheltulose, octolose, and sialose. Non-limiting examples of suitable disaccharides include sucrose, lactose, and maltose. Non-limiting examples of suitable oligosaccharides include saccharose, maltotriose, and maltodextrin. In other particular embodiments, the carbohydrates are provided by a corn syrup, a beet sugar, a cane sugar, a juice, or a tea.

In another particular embodiment, the hydration agent is a flavanol that provides cellular rehydration. Flavanols are a class of natural substances present in plants, and generally comprise a 2-phenylbenzopyrone molecular skeleton attached to one or more chemical moieties. Non-limiting examples of suitable flavanols for use in particular embodiments of this invention include catechin, epicatechin, gallocatechin, epigallocatechin, epicatechin gallate, epigallocatechin 3-gallate, theaflavin, theaflavin 3-gallate, theaflavin 3'-gallate, theaflavin 3,3' gallate, thearubigin or combinations thereof. Several common sources of flavanols include tea plants, fruits, vegetables, and flowers. In preferred embodiments, the flavanol is extracted from green tea.

In a particular embodiment, the hydration agent is a glycerol solution to enhance exercise endurance. The ingestion of a glycerol containing solution has been shown to provide beneficial physiological effects, such as expanded blood volume, lower heart rate, and lower rectal temperature.

In certain embodiments, the functional ingredient is chosen from at least one probiotic, prebiotic and combination thereof. The probiotic is a beneficial microorganisms that affects the human body's naturally-occurring gastrointestinal microflora. Examples of probiotics include, but are not limited to, bacteria of the genus Lactobacilli, Bifidobacteria, Streptococci, or combinations thereof, that confer beneficial effects to humans. In particular embodiments of the invention, the at least one probiotic is chosen from the genus Lactobacilli. According to other particular embodiments of this invention, the probiotic is chosen from the genus Bifidobacteria. According to still other particular embodiments of this invention, the probiotic is chosen from the genus *Streptococcus*.

Probiotics that may be used in accordance with this invention are well-known to those of skill in the art. Non-limiting examples of foodstuffs comprising probiotics include yogurt, sauerkraut, kefir, kimchi, fermented vegetables, and other foodstuffs containing a microbial element that beneficially affects the host animal by improving the intestinal microbalance.

Prebiotics, in accordance with the teachings of this invention, include, without limitation, mucopolysaccharides, oligosaccharides, polysaccharides, amino acids, vitamins, nutrient precursors, proteins and combinations thereof. According to a particular embodiment of this invention, the prebiotic is chosen from dietary fibers, including, without limitation, polysaccharides and oligosaccharides. Non-limiting examples of oligosaccharides that are categorized as prebiotics in accordance with particular embodiments of this invention include fructooligosaccharides, inulins, isomaltooligosaccharides, lactitol, lactosucrose, lactulose, pyrodextrins, soy oligosaccharides, transgalacto-oligosaccharides, and xylo-oligosaccharides. In other embodiments, the prebiotic is an amino acid. Although a number of known prebiotics break down to provide carbohydrates for probiotics, some probiotics also require amino acids for nourishment.

Prebiotics are found naturally in a variety of foods including, without limitation, bananas, berries, asparagus, garlic, wheat, oats, barley (and other whole grains), flaxseed, tomatoes, Jerusalem artichoke, onions and chicory, greens (e.g., dandelion greens, spinach, collard greens, chard, kale, mustard greens, turnip greens), and legumes (e.g., lentils, kidney beans, chickpeas, navy beans, white beans, black beans).

In certain embodiments, the functional ingredient is at least one weight management agent.

As used herein, "a weight management agent" includes an appetite suppressant and/or a thermogenesis agent. As used herein, the phrases "appetite suppressant", "appetite satiation compositions", "satiety agents", and "satiety ingredients" are synonymous. The phrase "appetite suppressant" describes macronutrients, herbal extracts, exogenous hormones, anorectics, anorexigenics, pharmaceutical drugs, and combinations thereof, that when delivered in an effective amount, suppress, inhibit, reduce, or otherwise curtail a person's appetite. The phrase "thermogenesis agent" describes macronutrients, herbal extracts, exogenous hormones, anorectics, anorexigenics, pharmaceutical drugs, and combinations thereof, that when delivered in an effective amount, activate or otherwise enhance a person's thermogenesis or metabolism.

Suitable weight management agents include macronutrient selected from the group consisting of proteins, carbohydrates, dietary fats, and combinations thereof. Consumption of proteins, carbohydrates, and dietary fats stimulates the release of peptides with appetite-suppressing effects. For example, consumption of proteins and dietary fats stimulates the release of the gut hormone cholecytokinin (CCK), while consumption of carbohydrates and dietary fats stimulates release of Glucagon-like peptide 1 (GLP-1).

Suitable macronutrient weight management agents also include carbohydrates. Carbohydrates generally comprise sugars, starches, cellulose and gums that the body converts into glucose for energy. Carbohydrates often are classified into two categories, digestible carbohydrates (e.g., monosaccharides, disaccharides, and starch) and non-digestible carbohydrates (e.g., dietary fiber). Studies have shown that non-digestible carbohydrates and complex polymeric carbohydrates having reduced absorption and digestibility in the small intestine stimulate physiologic responses that inhibit food intake. Accordingly, the carbohydrates embodied herein desirably comprise non-digestible carbohydrates or carbohydrates with reduced digestibility. Non-limiting examples of such carbohydrates include polydextrose; inulin; monosaccharide-derived polyols such as erythritol, mannitol, xylitol, and sorbitol; disaccharide-derived alcohols such as isomalt, lactitol, and maltitol; and hydrogenated starch hydrolysates. Carbohydrates are described in more detail herein below.

In another particular embodiment weight management agent is a dietary fat. Dietary fats are lipids comprising combinations of saturated and unsaturated fatty acids. Poly-unsaturated fatty acids have been shown to have a greater satiating power than mono-unsaturated fatty acids. Accordingly, the dietary fats embodied herein desirably comprise poly-unsaturated fatty acids, non-limiting examples of which include triacylglycerols.

In a particular embodiment, the weight management agent is an herbal extract. Extracts from numerous types of plants have been identified as possessing appetite suppressant properties. Non-limiting examples of plants whose extracts have appetite suppressant properties include plants of the genus *Hoodia, Trichocaulon, Caralluma, Stapelia, Orbea, Asclepias*, and *Camelia*. Other embodiments include extracts derived from *Gymnema Sylvestre*, Kola Nut, Citrus Auran *Tium*, Yerba Mate, *Griffonia Simplicifolia*, guarana, myrrh, guggul Lipid, and black current seed oil.

The herbal extracts may be prepared from any type of plant material or plant biomass. Non-limiting examples of plant material and biomass include the stems, roots, leaves, dried powder obtained from the plant material, and sap or dried sap. The herbal extracts generally are prepared by extracting sap from the plant and then spray-drying the sap. Alternatively, solvent extraction procedures may be employed. Following the initial extraction, it may be desirable to further fractionate the initial extract (e.g., by column chromatography) in order to obtain an herbal extract with enhanced activity. Such techniques are well known to those of ordinary skill in the art.

In a particular embodiment, the herbal extract is derived from a plant of the genus *Hoodia*, species of which include *H. alstonii, H. currorii, H. dregei, H. flava, H. gordonii, H. jutatae, H. mossamedensis, H. officinalis, H.* parviflorai, *H. pedicellata, H. pilifera, H. ruschii,* and *H. triebneri. Hoodia* plants are stem succulents native to southern Africa. A sterol glycoside of *Hoodia*, known as P57, is believed to be responsible for the appetite-suppressant effect of the *Hoodia* species. In another particular embodiment, the herbal extract is derived from a plant of the genus *Caralluma*, species of which include *C. indica, C. fimbriata, C. attenuate, C. tuberculata, C.* edulis, *C. adscendens, C. stalagmifera, C. umbellate, C. penicillata, C. russeliana, C. retrospicens, C. Arabica*, and *C. lasiantha*. Carralluma plants belong to the same Subfamily as *Hoodia*, Asclepiadaceae. *Caralluma* are small, erect and fleshy plants native to India having medicinal properties, such as appetite suppression, that generally are attributed to glycosides belonging to the pregnane group of glycosides, non-limiting examples of which include caratuberside A, caratuberside B, bouceroside I, bouceroside II, bouceroside III, bouceroside IV, bouceroside V, bouceroside VI, bouceroside VII, bouceroside VIII, bouceroside IX, and bouceroside X. In another particular embodiment, the at least one herbal extract is derived from a plant of the genus *Trichocaulon*. *Trichocaulon* plants are succulents that generally are native to southern Africa, similar to *Hoodia*, and include the species *T. piliferum* and *T. officinale*. In another particular embodiment, the herbal extract is derived from a plant of the genus *Stapelia* or *Orbea*, species of which include *S. gigantean* and O. variegate, respectively. Both *Stapelia* and *Orbea* plants belong to the same Subfamily as *Hoodia*, Asclepiadaceae. Not wishing to be bound by any theory, it is believed that the compounds exhibiting appetite suppressant activity are saponins, such as pregnane glycosides, which include stavarosides A, B, C, D, E, F, G, H, I, J, and K. In another particular embodiment, the herbal extract is derived from a plant of the genus *Asclepias*. *Asclepias* plants also belong to the Asclepiadaceae family of plants. Non-limiting examples of *Asclepias* plants include A. incarnate, A. curassayica, *A. syriaca*, and *A. tuberose*. Not wishing to be bound by any theory, it is believed that the extracts comprise steroidal compounds, such as pregnane glycosides and pregnane aglycone, having appetite suppressant effects.

In a particular embodiment, the weight management agent is an exogenous hormone having a weight management effect. Non-limiting examples of such hormones include CCK, peptide YY, ghrelin, bombesin and gastrin-releasing peptide (GRP), enterostatin, apolipoprotein A-IV, GLP-1, amylin, somastatin, and leptin.

In another embodiment, the weight management agent is a pharmaceutical drug. Non-limiting examples include phentenime, diethylpropion, phendimetrazine, sibutramine, rimonabant, oxyntomodulin, floxetine hydrochloride, ephedrine, phenethylamine, or other stimulants.

In certain embodiments, the functional ingredient is at least one osteoporosis management agent. In certain embodiments, the osteoporosis management agent is at least one calcium source. According to a particular embodiment, the calcium source is any compound containing calcium, including salt complexes, solubilized species, and other forms of calcium. Non-limiting examples of calcium sources include amino acid chelated calcium, calcium carbonate, calcium oxide, calcium hydroxide, calcium sulfate, calcium chloride, calcium phosphate, calcium hydrogen phosphate, calcium dihydrogen phosphate, calcium citrate, calcium malate, calcium citrate malate, calcium gluconate, calcium tartrate, calcium lactate, solubilized species thereof, and combinations thereof.

According to a particular embodiment, the osteoporosis management agent is a magnesium source. The magnesium source is any compound containing magnesium, including salt complexes, solubilized species, and other forms of magnesium. Non-limiting examples of magnesium sources include magnesium chloride, magnesium citrate, magnesium gluceptate, magnesium gluconate, magnesium lactate, magnesium hydroxide, magnesium picolate, magnesium sulfate, solubilized species thereof, and mixtures thereof. In another particular embodiment, the magnesium source comprises an amino acid chelated or creatine chelated magnesium.

In other embodiments, the osteoporosis agent is chosen from vitamins D, C, K, their precursors and/or beta-carotene and combinations thereof.

Numerous plants and plant extracts also have been identified as being effective in the prevention and treatment of osteoporosis. Non-limiting examples of suitable plants and plant extracts as osteoporosis management agents include species of the genus *Taraxacum* and *Amelanchier*, as disclosed in U.S. Patent Publication No. 2005/0106215, and species of the genus *Lindera, Artemisia, Acorus, Carthamus, Carum, Cnidium, Curcuma, Cyperus, Juniperus, Prunus, Iris, Cichorium, Dodonaea, Epimedium,* Erigonoum, *Soya, Mentha, Ocimum,* thymus, *Tanacetum, Plantago,* Spearmint, *Bixa, Vitis, Rosemarinus, Rhus,* and *Anethum,* as disclosed in U.S. Patent Publication No. 2005/0079232.

In certain embodiments, the functional ingredient is at least one phytoestrogen. Phytoestrogens are compounds found in plants which can typically be delivered into human bodies by ingestion of the plants or the plant parts having the phytoestrogens. As used herein, "phytoestrogen" refers to any substance which, when introduced into a body causes an estrogen-like effect of any degree. For example, a phytoestrogen may bind to estrogen receptors within the body and have a small estrogen-like effect. Examples of suitable phytoestrogens for embodiments of this invention include, but are not limited to, isoflavones, stilbenes, lignans, resorcyclic acid lactones, coumestans, coumestrol, equol, and combinations thereof. Sources of suitable phytoestrogens include, but are not limited to, whole grains, cereals, fibers, fruits, vegetables, black cohosh, agave root, black currant, black haw, chasteberries, cramp bark, dong quai root, devil's club root, false unicorn root, *ginseng* root, groundsel herb, licorice, liferoot herb, motherwort herb, peony root, raspberry leaves, rose family plants, sage leaves, sarsaparilla root, saw palmetto berried, wild yam root, yarrow blossoms, legumes, soybeans, soy products (e.g., miso, soy flour, soymilk, soy nuts, soy protein isolate, tempeh, or tofu) chick peas, nuts, lentils, seeds, clover, red clover, dandelion leaves, dandelion roots, fenugreek seeds, green tea, hops, red wine, flaxseed, garlic, onions, linseed, borage, butterfly weed, caraway, chaste tree, vitex, dates, dill, fennel seed, gotu kola, milk thistle, pennyroyal, pomegranates, southernwood, soya flour, tansy, and root of the kudzu vine (*pueraria* root) and the like, and combinations thereof.

Isoflavones belong to the group of phytonutrients called polyphenols. In general, polyphenols (also known as "polyphenolics"), are a group of chemical substances found in plants, characterized by the presence of more than one phenol group per molecule.

Suitable phytoestrogen isoflavones in accordance with embodiments of this invention include genistein, daidzein, glycitein, biochanin A, formononetin, their respective naturally occurring glycosides and glycoside conjugates, matairesinol, secoisolariciresinol, enterolactone, enterodiol, textured vegetable protein, and combinations thereof.

Suitable sources of isoflavones for embodiments of this invention include, but are not limited to, soy beans, soy products, legumes, alfalfa sprouts, chickpeas, peanuts, and red clover.

In certain embodiments, the functional ingredient is at least one long chain primary aliphatic saturated alcohol. Long-chain primary aliphatic saturated alcohols are a diverse group of organic compounds. The term alcohol refers to the fact these compounds feature a hydroxyl group (—OH) bound to a carbon atom. Non-limiting examples of particular long-chain primary aliphatic saturated alcohols for use in particular embodiments of the invention include the 8 carbon atom 1-octanol, the 9 carbon 1-nonanol, the 10 carbon atom 1-decanol, the 12 carbon atom 1-dodecanol, the 14 carbon atom 1-tetradecanol, the 16 carbon atom 1-hexadecanol, the 18 carbon atom 1-octadecanol, the 20 carbon atom 1-eicosanol, the 22 carbon 1-docosanol, the 24 carbon 1-tetracosanol, the 26 carbon 1-hexacosanol, the 27 carbon 1-heptacosanol, the 28 carbon 1-octanosol, the 29 carbon 1-nonacosanol, the 30 carbon 1-triacontanol, the 32 carbon 1-dotriacontanol, and the 34 carbon 1-tetracontanol.

In a particularly desirable embodiment of the invention, the long-chain primary aliphatic saturated alcohols are policosanol. Policosanol is the term for a mixture of long-chain primary aliphatic saturated alcohols composed primarily of 28 carbon 1-octanosol and 30 carbon 1-triacontanol, as well as other alcohols in lower concentrations such as 22 carbon 1-docosanol, 24 carbon 1-tetracosanol, 26 carbon 1-hexacosanol, 27 carbon 1-heptacosanol, 29 carbon 1-nonacosanol, 32 carbon 1-dotriacontanol, and 34 carbon 1-tetracontanol.

In certain embodiments, the functional ingredient is at least one phytosterol, phytostanol or combination thereof. As used herein, the phrases "stanol", "plant stanol" and "phytostanol" are synonymous. Plant sterols and stanols are present naturally in small quantities in many fruits, vegetables, nuts, seeds, cereals, legumes, vegetable oils, bark of the trees and other plant sources. Sterols are a subgroup of steroids with a hydroxyl group at C-3. Generally, phytosterols have a double bond within the steroid nucleus, like cholesterol; however, phytosterols also may comprise a substituted side chain (R) at C-24, such as an ethyl or methyl group, or an additional double bond. The structures of phytosterols are well known to those of skill in the art.

At least 44 naturally-occurring phytosterols have been discovered, and generally are derived from plants, such as corn, soy, wheat, and wood oils; however, they also may be produced synthetically to form compositions identical to those in nature or having properties similar to those of naturally-occurring phytosterols. According to particular embodiments of this invention, non-limiting examples of phytosterols well known to those or ordinary skill in the art include 4-desmethylsterols (e.g., β-sitosterol, campesterol, stigmasterol, brassicasterol, 22-dehydrobrassicasterol, and Δ5-avenasterol), 4-monomethyl sterols, and 4,4-dimethyl sterols (triterpene alcohols) (e.g., cycloartenol, 24-methylenecycloartanol, and cyclobranol).

As used herein, the phrases "stanol", "plant stanol" and "phytostanol" are synonymous. Phytostanols are saturated sterol alcohols present in only trace amounts in nature and also may be synthetically produced, such as by hydrogenation of phytosterols. According to particular embodiments of this invention, non-limiting examples of phytostanols include β-sitostanol, campestanol, cycloartanol, and saturated forms of other triterpene alcohols.

Both phytosterols and phytostanols, as used herein, include the various isomers such as the α and β isomers (e.g., α-sitosterol and β-sitostanol, which comprise one of the most effective phytosterols and phytostanols, respectively, for lowering serum cholesterol in mammals).

The phytosterols and phytostanols of the present invention also may be in their ester form. Suitable methods for deriving the esters of phytosterols and phytostanols are well known to those of ordinary skill in the art, and are disclosed in U.S. Pat. Nos. 6,589,588, 6,635,774, 6,800,317, and U.S. Patent Publication Number 2003/0045473, the disclosures of which are incorporated herein by reference in their entirety. Non-limiting examples of suitable phytosterol and phytostanol esters include sitosterol acetate, sitosterol oleate, stigmasterol oleate, and their corresponding phytostanol esters. The phytosterols and phytostanols of the present invention also may include their derivatives.

Generally, the amount of functional ingredient in the composition varies widely depending on the particular composition and the desired functional ingredient. Those of ordinary skill in the art will readily ascertain the appropriate amount of functional ingredient for each composition.

In one embodiment, a method for preparing a composition comprises combining at least one mogroside of the present invention and at least one sweetener and/or additive and/or functional ingredient.

In a particular embodiment, a method for preparing a composition comprises combining at least one mogroside of the present invention and at least one additional sweetener and/or additive and/or functional ingredient.

In a particular embodiment, a method for preparing a composition comprises combining at least one mogroside of the present invention and at least one sweetener and/or additive and/or functional ingredient, wherein the at least one sweetener and/or additive and/or functional ingredient does not exist with (is not admixed with) the at least one mogroside in nature, and the composition provides a more sucrose-like taste profile compared to the mogroside in nature and (if applicable) the at least one sweetener and/or additive and/or functional ingredient in nature. For example, in certain embodiments the composition exhibits one or more of the following characteristics: improved sweetness potency, improved mouthfeel, decreased sweetness linger, decreased bitterness and/or decreased metallic taste.

Consumables

In one embodiment, the present invention is a consumable comprising at least one mogroside of the present invention, or a composition comprising at least one mogroside of the present invention. In a particular embodiment, the at least one mogroside is isolated and purified.

The mogroside(s) of the present invention, or a composition comprising the same, can be admixed with any known edible or oral composition, referred to herein as a "consumable". Consumables, as used herein, mean substances which are contacted with the mouth of man or animal, including substances which are taken into and subsequently ejected from the mouth and substances which are drunk, eaten, swallowed or otherwise ingested, and are safe for human or animal consumption when used in a generally acceptable range.

Exemplary consumables include pharmaceutical compositions, edible gel mixes and compositions, dental compositions, foodstuffs (confections, condiments, chewing gum, cereal compositions baked goods dairy products, and table-top sweetener compositions) beverages and beverage products. The consumables of the present invention require admixing and, as such, do not occur in nature.

For example, a beverage is a consumable. The beverage may be sweetened or unsweetened. The mogroside(s) of the present invention, or a composition comprising the same, may be added to a beverage or beverage matrix to sweeten the beverage or enhance its existing sweetness or flavor.

In one embodiment, the present invention is a consumable comprising at least one mogroside of the present invention. In particular embodiments, a mogroside of the present invention is present in the consumable in a concentration greater than about 1 ppm, such as, for example, from about 1 ppm to about 1,000 ppm, from about 25 ppm to about 1,000 ppm, from about 50 ppm to about 1,000 ppm, from about 75 ppm to about 1,000 ppm, from about 100 ppm to about 1,000 ppm, from about 200 ppm to about 1,000 ppm, from about 300 ppm to about 1,000 ppm, from about 400 ppm to about 1,000 ppm, from about 500 ppm to about 1,000 ppm or from about 50 ppm to about 600 ppm.

In other particular embodiments, a mogroside of the present invention is present in the consumable in a purity of at least about 5% with respect to a mixture of mogrosides or Luo Han Guo extract, such as, for example, at least about 10%, at least about 20%, at least about 30%, at least about 40%, at least about 50%, at least about 60%, at least about 70%, at least about 80%, at least about 90%, at least about 95% or at least about 97%. In still other embodiments, a mogroside of the present invention is present in the consumable in >99% purity.

The consumable can optionally include additives, additional sweeteners, functional ingredients and combinations thereof, as described herein. Any of the additive, additional sweetener and functional ingredients described above can be present in the consumable.

In exemplary embodiments, a consumable comprising at least one isolated and purified mogroside of the present invention has about 30% or more sweetness compared to a corresponding consumable comprising partially purified mogroside or Luo Han Guo extract, such as, for example, about 40% or more, about 50% or more, about 60% or more, about 70% or more, about 80% or more or about 90% or more.

In other exemplary embodiments, a consumable comprising at least one isolated and purified mogroside of the present invention has at least about 30% less bitterness (the taste stimulated by certain substances such as quinine, caffeine and sucrose octa-acetate) compared to a corresponding consumable comprising partially purified mogroside or Luo Han Guo extract, such as, for example, at least about 40%, at least about 50%, at least about 60%, at least about 70%, at least about 80% or at least about 90%. In a particular embodiment, a consumable comprising at least one isolated and purified mogroside of the present invention has substantially no bitterness. Methods of measuring bitterness of a compound are known in the art In still other exemplary embodiments, a consumable comprising at least one isolated and purified mogroside of the present invention has at least about 30% less sweet lingering aftertaste (the intensity of the sweet taste after expectoration) compared to a corresponding consumable comprising partially purified mogroside or Luo Han Guo extract, such as, for example, at least about 50%, at least about 60%, at least about 70%, at least about 80% or at least about 90%. In a particular embodiment, a consumable comprising at least one isolated and purified mogroside of the present invention has substantially no sweet lingering aftertaste. Methods of measuring sweet lingering aftertaste are known in the art.

In yet other exemplary embodiments, a consumable comprising at least one isolated and purified mogroside of the present invention has at least about 30% less metallic taste (taste associated with metals, tinny or iron) compared to a corresponding consumable comprising partially purified mogroside or Luo Han Guo extract, such as, for example, at least about 50%, at least about 60%, at least about 70%, at least about 80% or at least about 90%. In a particular embodiment, a consumable comprising at least one isolated and purified mogroside of the present invention has substantially no metallic taste.

In exemplary embodiments, a consumable comprising at least one isolated and purified mogroside of the present invention exhibits a maximal response (maximum sweetness (% SE) achieved with increasing concentration of compound) that is at least about 30% greater compared to a corresponding consumable comprising partially purified mogroside or Luo Han Guo extract, such as, for example, at least about 40% greater, at least about 50% greater, at least about 60% greater, at least about 70% greater, at least about 80% greater or at least about 90% greater. Methods of measuring the maximal response of a compound are known in the art.

In other exemplary embodiments, a consumable comprising at least one isolated and purified mogroside of the present invention exhibits a sweetness onset (the time until maximum sweetness is experienced) that is at least about 30% shorter than a consumable comprising partially purified mogroside or Luo Han Guo extract, such as, for example, at least about 40% short, at least about 50% shorter, at least about 60% shorter, at least about 70% shorter, at least about 80% shorter or at least about 90% shorter. Methods of measuring sweetness onset are known in the art.

In another embodiment, the present invention is a beverage or beverage product comprising a composition that comprises at least one mogroside of the present invention. In a particular embodiment, the beverage or beverage product comprises a composition comprising at least one isolated and purified mogroside of the present invention.

As used herein a "beverage product" is a ready-to-drink beverage, a beverage concentrate, a beverage syrup, or a powdered beverage. Suitable ready-to-drink beverages include carbonated and non-carbonated beverages. Carbonated beverages include, but are not limited to, frozen carbonated beverages, enhanced sparkling beverages, cola, lemon-lime flavored sparkling beverage, orange flavored sparkling beverage, grape flavored sparkling beverage, strawberry flavored sparkling beverage, pineapple flavored sparkling beverage, ginger-ale, soft drinks and root beer. Non-carbonated beverages include, but are not limited to fruit juice, fruit-flavored juice, juice drinks, nectars, vegetable juice, vegetable-flavored juice, sports drinks, energy drinks, enhanced water drinks, enhanced water with vitamins, near water drinks (e.g., water with natural or synthetic flavorants), coconut water, tea type drinks (e.g. black tea, green tea, red tea, oolong tea), coffee, cocoa drink, beverage containing milk components (e.g. milk beverages, coffee containing milk components, café au lait, milk tea, fruit milk beverages), beverages containing cereal extracts, smoothies and combinations thereof.

Beverage concentrates and beverage syrups are prepared with an initial volume of liquid matrix (e.g. water) and the desired beverage ingredients. Full strength beverages are then prepared by adding further volumes of water. Powdered beverages are prepared by dry-mixing all of the beverage ingredients in the absence of a liquid matrix. Full strength beverages are then prepared by adding the full volume of water.

Beverages comprise a matrix, i.e. the basic ingredient in which the ingredients—including the compositions of the present invention—are dissolved. In one embodiment, a beverage comprises water of beverage quality as the matrix, such as, for example deionized water, distilled water, reverse osmosis water, carbon-treated water, purified water, demineralized water and combinations thereof, can be used. Additional suitable matrices include, but are not limited to phosphoric acid, phosphate buffer, citric acid, citrate buffer and carbon-treated water.

In one embodiment, the present invention is a beverage comprising at least one mogroside of the present invention.

In a further embodiment, the present invention is a beverage product comprising at least one mogroside of the present invention.

The at least one mogroside can be provided as a single compound or as part of any composition described above. In an exemplary embodiment, the at least one mogroside is isolated and purified.

In a particular embodiment, a beverage or beverage product comprises at least one mogroside of the present invention in isolated and purified form and at least one other substance that does not occur with the mogroside in nature. In one embodiment, the at least other additional substance modulates the taste profile of the at least one mogroside to provide a beverage with a more sucrose-like taste profile compared to the mogroside in nature and (if applicable) the at least one other substance in nature. For example, in certain embodiments the beverage exhibits one or more of the following characteristics: improved sweetness potency, improved mouthfeel, decreased sweetness linger, decreased bitterness and/or decreased metallic taste.

The concentration of the mogroside of the present invention in the beverage may be above, at or below the threshold sweetness or flavor recognition concentration of the mogroside of the present invention. In a particular embodiment wherein the mogroside is acting as a sweetener, the mogroside is present in a concentration at or above the threshold sweetness concentration.

In one embodiment, a mogroside of the present invention is present in the beverage in a concentration greater than about 1 ppm, such as, for example, from about 1 ppm to about 1,000 ppm, from about 25 ppm to about 1,000 ppm, from about 50 ppm to about 1,000 ppm, from about 75 ppm to about 1,000 ppm, from about 100 ppm to about 1,000 ppm, from about 200 ppm to about 1,000 ppm, from about 300 ppm to about 1,000 ppm, from about 400 ppm to about 1,000 ppm or from about 500 ppm to about 1,000 ppm.

In a more particular embodiment, a mogroside of the present invention is present in the beverage in a concentration from about 25 ppm to about 600 ppm, such as, for example, from about 25 ppm to about 500 ppm, from about 25 ppm to about 400 ppm, from about 25 ppm to about 300 ppm, from about 25 ppm to about 200 ppm, from about 25 ppm to about 100 ppm, from about 50 ppm to about 600 ppm, from about 50 ppm to about 500 ppm, from about 50 ppm to about 400 ppm, from about 50 ppm to about 300 ppm, from about 50 ppm to about 200 ppm, from about 50 ppm to about 100 ppm, from about 100 ppm to about 600 ppm, from about 100 ppm to about 500 ppm, from about 100 ppm to about 400 ppm, from about 100 ppm to about 300 ppm, from about 100 ppm to about 200 ppm, from about 200 ppm to about 600 ppm, from about 200 ppm to about 500 ppm, from about 200 ppm to about 400 ppm, from about 200 ppm to about 300 ppm, from about 300 ppm to about 600 ppm, from about 300 ppm to about 500 ppm, from about 300 ppm to about 400 ppm, from about 400 ppm to about 600 ppm, from about 400 ppm to about 500 ppm or from about 500 ppm to about 600 ppm.

In other particular embodiments, a mogroside of the present invention is present in the beverage in a purity of at least about 5% with respect to a mixture of mogrosides or Luo Han Guo extract, such as, for example, at least about 10%, at least about 20%, at least about 30%, at least about 40%, at least about 50%, at least about 60%, at least about 70%, at least about 80%, at least about 90%, at least about 95% or at least about 97%. In still other embodiments, a mogroside of the present invention is present in the beverage in >99% purity.

The beverage can include one or more sweeteners. Any of the sweeteners detailed herein can be used, including natural, non-natural, or synthetic sweeteners. These may be added to the beverage either before, contemporaneously with or after the mogroside(s) of the present invention.

The consumable can optionally include additives, functional ingredients and combinations thereof, as described herein. Any of the additives and functional ingredients described above can be present in the consumable. In certain embodiments, the additive and/or functional ingredient modulates the taste profile of the at least one mogroside to provide a composition with a more sucrose-like taste profile compared to the mogroside in nature and (if applicable) the additive and/or functional ingredient in nature. For example, in certain embodiments the composition exhibits one or more of the following characteristics: improved sweetness potency, improved mouthfeel, decreased sweetness linger, decreased bitterness and/or decreased metallic taste.

It is contemplated that the pH of the consumable, such as, for example, a beverage, does not materially or adversely affect the taste of the sweetener. A non-limiting example of the pH range of the beverage may be from about 1.8 to about 10. A further example includes a pH range from about 2 to about 5. In a particular embodiment, the pH of beverage can be from about 2.5 to about 4.2. On of skill in the art will understand that the pH of the beverage can vary based on the type of beverage. Dairy beverages, for example, can have pHs greater than 4.2.

The titratable acidity of a beverage may, for example, range from about 0.01 to about 1.0% by weight of beverage.

In one embodiment, the sparkling beverage product has an acidity from about 0.01 to about 1.0% by weight of the beverage, such as, for example, from about 0.05% to about 0.25% by weight of beverage.

The carbonation of a sparkling beverage product has 0 to about 2% (w/w) of carbon dioxide or its equivalent, for example, from about 0.1 to about 1.0% (w/w).

The temperature of a beverage may, for example, range from about 4° C. to about 100° C., such as, for example, from about 4° C. to about 25° C.

The beverage can be a full-calorie beverage that has up to about 120 calories per 8 oz serving.

The beverage can be a mid-calorie beverage that has up to about 60 calories per 8 oz serving.

The beverage can be a low-calorie beverage that has up to about 40 calories per 8 oz serving.

The beverage can be a zero-calorie that has less than about 5 calories per 8 oz. serving.

In one embodiment, the beverage comprises natural sweetener(s) only, i.e. the only type of sweetener(s) are naturally-occurring.

III. Methods of Purification

The present invention also extends to methods of purifying a mogroside of the present invention.

In one embodiment, the present invention is a method for purifying a mogroside of the present invention comprising (i) passing a solution comprising a source material comprising a mogroside of the present invention through a HPLC column and (ii) eluting fractions comprising a mogroside of the present invention to provide a purified mogroside composition comprising a mogroside of the present invention. The HPLC column can be any suitable HPLC preparative or semi-preparative scale column.

As used herein, the term "preparative HPLC" refers to an HPLC system capable of producing high (500 or more) microgram, milligram, or gram sized product fractions. The term "preparative" includes both preparative and semi-preparative columns, but is not intended to include analytical columns, which provide fractions in the nanogram to low microgram range.

As used herein, an "HPLC compatible detector" is a detector suitable for use in an HPLC system which is capable of providing a detectable signal upon elution of a compound peak. For example, a detector capable of generating a signal when a compound elutes from the compound is an HPLC compatible detector. Where component absorbance varies widely, it may be necessary to utilize more than one detector. A detector capable of detecting a desired component is not an "incompatible" detector due to its inability to detect a non-desired peak.

An HPLC device typically includes at least the following components: a column, packed with a suitable stationary phase, a mobile phase, a pump for forcing the mobile phase through the column under pressure, and a detector for detecting the presence of compounds eluting off of the column. The devices can optionally include a means for providing for gradient elution, although such is not necessary using the methods described herein. Routine methods and apparatus for carrying out HPLC separations are well known in the art.

Suitable stationary phases are those in which the compound of interest elutes. Preferred columns can be, and are not limited to, normal phase columns (neutral, acidic or basic), reverse phase columns (of any length alkyl chain), a synthetic crosslinked polymer columns (e.g., styrene and divinylbenzene), size exclusion columns, ion exchange columns, bioaffinity columns, and any combination thereof. The particle size of the stationary phase is within the range from a few μm to several 100 μm.

Suitable detection devices include, but are not limited to, mass spectrometers, UV detectors, IR detectors and light scattering detectors. The methods described herein use any combination of these detectors. The most preferable embodiment uses mass spectrometers and UV detectors.

"Source material", as used herein, refers to the material being purified by the present method. The source material contains a mogroside of the present invention in a purity less than the purity provided by the present purification method. The source material can be liquid or solid. Exemplary source materials include, but are not limited to, mixtures of mogrosides and Luo Han Guo extract (commercial or prepared). In one embodiment, the source material derives from a bioconversion (discussed below).

As understood by persons skilled in the art, any solid source materials must be brought into solution prior to carrying out the HPLC method.

In one embodiment, a representative analytical HPLC protocol is correlated to a preparative or semi-preparative HPLC protocol used to purify a compound.

In another embodiment, appropriate conditions for purifying a mogroside of the present invention can be worked out by route scouting a representative sample for a given analytical HPLC column, solvent system and flow rate. In yet another embodiment, a correlated preparative or semi-preparative HPLC method can be applied to purify a mogroside of the present invention with modifications to the purification parameters or without having to change the purification parameters.

In some embodiments, the eluent (mobile phase) is selected from the group consisting of water, acetonitrile, methanol, 2-propanol, ethyl acetate, dimethylformamide, dimethylsulfide, pyridine, triethylamine, formic acid, trifluoroacetic acid, acetic acid, an aqueous solution containing ammonium acetate, heptafluorobutyric acid, and any combination thereof.

In one embodiment, the HPLC method is isocratic. In another embodiment, the HPLC method is a gradient. In still another embodiment, the HPLC method is step-wise.

In one embodiment, impurities are eluted off of the HPLC column after eluting one or more fractions containing a mogroside of the present invention. In another embodiment, impurities are eluted off of the HPLC column before eluting one or more fractions containing a mogroside of the present invention.

The method can further include removal of solvent from the eluted solution, i.e. drying. In one embodiment, the method further comprises partial removal of solvents from the eluted solution to provide a concentrate comprising a mogroside of the present invention. In another embodiment, the method further comprises removing substantially all the solvent from the eluted solutions to provide substantially dry composition comprising a mogroside of the present invention.

Removal of solvent can be performed by any known means to one of skill in the art including, but not limited to, evaporation, distillation, vacuum drying and spray drying.

The resulting purified fractions comprising a mogroside of the present invention can be further purified by other methods to increase purity. Suitable methods include, but are not limited to, crystallization, chromatography, extraction and distillation. Such methods are well-known to persons skilled in the art.

The source material can be one fraction, or multiple fractions, containing a mogroside of the present invention collected from at least one previous method or HPLC protocol. In one embodiment, multiple fractions from the same, previous methods or HPLC protocols are pooled and optionally, solvents are removed, prior to re-subjecting the source material to another method. In other embodiments, fractions from different, previous methods or HPLC protocol are pooled, and optionally, solvents are removed, prior to re-subjecting the source material to another method.

In one embodiment, the source material re-subjected to additional method(s) comprises liquid fractions obtained from one or more previous (and optionally, different) methods mixed with substantially dry material obtained via drying of fractions obtained from one or more previous (and optionally, different) methods. In another embodiment, the source material re-subjected to additional method(s) comprises substantially dry material obtained via drying of fractions obtained from one or more previous (and optionally, different) methods, where said source material is brought into solution prior to passing the solution through the next HPLC column.

The second and subsequent methods may have different HPLC protocols (e.g. solvent systems, columns, methods) and different steps following elution (e.g. partial removal of solvent, complete removal of solvent, elution of impurities, use of crystallization or extraction).

The material isolated can be subjected to further methods 2, 3, 4 or more times, each time providing a higher level of purity of purified mogroside of the present invention.

In one embodiment, the method provides a purified mogroside composition comprising a mogroside of the present invention in a purity of at least about 80% by weight or greater, such as, for example, at least about 85% by weight, at least about 90% by weight, at least about 95% by weight or at least about 97% or greater. In another embodiment, purification provides a pure mogroside of the present invention, i.e., >99% by weight on a dry basis.

IV. Methods of Bioconversion

The present invention also provides methods of preparing mogrosides of the present invention by bioconversion.

A biocatalytic process for preparing a mogroside of the present invention comprises contacting a medium comprising a composition comprising a starting mogroside with a biocatalyst, thereby producing a composition comprising a mogroside of the present invention (also referred to herein as a "target mogroside").

As used herein, "starting composition" refers to any composition containing the starting mogroside, i.e. the mogroside to be transformed into a mogroside of the present invention. The starting composition may be synthetic or purified (partially or entirely), commercially available or prepared. The starting mogroside can an isolated and purified mogroside, a mixture of mogrosides, an extract containing mogrosides (i.e. Luo Han Guo extract) or monk fruit juice.

The starting mogroside can be present in the starting composition in at least about 5% by weight on a dry basis, such as, for example, at least about 10% by weight on a dry basis, at least about 20% by weight on a dry basis, at least about 30% by weight on a dry basis, at least about 40% by weight on a dry basis, at least about 50% by weight on a dry basis, at least about 60% by weight on a dry basis, at least about 70% by weight on a dry basis, at least about 80% by weight on a dry basis, at least about 90% by weight on a dry basis or at least about 95% by weight on a dry basis.

As used here, "medium" refers to a composition (usually aqueous) comprising the starting composition and any other substances required for transformation of the starting mogroside to the mogroside of the present invention. For example, a medium can comprise water, a starting composition, buffer and/or salts.

In one embodiment, the medium comprises one or more co-substrates for the biocatalyst that function as glucosyl donors, e.g. sucrose, glucose-1-phosphate, α-D-glucose-1-fluoride, dextrin and starch. The starch can be from any suitable source, such as, for example, wheat, corn, potato, tapioca, sago, pullulan, maltose, lactose, and partially hydrolyzed starch.

As used herein, "bioconversion", "biocatalysis" or "biocatalytic" refers to the use of natural or genetically engineered biocatalysts, such as enzymes, or cells comprising one or more enzyme or enzyme lysates capable of single or multiple step chemical transformations of organic compounds. In a particular embodiment, the chemical transformation occurs naturally or does not occur naturally. Biocatalysis processes include fermentation, biosynthesis and biotransformation processes. Both isolated enzyme and whole-cell biocatalysis methods are known in the art. In a particular embodiment, the bioctalyasis occurs on a commercial scale.

A biocatalyst may be partially or wholly of biological origin, for example animal, plant and microbiological origin. Biocatalyst protein enzymes can be naturally occurring or recombinant proteins. The protein enzyme can be isolated from a naturally occurring source or can be produced in vivo, e.g., using a microbe transformed with a vector comprising a gene encoding the protein. In a particular embodiment, the protein is a heterologous naturally occurring protein produced in vivo. In another particular embodiment, the protein is a heterologous recombinant protein produced in vivo.

Suitable enzymes include, without limitation, glycosyltransferases such as glucosyltransferases. The enzymes may cause one or more metabolic conversions. Alternatively, bioconversion may comprise one or more enzyme, e.g., two, three, four or give enzymes in a multi-enzyme cascade.

In a particular embodiment, the enzyme is stable, and more particularly, stable in the absence of immobilization. In another embodiment, the enzyme is selective and has a broad operational range.

The bioconversion method may comprise a co-substrate. The co-substrate would vary according to the enzyme. In a particular embodiment, the enzyme is a glucosyltransferase and the co-substrate is uridine diphosphate glucose (UDP-glucose). UDP-glucose consists of the pyrophosphate group, the pentose sugar group, glucose and the nucleobase uracil.

The starting mogroside is the mogroside to which the biocatalyst adds one or more glucose units, thereby producing the mogroside of the present invention. Starting mogrosides are selected from Mogroside V and Mogroside IIIE.

In one embodiment, the starting mogroside is Mogroside V and the mogroside of the present invention is selected from the group consisting of CC-00371, CC-00367, CC-00436, CC-00417 and CC-00458. The identity of the mogroside of the present invention depends on the biocatalyst used.

A method for preparing CC-00371 comprises contacting a medium comprising a composition comprising Mogroside V and, optionally, a co-substrate, with a Beta-galactosidase or variant thereof to produce a composition comprising CC-00371. In a particular embodiment, the Beta-galactosidase is a variant from *Sulfolobus solfataricus*. In a more particular embodiment, the variant has a single mutation in the protein sequence, wherein the glutamic acid at position 387 is changed to glycine (EC:3.2.1.23; UniProtKB-P22498) (SEQ. ID 1). The co-substrate can be α-D-glucose-1-fluoride.

A method for preparing CC-00367 comprises contacting a medium comprising a composition comprising Mogroside V and, optionally, a co-substrate, with a Beta-galactosidase or variant thereof, to produce a composition comprising CC-00367. In a particular embodiment, a Beta-galactosidase is a variant from *Streptomyces* sp. In a more particular embodiment, the variant has a single mutation in the protein sequence, wherein the glutamic acid at position 383 is changed to alanine (EC:3.2.1.21; UniProtKB-Q59976) (SEQ. ID 2). The co-substrate can be α-D-glucose-1-fluoride.

A method for preparing CC-00436 comprises contacting a medium comprising a composition comprising Mogroside V and, optionally, a co-substrate, with dextran dextranase, to produce a composition comprising CC-00436. The co-substrate can be a starch, for example dextrin-10 from maize starch.

A method for preparing CC-00417 comprises contacting a medium comprising a composition comprising Mogroside V and, optionally, a co-substrate, with dextran sucrase to produce a composition comprising CC-00417. In a particular embodiment, the dextran sucrase is from *Leuconostoc citreum* DSM 20188. In a more particular embodiment, the dextran sucrase is provided as a lysate. The co-substrate can be sucrose.

A method for preparing CC-00458 comprises contacting a medium comprising a composition comprising Mogroside V with a glucosyltransferase, a glucose donor and a glucose donor recycling catalyst. The glucosyltransferase may be, for example, a UDP glycosyltransferase (UGT). The UGT may be, for example, UGT-1 or UGT-2. The UGT may be derived from a virus, archaea, bacteria or eukaryote. In a particular embodiment, the UGT is UGT-2 is produced by a bacteria, e.g., *Bacillus cereus*.

The glucose donor may be a nucleoside diphosphate sugar, a nucleoside monophosphate sugars and lipid phosphate. In a particular embodiment, the glucose donor is UDP-Glucose (UDP-Gluc).

In a particular embodiment, the method for preparing CC-00458 comprises contacting the medium comprising a composition comprising Mogroside V with a UDP-glycosyltranferase (UGT), UDP-glucose (UDP-Gluc), a UDP-glucose recycling catalyst and sucrose to provide a composition comprising CC-00458. In a particular embodiment, the UGT is UGT-2, preferably BcGT-1, a UGT produced by *B. cereus* (Uniprot reference: Q739H3). The UDP-glucose recycling catalyst can be sucrose synthase, preferably sucrose synthase derived from *A. thaliana* (e.g. AtSUS).

In another embodiment, the starting mogroside is Mogroside IIIE and the mogroside of the present invention is selected from CC-00434, CC-00478, CC-00483 and CC-00485.

A method for preparing CC-00434 comprises contacting a medium comprising a composition comprising Mogroside IIIE and, optionally, a co-substrate, with a Cyclodextrin Glucanotransferase (CGTase) or dextran dextrinase to produce a composition comprising CC-00434. In a particular embodiment, the CGTase is derived from *Paenibacillus macerans*, e.g. EC 2.4.1.19 (Amano). The co-substrate can be a starch, for example soluble starch.

A method for preparing CC-00478 and CC-00485 comprises (i) contacting a medium comprising a composition comprising Mogroside IIIE and, optionally, a co-substrate (e.g. sucrose), with a dextransucrase to provide a first reaction mixture and (iii) adding dextranase to the reaction mixture to produce a composition comprising CC-00478 and/or CC-00485. In a particular embodiment, the first reaction mixture is monitored for consumption of sucrose. The dextranase is added once the amount of sucrose is depleted or consumed.

A method for preparing CC-00483 comprises contacting a medium comprising a composition comprising Mogroside IIIE with a glucosyltransferase, a glucose donor and a glucose donor recycling catalyst. In a particular embodiment, the method for preparing CC-00485 comprises contacting the medium comprising a composition comprising Mogroside V with a UDP-glycosyltranferase (UGT), UDP-glucose, a UDP-glucose recycling catalyst and sucrose to provide a composition comprising CC-00483. In a particular embodiment, the UGT is UGT-2, preferably BcGT-1, a UGT produced by *B. cereus* (Uniprot reference: Q739H3). The UDP-glucose recycling catalyst can be sucrose synthase, preferably sucrose synthase derived from *A. thaliana* (e.g. AtSUS).

In another embodiment, the starting mogroside is Mogroside IV and the mogroside of the present invention is selected from CC-00467, CC-00468 and CC-00464.

A method for preparing CC-00467, CC-00468 and/or CC-00464 comprises contacting a medium comprising a composition comprising Mogroside IV with a glucosyltransferase, a glucose donor and a glucose donor recycling catalyst. In a particular embodiment, the method for preparing CC-00485 comprises contacting the medium comprising a composition comprising Mogroside V with a UDP-glycosyltranferase (UGT), UDP-glucose, a UDP-glucose recycling catalyst and sucrose to provide a composition comprising CC-00467, CC-00468 and/or CC-00464. In a particular embodiment, the UGT is UGT-2, preferably BcGT-1, a UGT produced by *B. cereus* (Uniprot reference: Q739H3). The UDP-glucose recycling catalyst can be sucrose synthase, preferably sucrose synthase derived from *A. thaliana* (e.g. AtSUS).

The biocatalysts used herein can be provided in the form of a whole cell suspension, a crude lysate, purified form or a combination thereof. In one embodiment, the biocatalyst is provided in purified form, i.e., as a purified enzyme. In another embodiment, the biocatalyst is provided in the form of a crude lysate. In still another embodiment, the biocatalyst is provided in the form of a whole cell suspension.

In a particular embodiment, the biocatalyst is an enzyme that is immobilized. The method of immobilization may vary and includes, e.g., immobilization to a solid support, encapsulation or crosslinking. The solid support may be, for example, a synthetic resin, biopolymers, or inorganic solid.

In another embodiment, the biocatalyst is provided in the form of one or more cells, i.e., the biocatalyst is associated with a cell(s). The biocatalyst can be located on the surface of the cell, inside the cell, or both on the surface of the cell and inside the cell. In a particular embodiment, the biocatalyst is provided in the form of a multicellular biocatalyst.

In another embodiment, the biocatalyst is provided in the form of a microorganism, i.e., the biocatalyst is associated with a microorganism. The microorganism can be any microorganism possessing the necessary biocatalyst(s)/enzyme(s). Suitable microorganisms include, but are not limited to, *E. coli, Acetobacter capsulatus, Leuconostoc citreum, Saccharomyces* sp., *Aspergillus* sp., *Pichia* sp., *Bacillus* sp., *Yarrowia* sp. etc.

In one embodiment, the microorganism is free (i.e., not immobilized) when contacted with the starting composition.

In another embodiment, the microorganism is immobilized when contacted with the starting composition. For example, the microorganism may be immobilized to a solid support made from inorganic or organic materials. Non-limiting examples of solid supports suitable to immobilize the microorganism include derivatized cellulose or glass, ceramics, metal oxides or membranes. The microorganism may be immobilized to the solid support, for example, by covalent attachment, adsorption, cross-linking, entrapment or encapsulation.

In still another embodiment, the biocatalyst is secreted by the microorganism into the reaction medium.

The reactions of the present invention are typically performed at temperatures from about 20° C. to about 70° C., such as, for example from about 23° C. to about 40° C., or about 30° C.

The reactions of the present invention are typically performed in the pH range of about 3 to about 9, such as, for example, from about 5 to about 8.

In a particular embodiment, the methods of the present invention provide a composition comprising the mogroside of the present invention in an amount of about 1% or greater by weight, such as, for example, about 5% or greater, about 10% or greater, about 20% or greater, about 30% or greater, about 40% or greater, about 50% or greater, about 60% or greater, about 70% or greater, about 80% or greater or about 90% or greater by weight.

The composition comprising the target mogroside of the present invention includes reaction by-products, excess reagents, unreacted starting material and other undesirable materials. Accordingly, in some embodiments, the methods disclosed herein further comprise separating the mogroside of the present invention from at least some of these undesirable materials in the composition to provide a separated mogroside composition. Any suitable method separation method can be used, such as, for example, lysis, crystallization, separation by membranes, centrifugation, extraction (liquid or solid phase), chromatographic separation, HPLC (preparative or analytical) or a combination of such methods. In a particular embodiment, separation can be achieved by centrifugation.

In one embodiment, the mogroside of the present invention is continuously removed from the medium while the conversion progresses. In another embodiment, the mogroside of the present invention is separated from the medium after the reaction is quenched (not necessarily complete).

Separation may result in separated mogroside compositions having a lower mogroside of the present invention content than desired and/or the composition may contain additional components, e.g., non-desirable mogrosides (in identity or content) and/or residual reaction products. In one embodiment, the separated mogroside composition comprises the mogroside of the present invention in a purity of at least about 50% by weight or greater on a dry basis, such as, for example, about 60% or greater, about 65% or greater, about 70% or greater, about 75% or greater, about 80% or greater, about 85% or greater, about 90% or greater.

The separated mogroside of the present invention composition can be further purified to provide a purified mogroside composition of the present invention composition. The term "purified", as used herein with respect to bioconversion, refers to a composition having at least about 80% by weight of the mogroside of the present invention on a dry basis. In one embodiment, the purified composition contains at least about 90% of the mogroside of the present invention by weight, such as, for example, at least about 91%, at least than about 92%, at least about 93%, at least about 94%, at least about 95%, at least about 96%, at least about 97%, at least than about 98% or at least about 99% by weight.

In exemplary embodiments, purification provides a pure mogroside of the present invention, i.e., >99% by weight on a dry basis.

Purification can be affected by any means known to one of skill in the art including, but not limited to, crystallization, separation by membranes, centrifugation, extraction (liquid or solid phase), chromatographic separation, HPLC (preparative or analytical) or a combination of such methods. In a particular embodiment, HPLC is used. In a more particular embodiment, preparative HPLC is used. Preparative HPLC can be iteratively performed until the desired purity is achieved. Any of the purification methods described in the "Methods of Purification" section herein can be used.

V. Methods of Use

The mogrosides and compositions of the present invention can be used to impart sweetness to consumables.

In one aspect, the present invention is a method of preparing a sweetened consumable comprising (i) providing a consumable and (ii) adding at least one mogroside of the present invention to the consumable to provide a sweetened consumable.

In a particular embodiment, a method of preparing a sweetened consumable comprises (i) providing an unsweetened consumable and (ii) adding at least one mogroside of the present invention to the unsweetened consumable to provide a sweetened consumable.

In a particular embodiment, the present invention is a method of preparing a sweetened beverage comprising (i) providing a beverage and (ii) adding at least one mogroside of the present invention to the beverage to provide a sweetened beverage.

In a particular embodiment, the present invention is a method of preparing a sweetened beverage comprising (i) providing an unsweetened beverage and (ii) adding at least one mogroside of the present invention to the unsweetened beverage to provide a sweetened beverage.

In the above methods, the mogroside of the present invention may be provided as such, i.e., in the form of a compound, or in form of a composition. The amount of mogroside of the present invention is effective to provide a concentration that is at or above its sweetness recognition threshold when added to the consumable (e.g., the beverage).

The present invention also includes methods of preparing sweetened compositions (e.g., sweetened consumables) and flavor enhanced compositions by adding at least one mogroside of the present invention or a composition comprising the same to such compositions/consumables.

EXAMPLES

Example 1: Purification and Characterization of CC-00401

Materials. The material used for the isolation of CC-00401 was a Luo Han Guo extract, Lot #MOV04-160117/2 (Supplier: LAYN; Identification number: 3502-149-2).

HPLC Analysis: HPLC analyses were performed on an Agilent 1200 system coupled with Photo Diode Array (PDA) detector. Samples from multiple process and final purity evaluation were performed using the method conditions described in Table 1.

TABLE 1

Analytical HPLC Conditions for Fraction Analysis in Primary Process

| | |
|---|---|
| Column: | Phenomenex Polar RP 80A (250 × 4.6 mm, 4 μm) |
| Column Temperature | 55° C. |
| Sample Temperature | Ambient |
| Mobile Phase A and B | A: Water and B: Acetonitrile |
| Flow Rate | 1 mL/min |
| Injection Volume | 20 μL |
| Detection @ UV | 210 nm |
| Runtime | 38 min |

| Gradient | | |
|---|---|---|
| Time (min) | % A | % B |
| 0 | 95 | 5 |
| 7 | 75 | 25 |
| 17 | 70 | 30 |
| 27 | 25 | 75 |
| 27.5 | 5 | 95 |
| 32.5 | 5 | 95 |
| 35 | 95 | 5 |
| 38 | 95 | 5 |

Preparative HPLC Primary Processing Method: The preparative primary processing of Lot #MOV04-1601 17/2 (Identification number 3502-149-2), to collect Peak ID: 3502-149-2-F1 was performed using Gemini NX C18 column (150×30 mm, 5 μm) on Agilent preparative HPLC coupled with UV-Vis detector. Details of preparative primary processing method conditions are summarized in Table 2.

TABLE 2

Preparative HPLC method conditions for primary processing

| Column | Gemini NX C18 (150 × 30 mm, 5 μm) |
|---|---|
| Detection | UV@ 210 nm |
| Mobile Phase: A | MilliQ-water |
| Mobile Phase: B | Acetonitrile:Water (90:10, v/v) |
| Elution | Gradient |
| Flow Rate | 25.0 mL/min |
| Sample preparation | 100 mg dissolved in ~1 mL of diluent (milli-Q-water) |
| Injection volume | 2.0 mL (~200 mg) |
| Run time | 32.0 min |

Gradient

| Time | % A | % B |
|---|---|---|
| 0 | 95 | 5 |
| 20 | 70 | 30 |
| 22 | 70 | 30 |
| 24 | 10 | 90 |
| 26 | 10 | 90 |
| 27 | 95 | 5 |
| 32 | 95 | 5 |

Preparative HPLC Secondary Processing Method: The secondary processing of Peak ID: 3502-149-2-F1 was performed using XBridge BEH Prep OBD Amide column (250 30 mm, 5 μm) on Agilent preparative HPLC coupled with UV-Vis detector. Details of preparative secondary processing method conditions are summarized in Table 3.

TABLE 3

Preparative HPLC method conditions for secondary processing of Peak ID: 3502-149-2-F1 (Lot # IN-SSB-C-60-1)

| Column | XBridge BEH Prep OBD Amide (250 × 30 mm, 5 μm) |
|---|---|
| Detection | UV@210 nm |
| Mobile Phase: A | Water |
| Mobile Phase: B | Acetonitrile |
| Elution | Gradient |
| Flow Rate | 30.0 mL/min |
| Sample preparation | 1 g dissolved in ~4 mL of diluent (milli-Q-water) |
| Injection volume | 1 mL (~250 mg) |
| Run time | 45 min |

Gradient

| Time | % A | % B |
|---|---|---|
| 0 | 15 | 85 |
| 25 | 30 | 70 |
| 40 | 30 | 70 |
| 41 | 15 | 85 |
| 45 | 15 | 85 |

Preparative HPLC Tertiary Processing Method: The tertiary processing of Peak ID: 3502-149-2-F1A was performed using Gemini NX C18 column (250×30 mm, 10 μm) on Agilent preparative HPLC coupled with UV-Vis detector. Details of preparative tertiary processing method conditions are summarized in Table 4.

TABLE 4

Preparative HPLC method conditions for tertiary processing of Peak ID: 3502-149-2-F1A (Lot# IN-SSB-C-62-1)

| Column | Gemini NX C18 (250 × 30 mm, 10 μm) |
|---|---|
| Detection | UV@210 nm |
| Mobile Phase: A | Milli-Q-water |
| Mobile Phase: B | Acetonitrile |
| Elution | Gradient |
| Flow Rate | 25.0 mL/min |
| Sample preparation | 100 mg dissolved in ~1 mL of diluent (milli-Q-water) |
| Injection Volume | 0.15 mL (~15 mg) |
| Run time | 45 min |

Gradient

| Time | % A | % B |
|---|---|---|
| 0 | 80 | 20 |
| 40 | 70 | 30 |
| 41 | 80 | 20 |
| 45 | 80 | 20 |

Isolation Procedure: The collected fractions from the preparative processing were pooled and lyophilized using Labconco Lyopholizer, (collector temperature maintained at −44° C. under vacuum).

MS and MS/MS. MS and MS/MS data were generated with a Waters QTof Micro mass spectrometer equipped with an electrospray ionization source. The sample was analyzed by negative ESI. The sample (~0.2 mg) was diluted with 50:50 ACN:H$_2$O to a concentration of ~0.2 mg/mL and introduced via direct infusion.

NMR. The sample was prepared by dissolving 2.3 mg in 250 μL of CD$_3$OD and NMR data were acquired on a Bruker Avance 500 MHz instruments equipped with 2.5 mm inverse probe and 5 mm broad band probe. The $^1$H NMR spectrum was referenced to the CHD$_2$OD resonance at $\delta_H$ 3.30 ppm and $^{13}$C NMR spectrum was referenced to the CD$_3$OD resonance at Sc 49.0 ppm. NMR data were also acquired in pyridine-d$_5$ (2.8 mg in 150 μL) in which $^1$H and $^{13}$C NMR spectrum were referenced as discussed in Results and Discussion section below.

Results and Discussion

Unless otherwise noted, all solvent ratios are listed as percent by volume (v/v).

Primary Purification of CC-00401. Approximately 50 g of #3502-149-2 was processed using the primary preparative HPLC method described in Table 2. The purity of the fraction was determined using the analytical method summarized in Table 1. Fraction of Peak ID: 3502-149-2-F1 (target fraction retention time range: 15 to 19.5 min), collected from the primary processing of whole quantity was pooled and lyophilized for isolation. The final yield of Peak ID: 3502-149-2-F1 (Lot #IN-SSB-C-60-1) was 7.50 g.

Secondary Processing. Approximately 7.50 g of Peak ID: 3502-149-2-F1 (Lot #IN-SSB-C-60-1) was processed using preparative HPLC method conditions described in Table 3. Fraction of Peak ID: 3502-149-2-F1-A (target fraction retention time range: 34 to 36.5 min), collected from the secondary processing of #3502-149-2-F1 was pooled and lyophilized for isolation. The final yield of Peak ID: 3502-149-2-F1-A (Lot #IN-SSB-C-62-1) was 800 mg.

Tertiary Processing: Approximately 800 mg of Peak ID: 3502-149-2-F1-A (Lot #IN-SSB-C-62-1) was processed using preparative HPLC method conditions described in Table 4. Fraction of Peak ID:3502-149-2-F1-A8 (Lot #IN-SSB-C-64-8; (target fraction retention time range: 19 to 20 min), collected from the third processing was pooled and lyophilized for isolation. The final yield of Peak ID: 3502-149-2-F1-A8 (Lot #IN-SSB-C-64-8) was 80 mg with purity of 98.1% (area %).

Mass Spectrometry. The ESI-TOF mass spectrum acquired by infusing a sample of CC-00401 showed a $[M-H]^-$ ion at m/z 1447.6974. The mass of the $[M-H]^-$ ion was in good agreement with the molecular formula $C_{66}H_{112}O_{34}$ (calcd for $C_{66}H_{111}O_{34}$: 1447.6957, error: 1.2 ppm) expected. The MS data confirmed that CC-00401 had a nominal mass of 1448 Daltons with the molecular formula, $C_{66}H_{112}O_{34}$. The ions observed at m/z 1545.6537 is most likely due to $[M-H+H_3PO_4]^-$.

The MS/MS spectrum of CC-00401, selecting the $[M-H]^-$ ion at m/z 1447.7 for fragmentation, indicated sequential loss of six glucose units at m/z 1285.6532, 1123.5703, 961.4950, 799.4794, 637.4259, and 475.3725, indicated the presence of six glucose units in the structure. Following the loss of one sugar from the structure, an alternative fragmentation pathway is also observed in the spectrum, which corresponded to loss of water molecule from the central triterpene core followed by sequential loss of glucose units at m/z 1267.5936, 1105.5958, 943.5030, 781.4406 and 619.4109.

NMR Spectroscopy. A series of NMR experiments including $^1$H NMR (500 MHz, CD$_3$OD), $^{13}$C NMR (125 MHz, CD$_3$OD), $^1$H-$^1$H COSY (500 MHz, CD$_3$OD), HSQC-DEPT (500 MHz, CD$_3$OD), HMBC (500 MHz, CD$_3$OD), ROESY (500 MHz, CD$_3$OD), and 1D TOCSY (500 MHz, CD$_3$OD) were acquired to allow assignment of CC-00401.

The 1D and 2D NMR data indicated that the central core of the glycoside is a triterpene. A summary of the $^1$H and $^{13}$C chemical shifts for the aglycone are found in Table 5.

TABLE 5

$^1$H and $^{13}$C NMR (500 and 125 MHz, CD$_3$OD), assignments of the CC-00401 aglycone.

| | CC-00401 | |
| --- | --- | --- |
| Position | $^{13}$C | $^1$H |
| 1 | 27.3 | 1.48 m |
| | | 2.23 m |
| 2 | 30.0 | 1.90 m |
| | | 1.95 m |
| 3 | 87.7 | 3.54 m |
| 4 | 42.9 | — |
| 5 | 145.1 | — |
| 6 | 119.5 | 5.48 brd (5.8) |
| 7 | 25.1 | 1.81 m |
| | | 2.39 m |
| 8 | 44.6 | 1.66 m |
| 9 | 40.9 | — |
| 10 | 37.3 | 2.49 brd (12.1) |
| 11 | 79.4 | 3.85 m |
| 12 | 41.1 | 1.81 m |
| | | 1.87 m |
| 13 | 48.3 | — |
| 14 | 50.6 | — |
| 15 | 35.4 | 1.13 m |
| | | 1.21 m |
| 16 | 29.5 | 1.32 m |
| | | 1.98 m |
| 17 | 51.8 | 1.62 m |
| 18 | 17.1 | 0.91 s |
| 19 | 26.2 | 1.11 s |
| 20 | 37.5 | 1.45 m |
| 21 | 19.3 | 0.97 d (6.3) |
| 22 | 34.1 | 1.47 m |
| | | 1.56 m |
| 23 | 30.0 | 1.39 m |
| | | 1.55 m |
| 24 | 93.3 | 3.39 m |

TABLE 5-continued $^1$H and $^{13}$C NMR (500 and 125 MHz, CD$_3$OD), assignments of the CC-00401 aglycone.

| | CC-00401 | |
| --- | --- | --- |
| Position | $^{13}$C | $^1$H |
| 25 | 73.9 | — |
| 26 | 26.8† | 1.11 s† |
| 27 | 24.1† | 1.14 s† |
| 28 | 28.1 | 1.08 s |
| 29 | 26.2 | 1.19 s |
| 30 | 20.0 | 0.88 s |

†Assignments can be interchanged.

A summary of the $^1$H and $^{13}$C chemical shifts for the glycoside at C-3 are found in Table 6.

TABLE 6

$^1$H and $^{13}$C NMR (500 and 125 MHz, CD$_3$OD), assignments of the CC-00401 C-3 glycoside.

| Position | $^{13}$C | $^1$H |
| --- | --- | --- |
| Glc$_{II}$-1 | 106.1 | 4.33 d (7.2) |
| Glc$_{II}$-2 | 75.7¶ | 3.17 m |
| Glc$_{II}$-3 | 77.7-78.5§ | 3.33 m |
| Glc$_{II}$-4 | 71.4-71.8ε | 3.31 m |
| Glc$_{II}$-5 | 77.0 | 3.58 m |
| Glc$_{II}$-6 | 70.3 | 3.80 m, 4.08 m |
| Glc$_{I}$-1 | 103.3 | 4.61 d (7.8) |
| Glc$_{I}$-2 | 83.9 | 3.41 m |
| Glc$_{I}$-3 | 77.7-78.5§ | 3.56 m |
| Glc$_{I}$-4 | 71.4-71.8ε | 3.32 m |
| Glc$_{I}$-5 | 77.7-78.5§ | 3.24 m |
| Glc$_{I}$-6 | 62.7† | 3.65 m, 3.85 m |
| Glc$_{VII}$-1 | 105.8 | 4.57 d (7.8) |
| Glc$_{VII}$-2 | 76.2 | 3.28 m |
| Glc$_{VII}$-3 | 77.7-78.5§ | 3.37 m |
| Glc$_{VII}$-4 | 71.4-71.8ε | 3.29 m |
| Glc$_{VII}$-5 | 77.7-78.5§ | 3.29 m |
| Glc$_{VII}$-6 | 62.7† | 3.71 m, 3.90 m |

¶Two carbons resonance at 75.7 ppm (75.67 and 75.70 ppm), hence chemical shifts could not be unequivocally assigned.
§Nine carbon resonances in the range of 77.7-78.5 ppm (77.67, 77.83, 77.93, 77.97, 78.06, 78.17 and 78.54 ppm; two additional carbon resonances overlap in this region), hence chemical shifts could not be unequivocally assigned.
εFive carbon resonances in the range of 71.4-71.8 ppm (71.35, 71.56, 71.60 and 71.76 ppm; one additional carbon overlap in this region), hence chemical shifts could not be unequivocally assigned.
†Three carbon resonances at 62.7 ppm (62.65, 62.69 and 62.71 ppm), hence chemical shifts could not be unequivocally assigned.

§ Nine carbon resonances in the range of 77.7-78.5 ppm (77.67, 77.83, 77.93, 77.97, 78.06, 78.17 and 78.54 ppm; two additional carbon resonances overlap in this region), hence chemical shifts could not be unequivocally assigned.

ΣFive carbon resonances in the range of 71.4-71.8 ppm (71.35, 71.56, 71.60 and 71.76 ppm; one additional carbon overlap in this region), hence chemical shifts could not be unequivocally assigned.

†Three carbon resonances at 62.7 ppm (62.65, 62.69 and 62.71 ppm), hence chemical shifts could not be unequivocally assigned.

A summary of the $^1$H and $^{13}$C chemical shifts for the glycoside at C-24 are found in Table 7.

TABLE 7

$^1$H and $^{13}$C NMR (500 and 125 MHz, CD$_3$OD), assignments of the CC-00401 C-24 glycoside.

| Position | $^{13}$C | $^1$H |
| --- | --- | --- |
| Glc$_f$-1 | 104.2 | 4.43 d (7.2) |
| Glc$_f$-2 | 81.3 | 3.61 m |

TABLE 7-continued $^1$H and $^{13}$C NMR (500 and 125 MHz, CD$_3$OD), assignments of the CC-00401 C-24 glycoside.

| Position | $^{13}$C | $^1$H |
|---|---|---|
| Glc$_I$-3 | 78.7 | 3.58 m |
| Glc$_I$-4 | 71.4-71.8$^\epsilon$ | 3.33 m |
| Glc$_I$-5 | 76.5 | 3.50 m |
| Glc$_I$-6 | 70.1 | 3.61 m, 4.23 m |
| Glc$_{II}$-1 | 104.4 | 4.28 d (7.7) |
| Glc$_{II}$-2 | 75.2 | 3.20 m |
| Glc$_{II}$-3 | 77.7-78.5$^\S$ | 3.36 m |
| Glc$_{II}$-4 | 71.4-71.8$^\epsilon$ | 3.27 m |
| Glc$_{II}$-5 | 77.7-78.5$^\S$ | 3.26 m |
| Glc$_{II}$-6 | 62.7$^\dagger$ | 3.65 m, 3.85 m |
| Glc$_{III}$-1 | 104.5 | 4.77 d (7.8) |
| Glc$_{III}$-2 | 75.7$^\P$ | 3.27 m |
| Glc$_{III}$-3 | 77.7-78.5$^\S$ | 3.36 m |
| Glc$_{III}$-4 | 72.4 | 3.21 m |
| Glc$_{III}$-5 | 77.7-78.5$^\S$ | 3.28 m |
| Glc$_{III}$-6 | 63.6 | 3.63 m, 3.86 m |

$^\S$Nine carbon resonances in the range of 77.7-78.5 ppm (77.67, 77.83, 77.93, 77.97, 78.06, 78.17 and 78.54 ppm; two additional carbon resonances overlap in this region), hence chemical shifts could not be unequivocally assigned.
$^\epsilon$Five carbon resonances in the range of 71.4-71.8 ppm (71.35, 71.56, 71.60 and 71.76 ppm; one additional carbon overlap in this region), hence chemical shifts could not be unequivocally assigned.
$^\dagger$Three carbon resonances at 62.7 ppm (62.65, 62.69 and 62.71 ppm), hence chemical shifts could not be unequivocally assigned.
$^\P$Two carbons resonance at 75.7 ppm (75.67 and 75.70 ppm), hence chemical shifts could not be unequivocally assigned.

The structure of CC-00401 was determined to be mogro-3-O-{[(β-D-glucopyranosyl-(1→2)]-[β-D-glucopyranosyl-(1→6))]-β-D-glucopyranoside}-24-O-{[β-D-glucopyranosyl-(1→2)]-[β-D-glucopyranosyl-(1→6)-β-D-glucopyranoside}. CC-00401 is an isomer of Mogroside VI that differs by the linkage of a sugar unit.

Example 2: Purification and Characterization of CC-00403

The material used for the isolation of CC-00403 was a Luo Han Guo extract (Lot #CDC-A-12-1): MonkGold MV40 from GLG (Lot GLG-MV40-2015112204).

HPLC Analysis. HPLC analyses were performed on an Agilent 1200 system coupled with Photo Diode Array (PDA) detector. Samples from multiple process and final purity evaluation were performed using the method conditions described in Table 8.

TABLE 8

Analytical HPLC conditions for fraction analysis in multiple processes and final purity evaluation

| Column: | Phenomenex Polar RP (250 × 4.6 mm, 5 μm) |
|---|---|
| Column Temperature | 55° C. |
| Sample Temperature | Ambient |
| Mobile Phase A and B | A: Water and B: Acetonitrile |
| Flow Rate | 1 mL/min |
| Injection Volume | 20 μL |
| Detection @ UV | 210 nm |
| Runtime | 38 min |

Gradient

| Time (min) | % A | % B |
|---|---|---|
| 0 | 95 | 5 |
| 7 | 75 | 25 |
| 17 | 70 | 30 |
| 27 | 25 | 75 |
| 27.5 | 5 | 95 |
| 32.5 | 5 | 95 |
| 35 | 95 | 5 |
| 38 | 95 | 5 |

Primary Preparative HPLC Method. Preparative HPLC analyses were performed on an Agilent preparative HPLC coupled with a UV-Vis detector. Multiple processes were performed to isolate CC-00403 as described below.

Preparative HPLC Primary Processing Method: The preparative primary processing of base line cut fraction Lot #MMM-A-31-1 and CDC-A-12-1, to collect Peak ID: F3P2 was performed using Gemini NX C18 column (150×30 mm, 5 μm). Details of preparative primary processing method conditions are summarized in Table 9.

TABLE 9

Preparative HPLC method conditions for primary processing

| Column | Gemini NX C18, (150 mm × 30 mm, 5 μm) |
|---|---|
| Mobile Phases A | Water |
| Mobile Phase B | Acetonitrile:water; 90:10 |
| Flow Rate | 25.0 mL/min |
| Load (mg) | 1.5 mL (loading concentration ~150 mg) |
| Detection @ UV | 210 nm |

Gradient description

| Time (min) | % A | % B |
|---|---|---|
| Initial | 90 | 10 |
| 20 | 70 | 30 |
| 24 | 10 | 90 |
| 26 | 10 | 90 |
| 27 | 90 | 10 |
| 32 | 90 | 10 |

Preparative HPLC Secondary Processing Method: The secondary processing of Peak ID: F3P2 was performed using Synergy Polar RP 80 A column (150×10 mm, 4 μm). Details of preparative secondary processing method conditions are summarized in Table 10.

TABLE 10

Preparative HPLC method conditions for secondary processing

| Column | Synergi Polar RP 80A (150 mm × 10 mm, 4 μm) |
|---|---|
| Mobile Phases A | Water |
| Mobile Phase B | Acetonitrile:Water (90:10) |
| Flow Rate | 6.0 mL/min |
| Detection @ UV | 210 nm |
| Sample Preparation | 100 mg of #F3P2 dissolved in ~1.5 mL of diluent (Milli-Q-water) |
| Load (mg) | 0.3 mL (20 mg) |

Gradient description

| Time (min) | % A | % B |
|---|---|---|
| Initial | 90 | 5 |
| 7 | 75 | 25 |
| 17 | 70 | 30 |
| 19 | 5 | 95 |
| 20 | 95 | 5 |
| 25 | 95 | 5 |

Preparative HPLC Tertiary Processing Method: The tertiary processing of Peak ID: F3P2A was performed using Kinetex C18, 100A column (250×21.2 mm, 5 μm). Details of preparative third processing method conditions are summarized in Table 11.

TABLE 11

Preparative HPLC method conditions for tertiary processing

| | |
|---|---|
| Column | Kinetex C18 100A (250 mm × 21.2 mm, 5 μm) |
| Mobile Phases A | Water |
| Mobile Phase B | Acetonitrile |
| Flow Rate | 15.0 mL/min |
| Load (mg) | 0.2 mL (20 mg) |
| Detection @ UV | 210 nm |
| Sample Preparation | 100 mg of #F3P2A dissolved in ~1 mL of diluent (Milli-Q-water) |
| Runtime | 30 min |
| Elution: | Isocratic |

| % A | % B |
|---|---|
| 80 | 20 |

Preparative HPLC Quaternary Processing Method: The quaternary processing of Peak ID: F3P2A1 was performed using YMC Trait C18 column (150×30 mm, 5 μm). Detailed conditions are summarized in Table 12.

TABLE 12

Preparative HPLC method conditions for quaternary processing

| | |
|---|---|
| Column | YMC Trait C18 (150 × 30 mm, 5 μm) |
| Mobile Phases A | Water |
| Mobile Phase B | Acetonitrile:Water (90:10) |
| Flow Rate | 25.0 mL/min |
| Load (mg) | 0.2 mL (20 mg) |
| Detection @ UV | 210 nm |
| Sample Preparation | 100 mg of #F3P2A1 dissolved in ~1 mL of diluent (Milli-Q-water) |

Gradient description

| Time (min) | % A | % B |
|---|---|---|
| Initial | 80 | 20 |
| 20 | 70 | 30 |
| 21 | 80 | 20 |
| 25 | 80 | 20 |

Isolation Procedure: The collected fractions from the preparative processing were pooled and lyophilized using Labconco Lyopholizer, (collector temperature maintained at −44° C. under vacuum).

MS and MS/MS. MS and MS/MS data were generated with a Waters QTof Micro mass spectrometer equipped with an electrospray ionization source. The sample was analyzed by negative ESI. The sample (~0.2 mg) was diluted with 50:50 ACN:H$_2$O to a concentration of ~0.2 mg/mL and introduced via direct infusion.

NMR. The sample was prepared by dissolving 2.6 mg in 150 μL of CD$_3$OD and NMR data were 10 acquired on a Bruker Avance 500 MHz instrument equipped with a 2.5 mm inverse probe and a 5 mm broad band probe. The $^1$H NMR spectrum was referenced to the CHD$_2$OD resonance at $\delta_H$ 3.30 ppm and $^{13}$C NMR spectrum was referenced to the CD$_3$OD resonance at $\delta_C$ 49.0 ppm.

Results and Discussion

Primary Processing: Approximately 20 g of Lot #MMM-A-31-1 was processed using the primary preparative HPLC method described above. The purity of the fraction was determined using the analytical method summarized above. Fractions of the peak (ID: F3P2; retention time 18-19 mins), collected from the primary processing of whole quantity was pooled and lyophilized. The final yield of Peak ID: F3P2 (Lot #IN-NCV-A-174-2) was 439 mg.

Secondary Processing: Approximately 439 mg of the peak (ID: F3P2) (Lot #IN-NCV-A-174-2) was processed using preparative HPLC method conditions described above. Fractions of the peak (ID: F3P2-A; retention time 9-10 mins) collected were pooled and lyophilized. The final yield of Peak ID: F3P2-A (Lot #IN-NCV-A-187-1) was 292 mg.

Tertiary Processing: Approximately 292 mg of the peak ID: F3P2-A (Lot #IN-NCV-A-187-1) was processed using preparative HPLC method conditions described above. Fractions of Peak ID:F3P2-A1 (Lot #IN-NCV-A-189; retention time 16-17.5 mins) collected from the third processing were pooled and lyophilized. The final yield of Peak ID:F3P2-A1 (Lot #IN-NCV-A-189) was 16 mg.

Quaternary Processing: Approximately 16 mg of the peak ID: F3P2A1 (Lot #IN-NCV-A-189) was processed using preparative HPLC method conditions described above. Fractions of the Peak ID: F3P2-A1-b (Lot #IN-GKR-A-76) collected from the quaternary processing were pooled and lyophilized. The final yield of peak ID: F3P2A1b (Lot #IN-GKR-A-76) obtained was 8 mg. The final HPLC purity was determined using analytical method conditions summarized above and found to be 89.6% (area %) with a retention time 11.59 min.

Mass Spectrometry. The ESI-TOF mass spectrum acquired by infusing a sample of CC-00403 showed a [M−H]$^-$ ion at m/z 1447.700. The mass of the [M−H]$^-$ ion was in good agreement with the molecular formula $C_{66}H_{112}O_{34}$ (calcd for $C_{66}H_{111}O_{34}$: 1447.6957, error: 3.5 ppm) expected. The MS data confirmed that CC-00403 has a nominal mass of 1448 Daltons with the molecular formula, $C_{66}H_{112}O_{34}$.

The MS/MS spectrum of CC-00403, selecting the [M−H]$^-$ ion at m/z 1447.7 for fragmentation, indicated sequential loss of six glucose units at m/z 1285.6360, 1123.5541, 961.4950, 799.4656, 637.4382, and 475.3937 indicated presence of six glucose units in the structure. Following the loss of one sugar from the structure an alternative fragmentation pathway was also observed in the spectrum which corresponded to loss of water molecule from the central triterpene core followed by sequential loss of glucose units at m/z 1267.6282, 1105.5958, 943.5030, 781.4813 and 619.4592. The ion observed at m/z 383.1192 was most likely due to the loss of six glucose and C-24 isopropyl hydroxyl units.

NMR Spectroscopy. A series of NMR experiments including $^1$H NMR, $^{13}$C NMR, $^1$H-$^1$H COSY, HSQC-DEPT, HMBC, ROESY, and 1D TOCSY were acquired to allow assignment of CC-00403.

The 1D and 2D NMR data indicated that the central core of the glycoside is a triterpene. A summary of the $^1$H and $^{13}$C chemical shifts for the aglycone are found in Table 13.

TABLE 13

$^1$H and $^{13}$C NMR (500 and 125 MHz, CD$_3$OD), assignments of the aglycone.

| Position | $^{13}$C | $^1$H |
|---|---|---|
| 1 | 27.2 | 1.48 m |
|   |      | 2.22 m |
| 2 | 29.7 | 1.89 m |
|   |      | 1.95 m |
| 3 | 88.2 | 3.46 m |
| 4 | 42.9 | — |
| 5 | 145.1 | — |
| 6 | 119.6 | 5.48 brd (5.7) |
| 7 | 25.1 | 1.81 m |
|   |      | 2.38 m |

TABLE 13-continued $^1$H and $^{13}$C NMR (500 and 125 MHz, CD$_3$OD), assignments of the aglycone.

| Position | $^{13}$C | $^1$H |
|---|---|---|
| 8 | 44.7 | 1.66 m |
| 9 | 40.9 | — |
| 10 | 37.2 | 2.49 brd (12.0) |
| 11 | 79.4 | 3.84 m |
| 12 | 41.1 | 1.81 m |
|  |  | 1.87 m |
| 13 | 48.3 | — |
| 14 | 50.6 | — |
| 15 | 35.4 | 1.13 m |
|  |  | 1.21 m |
| 16 | 29.5 | 1.33 m |
|  |  | 1.99 m |
| 17 | 51.8 | 1.62 m |
| 18 | 17.1 | 0.91 s |
| 19 | 26.2 or 26.3 | 1.10 s |
| 20 | 37.5 | 1.45 m |
| 21 | 19.4 | 0.97 d (6.2) |
| 22 | 34.2 | 1.47 m |
|  |  | 1.56 m |
| 23 | 29.9 | 1.41 m |
|  |  | 1.55 m |
| 24 | 93.4 | 3.40 m |
| 25 | 73.9 | — |
| 26 | 26.9† | 1.11 s† |
| 27 | 24.3† | 1.14 s† |
| 28 | 28.0 |  1.07 s |
| 29 | 26.2 or 26.3 | 1.18 s |
| 30 | 20.0 | 0.88 s |

†Assignments can be interchanged.

A summary of the $^1$H and $^{13}$C chemical shifts for the glycoside at C-3 are found in Table 14.

TABLE 14

$^1$H and $^{13}$C NMR (500 and 125 MHz, CD$_3$OD), assignments of the C-3 glycoside.

| Position | $^{13}$C | $^1$H |
|---|---|---|
| Glc$_{II}$-1 | 106.4 | 4.28 d (~7.5) |
| Glc$_{II}$-2 | 75.1-75.6¥ | 3.19 m |
| Glc$_{II}$-3 | 77.9-78.2§ | ~3.30 m |
| Glc$_{II}$-4 | 71.5-71.6€ | ~3.30 m |
| Glc$_{II}$-5 | 77.2 | 3.40 m |
| Glc$_{II}$-6 | 69.7 | 3.80 m, 4.05 m |
| Glc$_V$-1 | 104.8 | 4.42 d (7.8) |
| Glc$_V$-2 | 75.1-75.6¥ | 3.19 m |
| Glc$_V$-3 | 77.9-78.2§ | 3.35 m |
| Glc$_V$-4 | 71.5-71.6€ | ~3.28 m |
| Glc$_V$-5 | 77.9-78.2§ | ~3.26 m |
| Glc$_V$-6 | 62.7† | 3.66 m, 3.85 m |

¥Four carbon resonances in the range of 75.1-75.6 ppm (75.09, 75.18 and 75.56 ppm; two carbons overlap at 75.18 ppm), hence chemical shifts could not be unequivocally assigned.
§Seven carbon resonances in the range of 77.9-78.2 ppm (77.92, 77.99, 78.04, 78.13 and 78.19 ppm; two additional carbons overlap in this region), hence chemical shifts could not be unequivocally assigned.
€Four carbon resonances in the range of 71.5-71.6 ppm (71.54, 71.57, 71.59 and 71.63 ppm), hence chemical shifts could not be unequivocally assigned.
†Two carbon resonances overlap at 62.7 ppm.

A summary of the $^1$H and $^{13}$C chemical shifts for the glycoside at C-24 are found in Table 15.

TABLE 15

$^1$H and $^{13}$C NMR (500 and 125 MHz, CD$_3$OD), assignments of the C-24 glycoside.

| Position | $^{13}$C | $^1$H |
|---|---|---|
| Glc$_I$-1 | 104.2 | 4.44 d (7.1) |
| Glc$_I$-2 | 81.1 | 3.61 m |
| Glc$_I$-3 | 78.8 | 3.60 m |
| Glc$_I$-4 | 72.0 | 3.26 m |
| Glc$_I$-5 | 76.6 | 3.54 m |
| Glc$_I$-6 | 70.8 | 3.53 m, 4.28 m |
| Glc$_{II}$-1 | 104.7 | 4.29 d (~7.4) |
| Glc$_{II}$-2 | 75.1-75.6¥ | 3.22 m |
| Glc$_{II}$-3 | 77.5 | 3.37 m |
| Glc$_{II}$-4 | 71.5-71.6€ | 3.32 m |
| Glc$_{II}$-5 | 77.1 | 3.46 m |
| Glc$_{II}$-6 | 69.9 | 3.77 m, 4.14 m |
| Glc$_{III}$-1 | 104.5 | 4.78 d (7.8) |
| Glc$_{III}$-2 | 75.7 | 3.27 m |
| Glc$_{III}$-3 | 77.9-78.2§ | 3.36 m |
| Glc$_{III}$-4 | 72.3 | 3.21 m |
| Glc$_{III}$-5 | 77.9-78.2§ | 3.27 m |
| Glc$_{III}$-6 | 63.5 | 3.63 m, 3.86 m |
| Glc$_{VII}$-1 | 104.9 | 4.37 d (7.8) |
| Glc$_{VII}$-2 | 75.1-75.6¥ | 3.20 m |
| Glc$_{VII}$-3 | 77.9-78.2§ | 3.35 m |
| Glc$_{VII}$-4 | 71.5-71.6€ | 3.28 m |
| Glc$_{VII}$-5 | 77.9-78.2§ | 3.26 m |
| Glc$_{VII}$-6 | 62.7† | 3.66 m, 3.85 m |

¥Four carbon resonances in the range of 75.1-75.6 ppm (75.09, 75.18 and 75.56 ppm; two carbons overlap at 75.18 ppm), hence chemical shifts could not be unequivocally assigned.
€Four carbon resonances in the range of 71.5-71.6 ppm (71.54, 71.57, 71.59 and 71.63 ppm), hence chemical shifts could not be unequivocally assigned.
§Seven carbon resonances in the range of 77.9-78.2 ppm (77.92, 77.99, 78.04, 78.13 and 78.19 ppm; two additional carbons overlap in this region), hence chemical shifts could not be unequivocally assigned.
†Two carbon resonances overlap at 62.7 ppm.

The structure of CC-00403 was determined to be mogrol-3-O-[β-D-glucopyranosyl (1→6)-β-D-glucopyranoside]-24-O-{[β-D-glucopyranosyl-(1→2)]-[β-D-glucopyranosyl-(1→6)-(β-D-glucopyranosyl-(1→6)]-β-D-glucopyranoside}. The compound is an isomer of Mogroside VI, which differs by the linkage of a glucose unit (GlcVII) which is attached to GlcII via 1→6 sugar linkage, thus bearing three 1→6 sugar linkages in the structure.

Example 3: Preparation, Purification and Characterization of CC-00436

Preparation of Dextrin Dextranase Enzyme Preparation

Freeze dried cells from *Acetobacter capsulatus* ATCC 11894 were grown in Petri-dishes containing 3 g/L of Peptone from casein (pancreatic digest), 25 g/L of mannitol, 5 g/L of yeast extract and 15 g/L of Agar-Agar. Selected cells were picked and grown in a 1 L shake flask containing 200 mL of a the following medium: 3 g/L of Peptone from casein (pancreatic digest), 5 g/L of yeast extract and 1% of glycerol. After 30 h, the preculture was used to start productions (3 vol % of preculture used) in 14 shake flasks containing 400 mL of the same medium. After 40 h (OD600=3.3; pH=4.36) the cells (29 g Cell Wet Weight) were harvested and stored at −20° C. The cells were suspended in 200 mL of 10 mM sodium acetate buffer pH 4.8 and mechanically lysed. The supernatant was stored at −20° C.

Dextrin Dextranase Catalyzed Conversion of Mogroside V: Sample S19N1

In a 1 L Schott flask were introduced 390 mL of water, 60 mL of 0.1 M sodium acetate buffer pH 4.8, 60 mL of 10 mM Mogroside V aqueous solution, 30 g dextrin-10 (from maize starch). The reaction mixture was allowed to stir for 15 min at 40° C. before the reaction was started by adding 60 mL of Dextrin Dextranase preparation (total volume 600 mL).

At regular times, a 100 μL aliquot was taken and quenched by adding 75 μL of 2 N H$_2$SO$_4$ and 825 μL of 80%

MeOH. After centrifugation of the quenched sample, 800 µL was transferred to an HPLC vial and analyzed.

After 24 h, the reaction was quenched by adding 2 N HCl until pH 3 was reached. 600 mL of ethanol was added and the obtained suspension was allowed to stand overnight at −20° C. After centrifugation, the volume of the supernatant was reduced to 250 mL under reduced pressure. The volume was adjusted with water to 600 mL and 30 g of Diaion HP-20 was added. After stirring for 1 h the suspension was filtered and the resin was washed twice for 1 h with 100 mL of water. Desorption was performed with three times 100 mL of 80% ethanol. The combined ethanolic phases were evaporated to dryness.

HPLC Analysis. HPLC analyses were performed on a Waters 2695 Alliance System coupled to a Waters 996 Photo Diode Array (PDA) detector. In addition, sample purities were assessed using an ESA Corona Plus Charged Aerosol Detector (CAD). Sample analyses were performed using the method conditions described in Tables 16 and 17.

TABLE 16

Analytical HPLC Conditions for Fraction Analysis in Primary and Secondary Process

| Parameter | Description |
| --- | --- |
| Column (Dimensions) | Phenomenex Synergi Hydro RP (4.6 × 250 mm, 4 µm) |
| Column Temperature (° C.) | Ambient |
| Sample Temperature (° C.) | Ambient |
| Mobile Phases | (A) Water |
|  | (B) Acetonitrile (MeCN) |
| Flow Rate (mL/min) | 1.0 |
| Detection | UV at 210 nm and CAD |

| Gradient | | |
| --- | --- | --- |
| Time (min) | % A | % B |
| 0.0-40.0 | 80 | 20 |
| 40.01-47.0 | 10 | 90 |
| 47.01-57.0 | 80 | 20 |

TABLE 17

Analytical HPLC Conditions for Final Purity Analysis

| Parameter | Description |
| --- | --- |
| Column (Dimensions) | Phenomenex Synergi Hydro RP (4.6 × 250 mm, 4 µm) |
| Column Temperature (° C.) | 55 |
| Sample Temperature (° C.) | Ambient |
| Mobile Phases | (A) 0.0284% Ammonium Acetate (NH$_4$OAc) and 0.0116% Acetic Acid (HOAc) in Water |
|  | (B) MeCN |
| Flow Rate (mL/min) | 1.0 |
| Detection | UV at 210 nm and CAD |

| Gradient | | |
| --- | --- | --- |
| Time (min) | % A | % B |
| 0.0 | 85 | 15 |
| 28.5 | 75 | 25 |
| 30.0 | 71 | 29 |
| 36.5 | 70 | 30 |
| 38.5-44.5 | 66 | 34 |
| 46.5-49.0 | 48 | 52 |
| 51.0-57.0 | 30 | 70 |
| 58.0 | 85 | 15 |

Primary Preparative HPLC Method. The primary processing of Lot #GM-3502-137 (from bioconversion) was performed using a Phenomenex Synergi Hydro RP column (50×250 mm, 10 µm). The purification process was performed using a Waters Delta Prep 2000/4000 system coupled to a Waters 2487 UV-Vis detector. Details of the preparative methods are summarized in Table 18.

TABLE 18

Conditions for Primary Preparative HPLC Method.

| Parameter | Description |
| --- | --- |
| Column (Dimensions) | Phenomenex Synergi Hydro RP (50 × 250 mm, 10 µm) |
| Flow Rate (mL/min) | 118.0 |
| Detection | UV at 210 nm |
| Mobile Phases | (A) 80:20 Water/MeCN |
|  | (B) 10:90 Water/MeCN |
| Sample Preparation | 1 g dissolved in 25 mL Water |
| Gradient | Isocratic hold of 100% MP-A for 35 min, then 7 min flush of 100% MP-B |

Secondary Preparative HPLC Method. The secondary processing was performed using a Phenomenex Synergi Hydro RP (50×250 mm, 10 µm). The purification process was performed with a Waters Delta Prep LC Model 2000/4000 system coupled to a Waters 2487 UV-Vis detector. Details of the preparative method are summarized in Table 19.

TABLE 19

Conditions for Secondary Preparative HPLC Method.

| Parameter | Description |
| --- | --- |
| Column (Dimensions) | Phenomenex Synergi Hydro RP (50 × 250 mm, 10 µm) |
| Flow Rate (mL/min) | 118.0 |
| Detection | UV at 210 nm |
| Mobile Phases | (A) 80:20 Water/MeCN |
|  | (B) 10:90 Water/MeCN |
| Sample Preparation | 28 mg dissolved in 5 mL of Water |
| Gradient: | Isocratic hold of 100% MP-A for 27 min, then 7 min flush of 100% MP-B |

Isolation Procedure. Fractions collected during the final pre-concentration step were concentrated in vacuo using a Buchi® Rotary Evaporator, Model R-114. The concentrated solution was dried for 48 h using the LabConco Freezone Personal Freeze Dryer.

MS and MS/MS. MS and MS/MS data were generated with a Waters QTof Micro mass spectrometer equipped with an electrospray ionization source. The sample was analyzed by negative ESI. The sample (-0.2 mg) was diluted with 50:50 ACN:H$_2$O to a concentration of ~0.2 mg/mL and introduced via direct infusion.

NMR. The sample was prepared by dissolving 2.6 mg in 150 µL of CD$_3$OD and NMR data were acquired on a Bruker Avance 500 MHz instrument equipped with a 2.5 mm inverse probe and a 5 mm broad band probe. The $_1$H NMR spectrum was referenced to the CHD$_2$OD resonance at δH 3.30 ppm and $^{13}$C NMR spectrum was referenced to the CD$_3$OD resonance at δC 49.0 ppm.

Results and Discussion

Primary Purification. Approximately 1 g of Lot #GM-3502-137 (from the bioconversion) was processed using the primary preparative HPLC method described above. Fractions were analyzed using the analytical method summarized above. Collected fraction Lot #RAD-D-178(5) was selected for reprocessing, with a retention time of approximately 26 min on the respective preparative HPLC trace.

Secondary Purification. Fraction Lot #RAD-D-178(5) was reprocessed using the conditions described above. Fractions were analyzed using the analytical method summarized above. Collected fraction Lot #RAD-E-15(2), retention time approximately 25.5 min on the respective preparative HPLC trace, was deemed sufficiently pure for structural elucidation via NMR.

Final Batch Preparation. Fraction Lot #RAD-E-15(2) was concentrated by rotary evaporation and further dried via lyophilization for 48 hours. The final yield of the batch RAD-E-15(2) was 14.5 mg. The final purity was determined using the analytical method summarized above and found to be 93.8% (AUC, CAD) with a retention time of 25.505 min and >99.0% (AUC, UV) with a retention time of 25.443 min.

Mass Spectrometry. The ESI-TOF mass spectrum acquired by infusing a sample of CC-00436 showed a [M–H]$^-$ ion at m/z 1447.6969. The mass of the [M–H]$^-$ ion was in good agreement with the molecular formula $C_{66}H_{112}O_{34}$ (calcd for $C_{66}H_{111}O_{34}$: 1447.6957, error: 0.8 ppm) expected. The MS data confirmed that CC-00436 has a nominal mass of 1448 Daltons with the molecular formula, $C_{66}H_{112}O_{34}$. The ions observed at m/z 1545.6672 and 1561.6936 were most likely due to [M–H+$H_3PO_4$]$^-$ and [M–H+$CF_3COOH$]$^-$, respectively.

The MS/MS spectrum of CC-00436, selecting the [M–H]$^-$ ion at m/z 1447.7 for fragmentation, indicated sequential loss of six glucose units at m/z 1285.6796, 1123.6262, 961.5189, 799.5070, 637.4470 and 475.3841 indicated presence of six glucose units in the structure. Following the loss of one sugar from the structure another fragmentation pathway was also observed in the spectrum which corresponded to loss of water molecule from the central triterpene core to give m/z 1267.7117 followed by sequential loss of four glucose units at m/z 1105.6084, 943.4576, 781.5140 and 619.4249.

NMR Spectroscopy. A series of NMR experiments including $^1$H NMR, $^{13}$C NMR, $^1$H-$^1$H COSY, HSQC-DEPT, HMBC, ROESY, and 1D TOCSY were acquired to allow assignment of CC-00436.

The 1D and 2D NMR data indicated that the central core of the glycoside is a triterpene. A summary of the $^1$H and $^{13}$C chemical shifts for the aglycone are found in Table 20.

TABLE 20

$^1$H and $^{13}$C NMR (500 and 125 MHz, CD$_3$OD), assignments of the CC-00436 aglycone.

| Position | $^{13}$C | $^1$H |
|---|---|---|
| 1 | 27.2 | 1.48 m |
|  |  | 2.22 m |
| 2 | 29.6 | 1.90 m |
|  |  | 1.95 m |
| 3 | 88.3 | 3.45 m |
| 4 | 42.9 | — |
| 5 | 145.1 | — |
| 6 | 119.6 | 5.48 brd (5.9) |
| 7 | 25.1 | 1.80 m |
|  |  | 2.38 m |
| 8 | 44.6 | 1.66 m |
| 9 | 40.9 | — |
| 10 | 37.2 | 2.49 brd (11.8) |
| 11 | 79.4 | 3.85 m |
| 12 | 41.1 | 1.81 m |
|  |  | 1.87 m |
| 13 | 48.3 | — |
| 14 | 50.6 | — |
| 15 | 35.4 | 1.13 m |
|  |  | 1.21 m |

TABLE 20-continued $^1$H and $^{13}$C NMR (500 and 125 MHz, CD$_3$OD), assignments of the CC-00436 aglycone.

| Position | $^{13}$C | $^1$H |
|---|---|---|
| 16 | 29.4 | 1.33 m |
|  |  | 1.99 m |
| 17 | 51.8 | 1.62 m |
| 18 | 17.1 | 0.91 s |
| 19 | 26.2 or 26.3 | 1.10 s |
| 20 | 37.5 | 1.45 m |
| 21 | 19.3 | 0.97 d (6.3) |
| 22 | 34.1 | 1.48 m |
|  |  | 1.56 m |
| 23 | 29.9 | 1.39 m |
|  |  | 1.55 m |
| 24 | 93.2 | 3.39 m |
| 25 | 73.8$^A$ | — |
| 26 | 26.8$^†$ | 1.11 s$^†$ |
| 27 | 24.2$^†$ | 1.14 s$^†$ |
| 28 | 28.0 | 1.07 s |
| 29 | 26.2 or 26.3 | 1.18 s |
| 30 | 20.0 | 0.88 s |

$^†$Assignments can be interchanged.
$^A$Two carbon resonances overlap at 73.8 ppm (C-25 and Glc$_{VII}$ H-2).

A summary of the $^1$H and $^{13}$C chemical shifts for the glycoside at C-3 are found in Table

TABLE 21

$^1$H and $^{13}$C NMR (500 and 125 MHz, CD$_3$OD), assignments of the CC-00436 C-3 glycoside.

| Position | $^{13}$C | $^1$H |
|---|---|---|
| Glc$_{IV}$-1 | 106.4 | 4.28 d (7.7) |
| Glc$_{IV}$-2 | 75.6 | 3.19 m |
| Glc$_{IV}$-3 | 77.7-78.1$^§$ | ~3.31 m |
| Glc$_{IV}$-4 | 71.6-71.7$^ε$ | ~3.31 m |
| Glc$_{IV}$-5 | 77.2 | 3.41 m |
| Glc$_{IV}$-6 | 70.1 or 70.2 | 3.80 m, 4.05 m |
| Glc$_V$-1 | 105.1 | 4.44 d (7.8) |
| Glc$_V$-2 | 75.2$^¥$ | 3.21 m |
| Glc$_V$-3 | 77.7-78.1$^§$ | 3.36 m |
| Glc$_V$-4 | 71.4 | 3.41 m |
| Glc$_V$-5 | 76.4 or 76.5 | 3.44 m |
| Glc$_V$-6 | 67.2 | 3.72 m |
|  |  | 3.95 dd (10.8, 4.3) |
| Glc$_{VII}$-1 | 99.9 | 4.85 d (3.6¶) |
| Glc$_{VII}$-2 | 73.8$^A$ | 3.36 m |
| Glc$_{VII}$-3 | 75.2$^¥$ | 3.65 m |
| Glc$_{VII}$-4 | 71.6-71.7$^ε$ | 3.32 m |
| Glc$_{VII}$-5 | 73.5 | 3.66 m |
| Glc$_{VII}$-6 | 62.5 | 3.68 m, 3.79 m |

$^§$Six carbon resonances in the range of 77.7-78.1 ppm (77.68, 77.92, 77.96, 78.07, 78.08 and 78.14 ppm), hence chemical shifts could not be unequivocally assigned.
$^ε$Four carbon resonances in the range of 71.6-71.7 ppm (71.55, 71.60 and 71.69 ppm; one additional carbon overlap in this region), hence chemical shifts could not be unequivocally assigned.
$^¥$Three carbon resonances observed at 75.2 ppm (75.17 and 75.24 ppm; one additional carbon overlap at 75.17 ppm), hence chemical shifts could not be unequivocally assigned.
$^A$Two carbon resonances overlap at 73.8 ppm (C-25 and Glc$_{VII}$ H-2).
¶Value based on $^1$H NMR data acquired at 294K.

A summary of the $^1$H and $^{13}$C chemical shifts for the glycoside at C-24 are found in Table 22.

TABLE 22

$^1$H and $^{13}$C NMR (500 and 125 MHz, CD$_3$OD), assignments of the CC-00436 C-24 glycoside.

| Position | $^{13}$C | $^1$H |
|---|---|---|
| Glc$_I$-1 | 104.1 | 4.43 d (7.2) |
| Glc$_I$-2 | 81.3 | 3.61 m |
| Glc$_I$-3 | 78.6 | 3.59 m |

TABLE 22-continued $^1$H and $^{13}$C NMR (500 and 125 MHz, CD$_3$OD), assignments of the CC-00436 C-24 glycoside.

| Position | $^{13}$C | $^1$H |
|---|---|---|
| Glc$_I$-4 | 71.6-71.7$^\epsilon$ | 3.33 m |
| Glc$_I$-5 | 76.4 or 76.5 | 3.50 m |
| Glc$_I$-6 | 70.1 or 70.2 | 3.62 m, 4.23 m |
| Glc$_{II}$-1 | 104.4 | 4.28 d (7.7) |
| Glc$_{II}$-2 | 75.2$^\Psi$ | 3.21 m |
| Glc$_{II}$-3 | 77.7-78.1$^\S$ | 3.36 m |
| Glc$_{II}$-4 | 71.6-71.7$^\epsilon$ | ~3.27 m |
| Glc$_{II}$-5 | 77.7-78.1$^\S$ | ~3.26 m |
| Glc$_{II}$-6 | 62.7 | 3.65 m, 3.85 m |
| Glc$_{III}$-1 | 104.5 | 4.77 d (7.8) |
| Glc$_{III}$-2 | 75.7 | 3.27 m |
| Glc$_{III}$-3 | 77.7-78.1$^\S$ | 3.36 m |
| Glc$_{III}$-4 | 72.4 | 3.21 m |
| Glc$_{III}$-5 | 77.7-78.1$^\S$ | 3.27 m |
| Glc$_{III}$-6 | 63.6 | 3.63 m, 3.86 m |

$^\epsilon$Four carbon resonances in the range of 71.6-71.7 ppm (71.55, 71.60 and 71.69 ppm; one additional carbon overlap in this region), hence chemical shifts could not be unequivocally assigned.
$^\Psi$Three carbon resonances observed at 75.2 ppm (75.17 and 75.24 ppm; one additional carbon overlap at 75.17 ppm), hence chemical shifts could not be unequivocally assigned.
$^\S$Six carbon resonances in the range of 77.7-78.1 ppm (77.68, 77.92, 77.96, 78.07, 78.08 and 78.14 ppm), hence chemical shifts could not be unequivocally assigned.

The structure of CC-00436 was determined to be mogro-3-O-[α-D-glucopyranosyl-(1→6)-β-D-glucopyranosyl(1→6)-β-D-glucopyranoside]-24-O-{[β-D-glucopyranosyl-(1→2)]-[β-D-glucopyranosyl-(1→6)]-β-D-glucopyranoside}. This compound is related to Mogroside V but differs from it by an additional glucose unit (GlcVII) attached to GlcV by 1→6 α-sugar linkage.

The compound was subsequently isolated from Luo Han Guo extract (TATE & LYLE; Identification number: 3502-149-1) and its structure confirmed by the comparison of its NMR data with the data of the bioconversion compound.

Example 4: Preparation, Isolation and Characterization of CC-00367

1.287 g of Mogroside V and 1.82 g of α-D-glucose-1-fluoride (Carbosynth; MG09102) were dissolved in 70 mL of 142 mM Potassium Phosphate buffer pH 7.5. To this clear solution at 35° C. was added 30 mL of Beta-galactosidase (variant from *Streptomyces* sp; single mutation in the protein sequence, wherein the glutamic acid at position 383 is changed to alanine; EC:3.2.1.23; UniProtKB-Q59976) (SEQ. ID 2) in three portions (first portion at the beginning of the reaction, the second portion after 6 h of reaction, the third portion after 22 h of reaction).

SEQ. ID 2:
1 mvpaaqqtat apdaaltfpe gflwgsatas yqiegaaaed grtpsiwdty artpgrvrng
61 dtgdvatdhy hrwredvalm aelglgayrf slawpriqpt grgpalqkgl dfyrrladel
121 lakgiqpvat lyhwdlpqel enpggwperp taerfaeyaa iaadalgdrv ktwttlnepw
181 csaflgygsg vhapgrtdpv aalraahhln lghglavgal rdrlpadaqc svtlnihhvr
241 pltdseadad avrridalan rvftgpmlqg aypedlvkdt agltdwsfvr dgdlrlahqk
301 ldflgvnyys ptlvseadgs gthnsdghgr sahspwpgad rvafhqppge ttamgwavdp
361 sglyellrrl ssdfpalply itangaafhd yadpegnvnd periayvrdh laavhraikd
421 gsdvrgyflw slldnfewah gyskrfgavy vdyptgtrip kasarwyaev artgvlpta At regular times 125 μL samples were taken and quenched with 125 μL of 80% MeOH. 100 μL of this quenched solution was diluted with 900 μL of 50% MeOH and centrifuged at 13000 rpm for 5 min. The supernatant of this solution was analyzed by HPLC. After 30 hours, 100 mL of ethanol was added to the reaction mixture. After standing overnight at −20° C., the suspension was centrifuged and the supernatant was evaporated under reduced pressure to approximately 50 mL. The volume was readjusted with water to 100 mL and 15 g of Diaion HP-20 resin was added. After stirring the suspension for 1 hour, the beads were recovered by filtration and washed twice with 50 mL of water (contact time 1 hour/washing). Subsequently, the beads were treated three times with 50 mL of 80% ethanol (contact time 1 hour/washing). The combined ethanoic phases were evaporated to dryness under reduced pressure to provide Lot #GM-3502-024.

HPLC Analysis. HPLC analyses were performed on a Waters 2695 Alliance System coupled to a Waters 996 Photo Diode Array (PDA) detector. In addition, sample purities were assessed using an ESA Corona Charged Aerosol Detector (CAD). Sample analyses were performed using the method conditions described in Tables 23 and 24.

TABLE 23

Analytical HPLC Conditions for Fraction Analysis in Primary Process

| | |
|---|---|
| Column | Waters Atlantis dC18 (4.6 × 250 mm, 5 μm) |
| Column Temperature (° C.) | Ambient |
| Sample Temperature (° C.) | Ambient |
| Mobile Phases | (A) Water |
| | (B) Acetonitrile (MeCN) |
| Flow Rate (mL/min) | 1.0 |
| Detection | CAD and UV at 210 nm |

Gradient

| Time (min) | % A | % B |
|---|---|---|
| 0.0-40.0 | 77 | 23 |
| 40.01-47.0 | 10 | 90 |
| 47.01-57.0 | 77 | 23 |

TABLE 24

Analytical HPLC Conditions for Final Purity Analysis

| | |
|---|---|
| Column | Phenomenex Synergi Hydro RP (4.6 × 250 mm, 4 μm) |
| Column Temperature (° C.) | 55 |
| Sample Temperature (° C.) | Ambient |
| Mobile Phases | (A) 0.0284% Ammonium Acetate (NH$_4$OAc) and 0.0116% Acetic Acid (HOAc) in Water |
| | (B) MeCN |
| Flow Rate (mL/min) | 1.0 |
| Detection | CAD and UV at 210 nm |

Gradient

| Time (min) | % A | % B |
|---|---|---|
| 0.0 | 85 | 15 |
| 28.5 | 75 | 25 |
| 30.0 | 71 | 29 |
| 36.5 | 70 | 30 |
| 38.5-44.5 | 66 | 34 |
| 46.5-49.0 | 48 | 52 |
| 51.0-57.0 | 30 | 70 |
| 58.0 | 85 | 15 |

Primary Preparative HPLC Method. The primary processing of Lot #GM-3502-024 was performed using a pre-packed Waters Atlantis dC18 column (50×250 mm, 10 μm). The purification process was performed using a Waters 2545 Quaternary Gradient Module (QGM) system coupled to a Waters 2489 UV-Vis detector. Details of the preparative method are summarized in Table 25.

TABLE 25

Conditions for Primary Preparative HPLC Method.

| | |
|---|---|
| Column | Waters Atlantis dC18 (50 × 250 mm, 10 μm) |
| Flow Rate (mL/min) | 118.0 |
| Detection | UV at 210 nm |
| Mobile Phases | (A) 77:23 Water/MeCN |
| | (B) MeCN |
| Sample Preparation | 635 mg dissolved in 20 mL of MP-A |
| Gradient: | Isocratic 100% MP-A for 30 min |

Isolation Procedure. Fractions collected during the final pre-concentration step were filtered through a stainless steel sieve and concentrated in vacuo using a Buchi® Rotary Evaporator, Model R-114. The concentrated solution was dried for 48-72 h using the Kinetics Flexi-Dry Personal Freeze Dryer.

MS and MS/MS. MS and MS/MS data were generated with a Waters QTof Micro mass spectrometer equipped with an electrospray ionization source. The sample was analyzed by negative ESI. The sample (0.1 mg) was diluted with 50:50 ACN:$H_2O$ to a concentration of 25 μg/mL and introduced via direct infusion.

NMR. The sample was prepared by dissolving 2.7 mg in 150 μL of $CD_3OD$ and NMR data were acquired on a Bruker Avance 500 MHz instrument equipped with a 2.5 mm inverse probe and a 5 mm broad band probe. The $^1H$ NMR spectrum was referenced to the $CHD_2OD$ resonance at $\delta_H$ 3.30 ppm and $^{13}C$ NMR spectrum was referenced to the $CD_3OD$ resonance at $\delta_C$ 49.0 ppm.

Results and Discussion

Primary Purification. Approximately 635 mg of Lot #GM-3502-024 was processed using the primary preparative HPLC method described above. Fractions were analyzed using the analytical method summarized above and fraction Lot #RAD-D-80(1) was found to be sufficiently pure for NMR analysis, retention time approximately 8.50 min on the preparative trace.

Final Batch Preparation. Fraction Lot #RAD-D-80(1) was concentrated by rotary evaporation for final isolation. The concentrated solution was further dried via lyophilization for 48 hours. The final yield of the batch RAD-D-80(1) was 9.3 mg. The final purity was determined using the analytical method summarized above and found to be 32.3% (AUC, CAD) with a retention time of 21.888 min and >99.0% (AUC, UV) with a retention time of 21.825 min.

Mass Spectrometry. The ESI-TOF mass spectrum acquired by infusing a sample of CC-00367 showed a [M–H]$^-$ ion at m/z 1447.6395. The mass of the [M–H]$^-$ ion was in good agreement with the molecular formula $C_{66}H_{112}O_{34}$ (calcd for $C_{66}H_{111}O_{34}$: 1447.6957, error: 5.4 ppm) expected.

The MS data confirmed that CC-00367 has a nominal mass of 1448 Daltons with the molecular formula, $C_{66}H_{112}O_{34}$. The ion observed at m/z 1561.7018 is most likely due to [M–H+$CF_3COOH$]$^-$ The MS/MS spectrum of CC-00367, selecting the [M–H]$^-$ ion at m/z 1447.0 for fragmentation, indicated sequential loss of six glucose units at m/z 1285.5913, 1123.5566, 961.5007, 799.4480, 637.4036, and 475.3371 indicated presence of six glucose units in the structure. Following the loss of one sugar from the structure another fragmentation pathway was also observed in the spectrum which corresponded to loss of water molecule from the central triterpene core to give m/z 1267.5607 followed by sequential loss of four glucose units at m/z 1105.5161, 943.4819, 781.4854 and 619.4509. The ion observed at m/z 383.0884 was most likely due to the loss of six glucose and C-24 isopropyl hydroxyl units.

NMR Spectroscopy. A series of NMR experiments including $^1H$ NMR, $^{13}C$ NMR, $^1H$-$^1H$ COSY, HSQC-DEPT, HMBC, ROESY, and 1D TOCSY were acquired to allow assignment of CC-00367.

A summary of the $^1H$ and $^{13}C$ chemical shifts for the glycoside at C-3 are found in Table 26.

TABLE 26

$^1H$ and $^{13}C$ NMR (500 and 125 MHz, $CD_3OD$), assignments of the aglycone.

| Position | $^{13}C$ | $^1H$ |
|---|---|---|
| 1 | 27.2 | 1.49 m |
| | | 2.22 m |
| 2 | 29.7 | 1.91 m |
| | | 1.98 m |
| 3 | 88.2 | 3.47 m |
| 4 | 42.9 | — |
| 5 | 145.0 | — |
| 6 | 119.6 | 5.49 brd (5.3) |
| 7 | 25.1 | 1.81 m |
| | | 2.39 m |
| 8 | 44.7 | 1.67 m |
| 9 | 40.9 | — |
| 10 | 37.3 | 2.49 brd (11.5) |
| 11 | 79.5 | 3.85 m |
| 12 | 41.1 | 1.81 m |
| | | 1.87 m |
| 13 | 48.3 | — |
| 14 | 50.6 | — |
| 15 | 35.4 | 1.14 m |
| | | 1.21 m |
| 16 | 29.4 | 1.33 m |
| | | 1.99 m |
| 17 | 51.7 | 1.62 m |
| 18 | 17.2 | 0.92 s |
| 19 | 26.2 or 26.3 | 1.11 s |
| 20 | 37.4 | 1.46 m |
| 21 | 19.4 | 0.97 d (6.2) |
| 22 | 34.1 | 1.48 m |
| | | 1.55 m |
| 23 | 29.9 | 1.40 m |
| | | 1.56 m |
| 24 | 93.1 | 3.39 m |
| 25 | 73.8 | — |
| 26 | 26.8† | 1.11 s† |
| 27 | 24.2† | 1.14 s† |
| 28 | 28.1 | 1.08 s |
| 29 | 26.2 or 26.3 | 1.18 s |
| 30 | 19.9 | 0.88 s |

†Assignments can be interchanged.

A summary of the $^1H$ and $^{13}C$ chemical shifts for the glycoside at C-24 are found in Table 27.

TABLE 27

$^1H$ and $^{13}C$ NMR (500 and 125 MHz, $CD_3OD$), assignments of the C-24 glycoside.

| Position | $^{13}C$ | $^1H$ |
|---|---|---|
| Glc$_f$-1 | 104.0 | 4.43 d (~7.7)$^A$ |
| Glc$_f$-2 | 81.4 | 3.59 m |
| Glc$_f$-3 | 78.5 | 3.59 m |
| Glc$_f$-4 | 71.3-71.6$^e$ | 3.34 m |

TABLE 27-continued $^1$H and $^{13}$C NMR (500 and 125 MHz, CD$_3$OD), assignments of the C-24 glycoside.

| Position | $^{13}$C | $^1$H |
|---|---|---|
| Glc$_I$-5 | 76.4 or 76.5 or 76.6 | 3.50 m |
| Glc$_I$-6 | 70.1 | 3.63 m, 4.22 m |
| Glc$_{II}$-1 | 104.4 or 104.5 | 4.28 d (7.7) |
| Glc$_{II}$-2 | 75.2$^\delta$ | 3.21 m |
| Glc$_{II}$-3 | 77.7-78.2$^\S$ | 3.36 m |
| Glc$_{II}$-4 | 71.3-71.6$^\epsilon$ | ~3.27–3.29 m |
| Glc$_{II}$-5 | 77.7-78.2$^\S$ | ~3.26 m |
| Glc$_{II}$-6 | 62.5 or 62.7$^\dagger$ | 3.65 m, 3.85 m |
| Glc$_{III}$-1 | 104.4 or 104.5 | 4.77 d (7.9) |
| Glc$_{III}$-2 | 75.6$^\yen$ | 3.34 m |
| Glc$_{III}$-3 | 76.4 or 76.5 or 76.6 | 3.53 m |
| Glc$_{III}$-4 | 81.5 | 3.46 m |
| Glc$_{III}$-5 | 76.4 or 76.5 or 76.6 | 3.40 m |
| Glc$_{III}$-6 | 62.9 | 3.78 m, 3.92 m |
| Glc$_{VII}$-1 | 104.7$^\lambda$ | 4.36 d (7.8) |
| Glc$_{VII}$-2 | 74.7 | 3.25 m |
| Glc$_{VII}$-3 | 77.7-78.2$^\S$ | 3.38 m |
| Glc$_{VII}$-4 | 71.3-71.6$^\epsilon$ | 3.33 m |
| Glc$_{VII}$-5 | 77.7-78.2$^\S$ | 3.32 m |
| Glc$_{VII}$-6 | 62.5 or 62.7$^\dagger$ | 3.66 m, 3.88 m |

$^\epsilon$Five carbon resonances in the range of 71.3-71.6 ppm (71.33, 71.56, 71.59 and 71.64 ppm; two carbons at 71.64 ppm), hence chemical shifts could not be unequivocally assigned.
$^\delta$Two carbon resonances partially overlapped at 75.2 ppm (75.16 and 75.18 ppm).
$^\S$Seven carbon resonances in the range of 77.7-78.2 ppm (77.67, 77.75, 77.88, 77.91, 77.97, 78.13 and 78.17 ppm), hence chemical shifts could not be unequivocally assigned.
$^\dagger$Three carbon resonances in the range of 62.5-62.7 ppm (62.47, 62.69 and 62.73 ppm), hence chemical shifts could not be unequivocally assigned.
$^\yen$Two carbon resonances partially overlapped at 75.6 ppm (75.55 and 75.57 ppm).
$^\lambda$Two carbon resonances overlapped at 104.73 ppm.
$^A$Coupling constant based on 1D-TOCSY data.

A summary of the $^1$H and $^{13}$C chemical shifts for the glycoside at C-3 are found in Table 28.

TABLE 28

$^1$H and $^{13}$C NMR (500 and 125 MHz, CD$_3$OD), assignments of the C-3 glycoside.

| Position | $^{13}$C | $^1$H |
|---|---|---|
| GlcIv-1 | 106.3 | 4.28 d (7.7) |
| GlcIv-2 | 75.6$^\yen$ | 3.19 m |
| GlcIv-3 | 77.7-78.2$^\S$ | 3.31 m |
| GlcIv-4 | 71.3-71.6$^\epsilon$ | 3.27 m |
| GlcIv-5 | 77.3 | 3.41 m |
| GlcIv-6 | 69.7 | 3.80 m, 4.05 m |
| Glcv-1 | 104.7$^\lambda$ | 4.44 d (7.7) |
| Glcv-2 | 75.2$^\delta$ | 3.19 m |
| Glcv-3 | 77.7-78.2$^\S$ | 3.37 m |
| Glcv-4 | 71.3-71.6$^\epsilon$ | 3.29 m |
| Glcv-5 | 77.7-78.2$^\S$ | 3.26 m |
| Glcv-6 | 62.5 or 62.7$^\dagger$ | 3.66 m, 3.86 m |

$^\yen$Two carbon resonances partially overlapped at 75.6 ppm (75.55 and 75.57 ppm).
$^\S$Seven carbon resonances in the range of 77.7-78.2 ppm (77.67, 77.75, 77.88, 77.91, 77.97, 78.13 and 78.17 ppm), hence chemical shifts could not be unequivocally assigned.
$^\epsilon$Five carbon resonances in the range of 71.3-71.6 ppm (71.33, 71.56, 71.59 and 71.64 ppm; two carbons at 71.64 ppm), hence chemical shifts could not be unequivocally assigned.
$^\lambda$Two carbon resonances overlapped at 104.73 ppm.
$^\delta$Two carbon resonances partially overlapped at 75.2 ppm (75.16 and 75.18 ppm).
$^\dagger$Three carbon resonances in the range of 62.5-62.7 ppm (62.47, 62.69 and 62.73 ppm), hence chemical shifts could not be unequivocally assigned.

The structure of CC-00367 was determined to be mogro-3-O-[β-D-glucopyranosyl (1→6)-β-D-glucopyranoside]-24-O-{[(β-D-glucopyranosyl-(1→4))-β-D-glucopyranosyl-(1→2)]-[β-D-glucopyranosyl-(1→6)]-β-D-glucopyranoside}. This compound is related to Mogroside V but differs from it by an additional glucose unit (GlcVII) attached to GcIII by 1→4 sugar linkage. The compound was subsequently isolated from Luo Han Guo extract and its structure confirmed by the comparison of its NMR data with the data of the bioconversion compound.

Example 5: Preparation, Purification and Characterization of CC-00371

1.287 g of Mogroside V and 0.182 g of α-D-glucose-1-fluoride (Carbosynth; MG09102) were dissolved in 90 mL of 110 mM Potassium Phosphate buffer pH 7.0. To this clear solution at 35° C. was added 10 mL of Beta-galactosidase (variant from *Sulfolobus solfataricus*; has a single mutation in the protein sequence, wherein the glutamic acid at position 387 is changed to glycine (EC:3.2.1.23; UniProtKB-P22498)(SEQ. ID 1)).

SEQ. ID 1:
1 mysfpnsfrf gwsqagfqse mgtpgsedpn tdwykwvhdp enmaaglvsg dlpengpgyw
61 gnyktfhdna qkmglkiarl nvewsrifpn plprpqnfde skqdvtevei nenelkrlde
121 yankdalnhy reifkdlksr glyfilnmyh wplplwlhdp irvrrgdftg psgwlstrty
181 yefarfsayi awkfddlvde ystmnepnvv gglgyvgvks gfppgylsfe lsrramynii
241 qaharaydgi ksvskkpvgi iyanssfqpl tdkdmeavem aendnrwwff daiirgeitr
301 gnekivrddl kgrldwigvn yytrtvvkrt ekgyvslggy ghgcernsvs laglptsdfg
361 weffpeglyd vltkywnryh lymyvtangi addadyqrpy ylvshvyqvh rainsgadvr
421 gylhwsladn yewasgfsmr fgllkvdynt krlywrpsal vyreiatnga itdeiehlns
481 vppvkplrh At regular times 125 µL samples were taken and quenched with 125 µL of 80% MeOH. 100 mL of this quenched solution was diluted with 900 µL of 50% MeOH and centrifuged at 13000 rpm for 5 min. The supernatant of this solution was analyzed by HPLC. After 30 hours, 100 mL of ethanol was added to the reaction mixture. After standing overnight at −20° C., the suspension was centrifuged and the supernatant was evaporated under reduced pressure to approximately 50 mL. The volume was readjusted with water to 100 µL and 15 g of Diaion HP-20 resin was added. After stirring the suspension for 1 hour, the beads were recovered by filtration and washed twice with 50 mL of water (contact time 1 hour/washing).

Subsequently, the beads were treated three times with 50 mL of 80% ethanol (contact time 1 hour/desorption). The combined ethanoic phases were evaporated to dryness under reduced pressure to provide Lot #GM-3502-038.

HPLC Analysis. HPLC analyses were performed on a Waters 2695 Alliance System coupled to a Waters 996 Photo Diode Array (PDA) detector. In addition, sample purities were assessed using an ESA Corona Charged Aerosol Detector (CAD). Sample analyses were performed using the method conditions described in Tables 29-33.

TABLE 29

Analytical HPLC Conditions for Fraction Analysis in Primary Process

| | |
|---|---|
| Column | Waters Atlantis dC18 (4.6 × 250 mm, 5 µm) |
| Column Temperature (° C.) | Ambient |
| Sample Temperature (° C.) | Ambient |
| Mobile Phases | (A) Water |
| | (B) Acetonitrile (MeCN) |
| Flow Rate (mL/min) | 1.0 |
| Detection | CAD and UV at 210 nm |

TABLE 29-continued

Analytical HPLC Conditions for Fraction Analysis in Primary Process

Gradient

| Time (min) | % A | % B |
|---|---|---|
| 0.0-40.0 | 77 | 23 |
| 40.01-47.0 | 10 | 90 |
| 47.01-57.0 | 77 | 23 |

TABLE 30

Analytical HPLC Conditions for Fraction Analysis in Secondary Process

| | |
|---|---|
| Column | Waters XBridge Amide (4.6 × 150 mm, 3.5 μm) |
| Column Temperature (° C.) | Ambient |
| Sample Temperature (° C.) | Ambient |
| Mobile Phases | (A) Water |
| | (B) Acetonitrile (MeCN) |
| Flow Rate (mL/min) | 1.0 |
| Detection | CAD and UV at 210 nm |

Gradient

| Time (min) | % A | % B |
|---|---|---|
| 0.0-40.0 | 25 | 75 |
| 40.01-47.0 | 90 | 10 |
| 47.01-57.0 | 25 | 75 |

TABLE 30

Analytical HPLC Conditions for Fraction Analysis in Secondary Process

| | |
|---|---|
| Column | Waters XBridge Amide (4.6 × 150 mm, 3.5 μm) |
| Column Temperature (° C.) | Ambient |
| Sample Temperature (° C.) | Ambient |
| Mobile Phases | (A) Water |
| | (B) Acetonitrile (MeCN) |
| Flow Rate (mL/min) | 1.0 |
| Detection | CAD and UV at 210 nm |

Gradient

| Time (min) | % A | % B |
|---|---|---|
| 0.0-40.0 | 25 | 75 |
| 40.01-47.0 | 90 | 10 |
| 47.01-57.0 | 25 | 75 |

TABLE 32

Analytical HPLC Conditions for Fraction Analysis in Quaternary Process

| | |
|---|---|
| Column | Waters XBridge Phenyl (4.6 × 150 mm, 5 μm) |
| Column Temperature (° C.) | Ambient |
| Sample Temperature (° C.) | Ambient |
| Mobile Phases | (A) Water |
| | (B) Acetonitrile (MeCN) |
| Flow Rate (mL/min) | 1.0 |
| Detection | CAD and UV at 210 nm |

TABLE 32-continued

Analytical HPLC Conditions for Fraction Analysis in Quaternary Process

Gradient

| Time (min) | % A | % B |
|---|---|---|
| 0.0-40.0 | 83 | 17 |
| 40.01-47.0 | 10 | 90 |
| 47.01-57.0 | 83 | 17 |

TABLE 33

Analytical HPLC Conditions for Final Purity Analysis

| | |
|---|---|
| Column | Phenomenex Synergi Hydro RP (4.6 × 250 mm, 4 μm) |
| Column Temperature (° C.) | 55 |
| Sample Temperature (° C.) | Ambient |
| Mobile Phases | (A) 0.0284% Ammonium Acetate ($NH_4OAc$) and 0.0116% Acetic Acid (HOAc) in Water |
| | (B) MeCN |
| Flow Rate (mL/min) | 1.0 |
| Detection | CAD and UV at 210 nm |

Gradient

| Time (min) | % A | % B |
|---|---|---|
| 0.0 | 85 | 15 |
| 28.5 | 75 | 25 |
| 30.0 | 71 | 29 |
| 36.5 | 70 | 30 |
| 38.5-44.5 | 66 | 34 |
| 46.5-49.0 | 48 | 52 |
| 51.0-57.0 | 30 | 70 |
| 58.0 | 85 | 15 |

Primary Preparative HPLC Method. The primary processing of Lot #GM-3502-038 was performed using a pre-packed Waters Atlantis dC18 column (50×250 mm, 10 μm). The purification process was performed using a Waters 2545 Quaternary Gradient Module (QGM) system coupled to a Waters 2489 UV-Vis detector. Details of the preparative method are summarized in Table 34.

TABLE 34

Conditions for Primary Preparative HPLC Method.

| | |
|---|---|
| Column | Waters Atlantis dC18 (50 × 250 mm, 10 μm) |
| Flow Rate (mL/min) | 118.0 |
| Detection | UV at 210 nm |
| Mobile Phases | (A) 77:23 Water/MeCN |
| | (B) MeCN |
| Sample Preparation | 762 mg dissolved in 20 mL of MP-A |
| Gradient: | Isocratic 100% MP-A for 30 min |

Secondary and Tertiar Preparative HPLC Methods. The secondary and tertiary processing of Lot #GM-3502-038 was performed using a Waters XBridge Amide (19×250 mm, 5 μm, PN 186006606, SN 0107341600112 02) column. The purification process was preformed with a Waters Delta Prep LC Model 200/4000 system coupled to a UV-Vis detector. Details of the preparative method are summarized in Table 35 and 36.

TABLE 35

Conditions for Secondary Preparative HPLC Method.

| | |
|---|---|
| Column | Waters XBridge Amide (19 × 250 mm, 5 µm) |
| Flow Rate (mL/min) | 18.0 |
| Detection | UV at 210 nm |
| Mobile Phases | (A) 75:25 MeCN/Water |
| | (B) Water |
| Sample Preparation | 10 mL of MP-A |
| Gradient: | Isocratic 100% MP-A for 40 min |

TABLE 36

Conditions for Tertiary Preparative HPLC Method.

| | |
|---|---|
| Column | Waters XBridge Amide (19 × 250 mm, 5 µm) |
| Flow Rate (mL/min) | 18.0 |
| Detection | UV at 210 nm |
| Mobile Phases | (A) 78:22 MeCN/Water |
| | (B) Water |
| Sample Preparation | 10 mL of MP-A |
| Gradient: | Isocratic 100% MP-A for 60 min |

Quaternary Preparative HPLC Method. The quaternary processing of Lot #GM 3502-038 was performed using a Waters XBridge Phenyl (19×250 mm, 5 µm) column. The purification process was performed with a Waters Delta Prep LC Model 2000/4000 system coupled to a UV-Vis detector. Details of the preparative method are summarized in Table 37.

TABLE 37

Conditions for Quaternary Preparative HPLC Method.

| | |
|---|---|
| Column | Waters XBridge Phenyl (19 × 250 mm, 5 µm) |
| Flow Rate (mL/min) | 18.0 |
| Detection | UV at 210 nm |
| Mobile Phases | (A) 83:17 Water/MeCN |
| | (B) MeCN |
| Sample Preparation | 10 mL of MP-A |
| Gradient: | Isocratic 100% MP-A for 50 min |

Isolation Procedure. Fractions collected during the final pre-concentration step were filtered through a stainless-steel sieve and concentrated in vacuo using a Buchi® Rotary Evaporator, Model R-114. The concentrated solution was dried for 48-72 h using the Kinetics Flexi-Dry Personal Freeze Dryer.

MS and MS/MS. MS and MS/MS data were generated with a Waters QTof Micro mass spectrometer equipped with an electrospray ionization source. The sample was analyzed by negative ESI. The sample (0.2 mg) was diluted with 50:50 ACN:$H_2O$ to a concentration of 0.2 mg/mL and introduced via direct infusion.

NMR. The sample was prepared by dissolving 3.4 mg in 150 µL of $CD_3OD$ and NMR data were acquired on a Bruker Avance 500 MHz instrument equipped with a 2.5 mm inverse probe and a 5 mm broad band probe. The $^1H$ NMR spectrum was referenced to the $CHD_2OD$ resonance at $\delta_H$ 3.30 ppm and $^{13}C$ NMR spectrum was referenced to the $CD_3OD$ resonance at $\delta_C$ 49.0 ppm.

Results and Discussion

Primary Purification. Approximately 762 mg of Lot #GM-3502-038 was processed using the primary preparative HPLC method described above. Fractions were analyzed using the analytical method summarized above. Collected fraction Lot #RAD-D-83(Baseline A) and Lot #RAD-D-83 (Baseline B) (retention time 1-9 mins) were selected for reprocessing.

Secondary Purification. Fraction Lot #RAD-D-83(Baseline A) and Lot #RAD-D-83(Baseline B) were reprocessed using the conditions described above. Fractions were analyzed using the analytical method summarized above. Collected fractions Lot #RAD-D-91(3) and Lot #RAD-D-94(3) were selected for reprocessing, retention times approximately 27.000 min and 29.000 min on their respective preparative traces.

Tertiary Purification. Fraction Lot #RAD-D-94(3) was reprocessed using the conditions described above. Fractions were analyzed using the analytical method summarized above. Collected fractions Lot #RAD-D-96(3) was selected for reprocessing, retention time approximately 35.000 min on the preparative trace.

Quaternary Purification. Fraction Lot #RAD-D-91(3) and Lot #RAD-D-96(3) were reprocessed using the conditions described above. Fractions were analyzed using the analytical method summarized above. Collected fractions Lot #RAD-D-100(2) and Lot #RAD-D-100(4) were determined to be sufficiently pure for NMR studies and pooled into Lot #RAD-D-101(1), retention times approximately 50.000 min and 55.000 min on their respective preparative traces.

Final Batch Preparation. Fraction Lot #RAD-D-101(1) was concentrated by rotary evaporation for final isolation. The concentrated solution was further dried via lyophilization for 48 hours. The final yield of the batch RAD-D-101(1) was 12.9 mg. The final purity was determined using the analytical method summarized above and found to be >99.0% (AUC, CAD) with a retention time of 24.858 min and >99.0% (AUC, UV) with a retention time of 24.799 min.

Mass Spectrometry. The ESI-TOF mass spectrum acquired by infusing a sample of CC-00371 showed a $[M-H]^-$ ion at m/z 1447.7224. The mass of the $[M-H]^-$ ion was in good agreement with the molecular formula $C_{66}H_2O_{34}$ (calcd for $C_{66}H_{111}O_{34}$: 1447.6957, error: −1.1 ppm) expected. The MS data confirmed that CC-00371 has a nominal mass of 1448 Daltons with the molecular formula, $C_{66}H_{112}O_{34}$. The ions observed at m/z 1545.6931 and 723.3486 were most likely due to $[M-H+H_3PO_4]^-$ and doubly charged molecular ion $[M-2H]^{2-}$, respectively.

The MS/MS spectrum of CC-00371, selecting the $[M-H]^-$ ion at m/z 1447.0 for fragmentation, indicated sequential loss of six glucose units at m/z 1285.6511, 1123.6101, 961.5688, 799.5102, 637.4311, and 475.3878 indicated presence of six glucose units in the structure. Following the loss of one sugar from the structure an alternative fragmentation pathway was also observed in the spectrum which corresponded to loss of water molecule from the central triterpene core followed by sequential loss of glucose units at m/z 1267.6598, 1105.5859, 943.5305, 781.4700 and 619.4268. The ion observed at m/z 383.1179 was most likely due to the loss of six glucose and C-24 isopropyl hydroxyl units.

NMR Spectroscopy. A series of NMR experiments including $^1H$ NMR, $^{13}C$ NMR, $^1H$-$^1H$ COSY, HSQC-DEPT, HMBC, ROESY, and 1D TOCSY were acquired to allow assignment of CC-00371.

The 1D and 2D NMR data indicated that the central core of the glycoside is a triterpene. A summary of the $^1H$ and $^{13}C$ chemical shifts for the aglycone are found in Table 38.

TABLE 38

$^1$H and $^{13}$C NMR (500 and 125 MHz, CD$_3$OD) assignments of the aglycone.

| Position | $^{13}$C | $^1$H |
|---|---|---|
| 1 | 27.2 | 1.49 m |
|  |  | 2.22 m |
| 2 | 29.6 | 1.89 m |
|  |  | 1.94 m |
| 3 | 88.2 | 3.46 m |
| 4 | 42.9 | — |
| 5 | 145.0 | — |
| 6 | 119.6 | 5.48 brd (5.9) |
| 7 | 25.1 | 1.81 m |
|  |  | 2.38 m |
| 8 | 44.6 | 1.66 m |
| 9 | 40.9 | — |
| 10 | 37.2 | 2.49 brd (11.8) |
| 11 | 79.4 | 3.85 m |
| 12 | 41.1 | 1.81 m |
|  |  | 1.87 m |
| 13 | 48.3 | — |
| 14 | 50.6 | — |
| 15 | 35.4 | 1.13 m |
|  |  | 1.21 m |
| 16 | 29.4 | 1.33 m |
|  |  | 1.98 m |
| 17 | 51.7 | 1.62 m |
| 18 | 17.2 | 0.91 s |
| 19 | 26.2 or 26.3 | 1.10 s |
| 20 | 37.4 | 1.45 m |
| 21 | 19.3 | 0.97 d (6.2) |
| 22 | 34.1 | 1.48 m |
|  |  | 1.55 m |
| 23 | 29.8 | 1.41 m |
|  |  | 1.56 m |
| 24 | 92.5 | 3.41 m |
| 25 | 73.9 | — |
| 26 | 26.9† | 1.12 s† |
| 27 | 24.2† | 1.14 s† |
| 28 | 28.0 | 1.07 s |
| 29 | 26.2 or 26.3 | 1.18 s |
| 30 | 20.0 | 0.88 s |

†Assignments can be interchanged.

A summary of the $^1$H and $^{13}$C chemical shifts for the glycoside at C-3 are found in Table 39.

TABLE 39

$^1$H and $^{13}$C NMR (500 and 125 MHz, CD$_3$OD), assignments of the C-3 glycoside.

| Position | $^{13}$C | $^1$H |
|---|---|---|
| Glc$_{IV}$-1 | 106.4 | 4.28 d (7.8) |
| Glc$_{IV}$-2 | 75.6 or 75.7¥ | 3.19 m |
| Glc$_{IV}$-3 | 77.6-78.2§ | 3.31 m |
| Glc$_{IV}$-4 | 71.4-71.6€ | 3.29 m |
| Glc$_{IV}$-5 | 77.2 | 3.40 m |
| Glc$_{IV}$-6 | 69.7 | 3.80 m, 4.05 m |
| Glc$_I$-1 | 104.8 | 4.42 d (7.8) |
| Glc$_I$-2 | 75.2 | 3.19 m |
| Glc$_I$-3 | 77.6-78.2§ | 3.36 m |
| Glc$_I$-4 | 71.4-71.6€ | 3.29 m |
| Glc$_I$-5 | 77.6-78.2§ | 3.25 m |
| Glc$_I$-6 | 62.6 or 62.7† | 3.66 m, 3.85 m |

¥Three carbon resonances in the range of 75.6-75.7 ppm (75.55, 75.61 and 75.68 ppm), hence chemical shifts could not be unequivocally assigned.
§Eight carbon resonances in the range of 77.6-78.2 ppm (77.58, 77.81, 77.91, 77.97, 78.03, 78.12 and 78.15 ppm; one additional carbon overlapped at 78.12 or 78.15 ppm), hence chemical shifts could not be unequivocally assigned.
€Four carbon resonances in the range of 71.4-71.6 ppm (71.38, 71.54, 71.56 and 71.62 ppm), hence chemical shifts could not be unequivocally assigned.
†Three carbon resonances in the range of 62.6-62.7 ppm (62.60, 62.63 and 62.73 ppm), hence chemical shifts could not be unequivocally assigned.

A summary of the $^1$H and $^{13}$C chemical shifts for the glycoside at C-24 are found in Table 40.

TABLE 40

$^1$H and $^{13}$C NMR (500 and 125 MHz, CD$_3$OD), assignments of the C-24 glycoside.

| Position | $^{13}$C | $^1$H |
|---|---|---|
| Glc$_I$-1 | 103.9 | 4.44 d (7.7) |
| Glc$_I$-2 | 81.5 | 3.59 m |
| Glc$_I$-3 | 78.5 | 3.58 m |
| Glc$_I$-4 | 71.4-71.6€ | 3.36 m |
| Glc$_I$-5 | 76.5 | 3.49 m |
| Glc$_I$-6 | 69.9 | 3.68 m, 4.19 m |
| Glc$_{II}$-1 | 104.0 | 4.36 d (7.8) |
| Glc$_{II}$-2 | 74.6 | 3.40 m |
| Glc$_{II}$-3 | 87.5 | 3.56 m |
| Glc$_{II}$-4 | 70.0 | 3.40 m |
| Glc$_{II}$-5 | 77.6-78.2§ | 3.30 m |
| Glc$_{II}$-6 | 62.6 or 62.7† | 3.67 m, 3.86 m |
| Glc$_{III}$-1 | 104.6 | 4.74 d (7.8) |
| Glc$_{III}$-2 | 75.6 or 75.7¥ | 3.28 m |
| Glc$_{III}$-3 | 77.6-78.2§ | 3.37 m |
| Glc$_{III}$-4 | 72.3 | 3.21 m |
| Glc$_{III}$-5 | 77.6-78.2§ | 3.28 m |
| Glc$_{III}$-6 | 63.5 | 3.63 m, 3.86 m |
| Glc$_{VII}$-1 | 105.4 | 4.55 d (7.7) |
| Glc$_{VII}$-2 | 75.6 or 75.7¥ | 3.27 m |
| Glc$_{VII}$-3 | 77.6-78.2§ | 3.38 m |
| Glc$_{VII}$-4 | 71.4-71.6€ | 3.27 m |
| Glc$_{VII}$-5 | 77.6-78.2§ | 3.31 m |
| Glc$_{VII}$-6 | 62.6 or 62.7† | 3.63 m, 3.87 m |

€Four carbon resonances in the range of 71.4-71.6 ppm (71.38, 71.54, 71.56 and 71.62 ppm), hence chemical shifts could not be unequivocally assigned.
§Eight carbon resonances in the range of 77.6-78.2 ppm (77.58, 77.81, 77.91, 77.97, 78.03, 78.12 and 78.15 ppm; one additional carbon overlapped at 78.12 or 78.15 ppm), hence chemical shifts could not be unequivocally assigned.
†Three carbon resonances in the range of 62.6-62.7 ppm (62.60, 62.63 and 62.73 ppm), hence chemical shifts could not be unequivocally assigned.
¥Three carbon resonances in the range of 75.6-75.7 ppm (75.55, 75.61 and 75.68 ppm), hence chemical shifts could not be unequivocally assigned.

The structure of CC-00371 was determined to be mogro-3-O-[β-D-glucopyranosyl (1→6)-β-D-glucopyranoside]-24-O-{[β-D-glucopyranosyl-(1→2)]-[(β-D-glucopyrano-syl-(1β3))-β-D-glucopyranosyl-(1β6)]-β-D-glucopyranos-ide}. The compound is related to Mogroside V but differs from it by an additional glucose unit (GlcVII) attached to GlcII by 1β3 sugar linkage.

Example 6: Preparation, Purification and Characterization of CC-00417

Cells of *Leuconostoc* citreum DSM 20188 were grown at 23° C. in a medium that consisted of:
40 g/L of Sucrose
20 g/L of Yeast Extract (BIOKAR)
7.82 g/L of KH$_2$PO$_4$
10.02 g/L of K$_2$HPO$_4$
0.2 g/L of MgSO$_4$·7H$_2$O
0.01 g/L of MnSO$_4$·H$_2$O
0.02 g/L of CaCl$_2$·2H$_2$O
0.01 g/L of FeSO$_4$ After centrifugation, the cell pellet was stored frozen and lysed mechanically. After centrifugation, the lysate was isolated and stored at −20° C.

Activity Test of DS-DSM 20188

The activity of DSM 20188 enzyme preparation was determined by measuring the amount of reducing fructose (3,5-dinitrosalicylic acid assay) that was produced from sucrose (100 g/L) in 20 mM sodium acetate buffer pH 5.5 in the presence of 0.02 g/L CaCl$_2$) at 30° C. An activity of 2.6 U/mL was determined (1 U corresponds to the amount of supernatant that is required to produce 1 μmol of reducing sugar per minute under the assay conditions).

DSM 20188 Dextran Sucrase Catalyzed Conversion of Monk Fruit Extract MV55: Sample 41604_S14N2

In a 500 mL Schott bottle were added 15 mL of 1.0 M sodium acetate buffer pH 5.2, 30 mL of 0.5 g/L solution of $CaCl_2$), 30 mL of 12.5 mM Monk Fruit extract, 7.5 mL of 1.0 M sucrose, 50 mL of DSM 20188 enzyme preparation (2.6 U/mL) and 165 mL of water. The corresponding final concentrations were as follows: 50 mM sodium acetate buffer pH 5.2, 0.05 g/L $CaCl_2$), 1.25 mM Monk Fruit extract, 30 mM sucrose and 0.5 U/mL DSM 20188 Dextran Sucrase. This reaction mixture was allowed to stir for 24 h at 30° C. while taking 125 μL samples at regular times. These samples were quenched in 345 μL of 80% methanol and 30 μL 2N $H_2SO_4$. 300 mL of ethanol was added to quench the reaction and the resulting suspension was allowed to stand at −20° C. overnight. After centrifugation, the supernatant was concentrated on the rotary evaporator to 100 mL. After adjusting the volume to 300 mL with water, 10 g of Diaion HP-20 was added and the mixture was allowed to stir for 30 minutes. The resin was washed twice with 50 mL of water for 30 minutes and subsequent desorption of the products was performed using three times 50 mL of 80% ethanol for 30 min. The combined desorption phases were evaporated to dryness to provide Lot #GM-3502-106-8.

HPLC Analysis. HPLC analyses were performed on a Waters 2695 Alliance System coupled to a Waters 996 Photo Diode Array (PDA) detector. In addition, sample purities were assessed using an ESA Corona Plus Charged Aerosol Detector (CAD). Sample analyses were performed using the method conditions described in Table 41.

TABLE 41

Analytical HPLC Conditions for Fraction Analysis in Primary Process and Final Purity Analysis

| Column | Waters SymmetryShield RP18 (4.6 × 250 mm, 5 μm) |
|---|---|
| Column Temperature (° C.) | Ambient |
| Sample Temperature (° C.) | Ambient |
| Mobile Phases | (A) Water |
|  | (B) Acetonitrile (MeCN) |
| Flow Rate (mL/min) | 1.0 |
| Detection | UV at 210 nm and CAD |

| Gradient | | |
|---|---|---|
| Time (min) | % A | % B |
| 0.0-60.0 | 82 | 18 |
| 60.01-67.0 | 10 | 90 |
| 67.01-77.0 | 82 | 18 |

Primary Preparative HPLC Method. The primary processing of Lot #GM-3502-106-8 was performed using a pre-packed Waters SymmetryShield RP18 column (50×250 mm, 7 μm). The purification process was performed using a Waters Delta Prep 2000/4000 system coupled to a Waters 2489 UV-Vis detector. Details of the preparative method are summarized in Table 42.

TABLE 42

Conditions for Primary Preparative HPLC Method.

| Column | Waters Symmetry Shield RP18 (50 × 250 mm, 5 μm) |
|---|---|
| Flow Rate (mL/min) | 118.0 |
| Detection | UV at 210 nm |
| Mobile Phases | (A) 82:18 Water/MeCN |
|  | (B) MeCN |

TABLE 42-continued

Conditions for Primary Preparative HPLC Method.

| Sample Preparation | 52 mg dissolved in 20 mL of DI water |
|---|---|
| Gradient: | Isocratic 100% MP-A for 50 min |

Isolation Procedure. Fractions collected during the final pre-concentration step were concentrated in vacuo using a Buchi® Rotary Evaporator, Model R-114. The concentrated solution was dried for 48-72 h using the Kinetics Flexi-Dry Personal Freeze Dryer.

MS and MS/MS. MS and MS/MS data were generated with a Waters QTof Micro mass spectrometer equipped with an electrospray ionization source. The sample was analyzed by negative ESI. The sample (0.1 mg) was diluted with 50:50 $ACN:H_2O$ to a concentration of 0.1 mg/mL and introduced via direct infusion.

NMR. The sample was prepared by dissolving 3.3 mg in 130 μL of $CD_3OD$ and NMR data were acquired on a Bruker Avance 500 MHz instrument equipped with a 2.5 mm inverse probe and a 5 mm broad band probe. The $^1H$ NMR spectrum was referenced to the $CHD_2OD$ resonance at $\delta_H$ 3.30 ppm and $^{13}C$ NMR spectrum was referenced to the $CD_3OD$ resonance at $\delta_C$ 49.0 ppm.

Results and Discussion

Primary Purification. Approximately 52 mg of Lot #GM-3502-106-8 was processed using the primary preparative HPLC method described above. Fractions were analyzed using the analytical method summarized above. Collected fraction Lot #RAD-D-166(3) was determined to be sufficiently pure for NMR studies, retention time approximately 35 min on the respective preparative trace.

Final Batch Preparation. Fraction Lot #RAD-D-166(3) was concentrated by rotary evaporation and further dried via lyophilization for 48 hours. The final yield of the batch RAD-D-166(3) was 18.6 mg. The final purity was determined using the analytical method summarized above and found to be 94.4% (AUC, CAD) with a retention time of 28.401 min and >99.0% (AUC, UV) with a retention time of 28.307 min.

Mass Spectrometry. The ESI-TOF mass spectrum acquired by infusing a sample of CC-00417 showed a $[M-H]^-$ ion at m/z 1447.6820. The mass of the $[M-H]^-$ ion was in good agreement with the molecular formula $C_{66}H_{112}O_{34}$ (calcd for $C_{66}H_{111}O_{34}$: 1447.6957, error: −9.5 ppm) expected. The MS data confirmed that CC-00417 has a nominal mass of 1448 Daltons with the molecular formula, $C_{66}H_{112}O_{34}$. The ion observed at m/z 1545.6769 is most likely due to $[M-H+H_3PO_4]^-$.

The MS/MS spectrum of CC-00417, selecting the $[M-H]^-$ ion at m/z 1447.6 for fragmentation, indicated sequential loss of six glucose units at m/z 1285.5469, 1123.5262, 961.4609, 799.4135, 637.3846, and 475.3622 indicated presence of six glucose units in the structure. Following the loss of one sugar from the structure an alternative fragmentation pathway is also observed in the spectrum which would correspond to loss of water molecule from the central triterpene core followed by sequential loss of glucose units at m/z 1267.4888, 1105.5851, 943.4105, 781.4169, 619.3828, and 473.3254. The ion observed at m/z 383.0933 could be most likely due to the loss of six glucose and C-24 isopropyl hydroxyl units. NMR Spectroscopy. A series of NMR experiments including $^1H$ NMR, $^{13}C$ NMR, $^1H$-$^1H$ COSY, HSQC-DEPT, HMBC, ROESY, and 1D TOCSY were acquired to allow assignment of CC-00417.

The 1D and 2D NMR data indicated that the central core of the glycoside is a triterpene. A summary of the $^1$H and $^{13}$C chemical shifts for the aglycone are found in Table 43.

TABLE 43

$^1$H and $^{13}$C NMR (500 and 125 MHz, CD$_3$OD), assignments of the CC-00417 aglycone.

| Position | $^{13}$C | $^1$H |
|---|---|---|
| 1 | 27.2 | 1.48 m |
|  |  | 2.22 m |
| 2 | 29.7 | 1.89 m |
|  |  | 1.95 m |
| 3 | 88.2 | 3.46 m |
| 4 | 42.9 | — |
| 5 | 145.0 | — |
| 6 | 119.6 | 5.48 brd (5.5) |
| 7 | 25.1 | 1.80 m |
|  |  | 2.38 m |
| 8 | 44.6 | 1.66 m |
| 9 | 40.9 | — |
| 10 | 37.2 | 2.49 brd (11.9) |
| 11 | 79.4 | 3.84 m |
| 12 | 41.1 | 1.81 m |
|  |  | 1.86 m |
| 13 | 48.3 | — |
| 14 | 50.6 | — |
| 15 | 35.4 | 1.13 m |
|  |  | 1.20 m |
| 16 | 29.4 | 1.32 m |
|  |  | 1.98 m |
| 17 | 51.7 | 1.62 m |
| 18 | 17.1 | 0.91 s |
| 19 | 26.2 or 26.3 | 1.10 s |
| 20 | 37.5 | 1.44 m |
| 21 | 19.3 | 0.97 d (6.2) |
| 22 | 34.2 | 1.47 m |
|  |  | 1.56 m |
| 23 | 29.8 | 1.40 m |
|  |  | 1.55 m |
| 24 | 93.3 | 3.40 m |
| 25 | 73.9 | — |
| 26 | 26.8† | 1.11 s† |
| 27 | 24.3† | 1.14 s† |
| 28 | 28.0 | 1.07 s |
| 29 | 26.2 or 26.3 | 1.18 s |
| 30 | 20.0 | 0.88 s |

†Assignments can be interchanged.

A summary of the $^1$H and $^{13}$C chemical shifts for the glycoside at C-3 are found in Table 44.

TABLE 44

$^1$H and $^{13}$C NMR (500 and 125 MHz, CD$_3$OD), assignments of the CC-00417 C-3 glycoside.

| Position | $^{13}$C | $^1$H |
|---|---|---|
| Glc$_{IV}$-1 | 106.4 | 4.28 d (7.8) |
| Glc$_{IV}$-2 | 75.2-75.6¥ | 3.19 m |
| Glc$_{IV}$-3 | 77.7-78.2§ | 3.31 m |
| Glc$_{IV}$-4 | 71.5-71.9€ | 3.30 m |
| Glc$_{IV}$-5 | 77.2 | 3.41 m |
| Glc$_{IV}$-6 | 69.7 | 3.80 m, 4.05 m |
| Glc$_{V}$-1 | 104.8 | 4.42 d (7.8) |
| Glc$_{V}$-2 | 75.2-75.6¥ | 3.19 m |
| Glc$_{V}$-3 | 77.7-78.2§ | 3.36 m |
| Glc$_{V}$-4 | 71.5-71.9€ | 3.29 m |
| Glc$_{V}$-5 | 77.7-78.2§ | 3.25 m |
| Glc$_{V}$-6 | 62.7 | 3.66 m, 3.85 m |

¥Four carbon resonances in the range of 75.2-75.6 ppm (75.17, 75.20 and 75.56 ppm; one additional carbon overlap at 75.17/75.20 ppm), hence chemical shifts could not be unequivocally assigned.
§Six carbon resonances in the range of 77.7-78.2 ppm (77.67, 77.91, 77.97, 78.04, 78.12 and 78.18 ppm), hence chemical shifts could not be unequivocally assigned.
€Five carbon resonances in the range of 71.5-71.9 ppm (71.46, 71.56, 71.62, 71.70 and 71.94 ppm), hence chemical shifts could not be unequivocally assigned.

A summary of the $^1$H and $^{13}$C chemical shifts for the glycoside at C-24 are found in Table 45.

TABLE 45

$^1$H and $^{13}$C NMR (500 and 125 MHz, CD$_3$OD), assignments of the CC-00417 C-24 glycoside.

| Position | $^{13}$C | $^1$H |
|---|---|---|
| Glc$_I$-1 | 104.1 | 4.44 d (7.1) |
| Glc$_I$-2 | 81.2 | 3.61 m |
| Glc$_I$-3 | 78.7 | 3.59 m |
| Glc$_I$-4 | 71.5-71.9€ | 3.27 m |
| Glc$_I$-5 | 76.7 | 3.54 m |
| Glc$_I$-6 | 70.8 | 3.54 m, 4.26 m |
| Glc$_{II}$-1 | 104.9 | 4.32 d (7.7) |
| Glc$_{II}$-2 | 75.2† | 3.23 m |
| Glc$_{II}$-3 | 77.7-78.2§ | 3.37 m |
| Glc$_{II}$-4 | 71.5-71.9€ | 3.39 m |
| Glc$_{II}$-5 | 76.3 | 3.47 m |
| Glc$_{II}$-6 | 67.3 | 3.73 m, 3.94 m |
| Glc$_{III}$-1 | 104.5 | 4.78 d (7.8) |
| Glc$_{III}$-2 | 75.7 | 3.27 m |
| Glc$_{III}$-3 | 77.7-78.2§ | 3.36 m |
| Glc$_{III}$-4 | 72.3 | 3.21 m |
| Glc$_{III}$-5 | 77.7-78.2§ | 3.27 m |
| Glc$_{III}$-6 | 63.5 | 3.63 m, 3.86 m |
| Glc$_{VII}$-1 | 99.9 | 4.83 d (3.6†) |
| Glc$_{VII}$-2 | 73.8 | 3.36 m |
| Glc$_{VII}$-3 | 75.2† | 3.65 m |
| Glc$_{VII}$-4 | 71.5-71.9€ | 3.32 m |
| Glc$_{VII}$-5 | 73.5 | 3.66 m |
| Glc$_{VII}$-6 | 62.5 | 3.68 m, 3.78 m |

€Five carbon resonances in the range of 71.5-71.9 ppm (71.46, 71.56, 71.62, 71.70 and 71.94 ppm), hence chemical shifts could not be unequivocally assigned.
†Three carbon resonances at 75.2 ppm (75.17 and 75.20; one additional carbon overlap in this region), hence chemical shifts could not be unequivocally assigned. For Glc$_I$-2 and Glc$_I$-2 (Table 5), the range is 75.2-76.6 ppm.
§Six carbon resonances in the range of 77.7-78.2 ppm (77.67, 77.91, 77.97, 78.04, 78.12 and 78.18 ppm), hence chemical shifts could not be unequivocally assigned.
†Coupling constant based on $^1$H NMR data acquired at 296K.

The structure of CC-00417 was determined to be mogro-3-O-[β-D-glucopyranosyl (1→6)-β-D-glucopyranoside]-24-O-{[β-D-glucopyranosyl-(1→2)]-[α-D-glucopyranosyl-(1→6)-(β-D-glucopyranosyl-(1→6)]-β-D-glucopyranoside}. This compound contains one additional glucose unit (GlcVII) than Mogroside V, which is attached to GlcII via 1→6 α-linkage, thus bearing three 1→6 sugar linkages in the structure.

Example 7: Preparation, Purification and Characterization of CC-00434

A mixture of mogroside IIIE (500 mg) and soluble starch (2.5 g) in 50 mL of sodium acetate buffer (pH5) and enzyme (20 mL; CGT "Amano") was stirred at about 50° C. for 1 day. The reaction mixture was heated at 80° C. for 30 min and cooled to room temperature. The solid was filtered and the filtrate was freeze dried to give a crude product (Lot #GM-3502-156), which was purified using Prep-HPLC.

HPLC Analysis. HPLC analyses were performed on a Waters 2695 Alliance System coupled to a Waters 996 Photo Diode Array (PDA) detector. In addition, sample purities were assessed using an ESA Corona Plus Charged Aerosol Detector (CAD). Sample analyses were performed using the method conditions described in Tables 46 and 47.

TABLE 46

Analytical HPLC Conditions for Fraction Analysis in Primary and Secondary Process

| Parameter | Description |
| --- | --- |
| Column (Dimensions) | Phenomenex Synergi Hydro RP (4.6 × 250 mm, 4 µm) |
| Column Temperature (° C.) | Ambient |
| Sample Temperature (° C.) | Ambient |
| Mobile Phases | (A) Water |
|  | (B) Acetonitrile (MeCN) |
| Flow Rate (mL/min) | 1.0 |
| Detection | UV at 210 nm and CAD |

| Gradient | | |
| --- | --- | --- |
| Time (min) | % A | % B |
| 0.0-40.0 | 77 | 23 |
| 40.01-47.0 | 10 | 90 |
| 47.01-57.0 | 77 | 23 |

TABLE 47

Analytical HPLC Conditions for Final Purity Analysis

| Parameter | Description |
| --- | --- |
| Column (Dimensions) | Phenomenex Synergi Hydro RP (4.6 × 250 mm, 4 µm) |
| Column Temperature (° C.) | 55 |
| Sample Temperature (° C.) | Ambient |
| Mobile Phases | (A) 0.0284% Ammonium Acetate ($NH_4OAc$) and 0.0116% Acetic Acid (HOAc) in Water |
|  | (B) MeCN |
| Flow Rate (mL/min) | 1.0 |
| Detection | UV at 210 nm and CAD |

| Gradient | | |
| --- | --- | --- |
| Time (min) | % A | % B |
| 0.0 | 85 | 15 |
| 28.5 | 75 | 25 |
| 30.0 | 71 | 29 |
| 36.5 | 70 | 30 |
| 38.5-44.5 | 66 | 34 |
| 46.5-49.0 | 48 | 52 |
| 51.0-57.0 | 30 | 70 |
| 58.0 | 85 | 15 |

Primary Preparative HPLC Method. The primary processing of Lot #GM-3502-156 was performed using a Phenomenex Synergi Hydro RP column (50×250 mm, 10 µm). The purification process was performed using a Waters Delta Prep 2000/4000 system coupled to a Waters 2487 UV-Vis detector. Details of the preparative methods are summarized in Table 48.

TABLE 48

Conditions for Primary Preparative HPLC Method.

| Parameter | Description |
| --- | --- |
| Column (Dimensions) | Phenomenex Synergi Hydro RP (50 × 250 mm, 10 µm) |
| Flow Rate (mL/min) | 118.0 |
| Detection | UV at 210 nm |
| Mobile Phases | (A) 77:23 Water/MeCN |
|  | (B) 10:90 Water/MeCN |

TABLE 48-continued

Conditions for Primary Preparative HPLC Method.

| Parameter | Description |
| --- | --- |
| Sample Preparation | 3 g dissolved in 20 mL Water |
| Gradient | Isocratic hold of 100% MP-A for 25 min, then 7 min flush of 100% MP-B |

Secondary Preparative HPLC Method. The secondary processing was performed using a Phenomenex Synergi Hydro RP (50×250 mm, 10 µm). The purification process was performed with a Waters Delta Prep LC Model 2000/4000 system coupled to a Waters 2487 UV-Vis detector. Details of the preparative method are summarized in Table 49.

TABLE 49

Conditions for Secondary Preparative HPLC Method.

| Parameter | Description |
| --- | --- |
| Column (Dimensions) | Phenomenex Synergi Hydro RP (50 × 250 mm, 10 µm) |
| Flow Rate (mL/min) | 118.0 |
| Detection | UV at 210 nm |
| Mobile Phases | (A) 77:23 Water/MeCN |
|  | (B) 10:90 Water/MeCN |
| Sample Preparation | Sample dissolved in 20 ml of Water |
| Gradient: | Isocratic hold of 100% MP-A for 30 min, then 7 min flush of 100% MP-B |

Isolation Procedure. Fractions collected during the final pre-concentration step were concentrated in vacuo using a Buchi® Rotary Evaporator, Model R-114. The concentrated solution was dried for 48 h using the LabConco Freezone Personal Freeze Dryer.

MS and MS/MS. MS and MS/MS data were generated with a Waters QTof Micro mass spectrometer equipped with an electrospray ionization source. The sample was analyzed by negative ESI. The sample (~0.2 mg) was diluted with 50:50 ACN:$H_2O$ to a concentration of ~0.2 mg/mL and introduced via direct infusion.

NMR. The sample was prepared by dissolving 2.7 mg in 130 µL of $CD_3OD$ and NMR data were acquired on a Bruker Avance 500 MHz NMR spectrometer equipped with a 2.5 mm inverse probe and a 5 mm broad band probe. The $^1H$ NMR spectrum was referenced to the $CHD_2OD$ resonance at $\delta_H$ 3.30 ppm and $^{13}C$ NMR spectrum was referenced to the $CD_3OD$ resonance at $\delta_C$ 49.0 ppm.

Results and Discussion

Primary Purification. Approximately 3 g of Lot #GM-3502-156 was processed using the primary preparative HPLC method described above. Fractions were analyzed using the analytical method summarized above. Collected fraction Lot #RAD-D-199(1), Lot #RAD-D-199(2), Lot #RAD-D-199(3), Lot #RAD-D-199(4) and Lot #RAD-D-199(5) having retention range from 8-13 minutes were pooled and relabeled Lot #RAD-D-199(1-5) for reprocessing.

Secondary Purification. Fraction Lot #RAD-D-199(1-5) was reprocessed using the conditions described above. Fractions were analyzed using the analytical method summarized above. Collected fraction Lot #RAD-D-201(5) had a retention time of approximately 16.5 min in the preparative HPLC trace. This fraction was deemed sufficiently pure for structural elucidation via NMR.

Final Batch Preparation. Fraction Lot #RAD-D-201(5) was concentrated by rotary evaporation and further dried via lyophilization for 48 hours. The final yield of batch RAD-D-201(5) was 26.3 mg. The final purity was determined using the analytical method summarized above and was found to be 92.2% (AUC, CAD) with a retention time of 32.2 min. The sample was also analyzed by UV/Vis and purity was determined to be 21.2% (AUC, UV) with a retention time of 32.2 min.

Mass Spectrometry. The ESI-TOF mass spectrum acquired by infusing a sample of CC-00434 showed a [M–H]$^-$ ion at m/z 1285.6427. The mass of the [M–H]$^-$ ion was in good agreement with the molecular formula $C_{60}H_{102}O_{29}$ (calcd for $C_{60}H_{101}O_{29}$: 1285.6429, error: –0.2 ppm) expected.

The MS data confirmed that CC-00434 had a nominal mass of 1286 Daltons with the molecular formula, $C_{60}H_{102}O_{29}$. The ion observed at m/z 1399.6442 was most likely due to [M–H+CF$_3$COOH]$^-$.

The MS/MS spectrum of CC-00434, selecting the [M–H]$^-$ ion at m/z 1285.6 for fragmentation, indicated sequential loss of five glucose units at m/z 1123.5201, 961.5393, 799.4852, 637.4305, and 475.3716 and thus indicated presence of five glucose units in the structure. Following the loss of one sugar from the structure another fragmentation pathway was also observed in the spectrum which corresponded to loss of water molecule from the central triterpene core to give m/z 1105.6173 followed by sequential loss of three glucose units at m/z 943.5240, 781.4962 and 619.4466. The ion observed at m/z 383.1145 was likely due to the loss of five glucose and C-24 isopropyl hydroxyl units.

NMR Spectroscopy. A series of NMR experiments including $^1$H NMR, $^{13}$C NMR, $^1$H-$^1$H COSY, HSQC-DEPT, HMBC, ROESY, and 1D TOCSY were acquired to allow assignment of CC-00434.

The 1D and 2D NMR data indicated that the central core of the glycoside is a triterpene. A summary of the $^1$H and $^{13}$C chemical shifts for the aglycone are found in Table 50.

TABLE 50

$^1$H and $^{13}$C NMR (500 and 125 MHz, CD$_3$OD), assignments of the CC-00434 aglycone.

| Position | $^{13}$C | $^1$H |
|---|---|---|
| 1 | 27.2 | 1.50 m |
|  |  | 2.21 m |
| 2 | 29.6 | 1.93 m |
|  |  | 1.95 m |
| 3 | 88.6 | 3.42 m |
| 4 | 42.9 | — |
| 5 | 145.0 | — |
| 6 | 119.6 | 5.48 brd (5.8) |
| 7 | 25.1 | 1.81 m |
|  |  | 2.38 m |
| 8 | 44.7 | 1.67 m |
| 9 | 40.9 | — |
| 10 | 37.2 | 2.50 brd (11.9) |
| 11 | 79.4 | 3.84 m |
| 12 | 41.3 | 1.81 m |
|  |  | 1.92 m |
| 13 | 48.3 | — |
| 14 | 50.6 | — |
| 15 | 35.4 | 1.14 m |
|  |  | 1.21 m |
| 16 | 29.4 | 1.32 m |
|  |  | 1.99 m |
| 17 | 51.9 | 1.64 m |
| 18 | 17.1 | 0.91 s |
| 19 | 26.2 or 26.3 | 1.10 s |
| 20 | 38.0 | 1.43 m |
| 21 | 19.2 | 0.98 d (6.3) |
| 22 | 34.4 | 1.46 m |
|  |  | 1.55 m |
| 23 | 30.0 | 1.41 m |
|  |  | 1.64 m |
| 24 | 91.0 | 3.45 m |
| 25 | 73.8 | — |
| 26 | 26.6† | 1.13 s† |
| 27 | 24.5† | 1.17 s† |
| 28 | 28.1 | 1.08 s |
| 29 | 26.2 or 26.3 | 1.18 s |
| 30 | 20.1 | 0.90 s |

†Assignments can be interchanged.

A summary of the $^1$H and $^{13}$C chemical shifts for the glycoside at C-3 are found in Table 51.

TABLE 51

$^1$H and $^{13}$C NMR (500 and 125 MHz, CD$_3$OD), assignments of the CC-00434 C-3 glycoside.

| Position | $^{13}$C | $^1$H |
|---|---|---|
| Glc$_{IV}$-1 | 106.5 | 4.27 d (7.8) |
| Glc$_{IV}$-2 | 75.6 | 3.18 m |
| Glc$_{IV}$-3 | 78.2 | 3.32 m |
| Glc$_{IV}$-4 | 71.4-71.7$^\varepsilon$ | 3.28 m |
| Glc$_{IV}$-5 | 77.6 | 3.21 m |
| Glc$_{IV}$-6 | 62.8-62.9† | 3.65 m, 3.81 m |

$^\varepsilon$Three carbon resonances in the range of 71.4-71.7 ppm (71.44, 71.56 and 71.71 ppm), hence chemical shifts could not be unequivocally assigned.
†Three carbon resonances in the range of 62.8-62.9 ppm (62.77, 62.86 and 62.92 ppm), hence chemical shifts could not be unequivocally assigned.

A summary of the $^1$H and $^{13}$C chemical shifts for the glycoside at C-24 are found in Table 52.

TABLE 52

$^1$H and $^{13}$C NMR (500 and 125 MHz, CD$_3$OD), assignments of the CC-00434 C-24 glycoside.

| Position | $^{13}$C | $^1$H |
|---|---|---|
| Glc$_I$-1 | 103.4 | 4.46 d (7.4) |
| Glc$_I$-2 | 81.6 | 3.56 m |
| Glc$_I$-3 | 78.6 | 3.56 m |
| Glc$_I$-4 | 71.4-71.7$^\varepsilon$ | 3.29 m |
| Glc$_I$-5 | 78.1 | 3.28 m |
| Glc$_I$-6 | 62.6 | 3.62 m, 3.86 m |
| Glc$_{III}$-1 | 104.6 | 4.76 d (7.8) |
| Glc$_{III}$-2 | 75.5 | 3.30 m |
| Glc$_{III}$-3 | 77.9 | 3.63 m |
| Glc$_{III}$-4 | 80.9 | 3.45 m |
| Glc$_{III}$-5 | 77.0 | 3.38 m |
| Glc$_{III}$-6 | 62.8-62.9† | 3.72 m, 3.88 m |
| Glc$_{VII}$-1 | 102.3 | 5.21 d (3.8) |
| Glc$_{VII}$-2 | 73.6 | 3.47 m |
| Glc$_{VII}$-3 | 74.9 | 3.84 m |
| Glc$_{VII}$-4 | 81.2 | 3.51 m |
| Glc$_{VII}$-5 | 73.3 | 3.73 m |
| Glc$_{VII}$-6 | 61.8 | 3.82 m, 3.84 m |
| Glc$_{VIII}$-1 | 102.9 | 5.15 d (3.8) |
| Glc$_{VIII}$-2 | 74.3 | 3.44 m |
| Glc$_{VIII}$-3 | 75.1 | 3.61 m |
| Glc$_{VIII}$-4 | 71.4-71.7$^\varepsilon$ | 3.26 m |

TABLE 52-continued $^1$H and $^{13}$C NMR (500 and 125 MHz, CD$_3$OD), assignments of the CC-00434 C-24 glycoside.

| Position | $^{13}$C | $^1$H |
|---|---|---|
| Glc$_{VIII}$5 | 74.8 | 3.68 m |
| Glc$_{VIII}$6 | 62.8-62.9$^\dagger$ | 3.65 m, 3.82 m |

$^\epsilon$Three carbon resonances in the range of 71.4-71.7 ppm (71.44, 71.56 and 71.71 ppm), hence chemical shifts could not be unequivocally assigned.
$^\dagger$Three carbon resonances in the range of 62.8-62.9 ppm (62.77, 62.86 and 62.92 ppm), hence chemical shifts could not be unequivocally assigned.

The structure of CC-00434 was determined to be mogrol-3-O-[β-D-glucopyranoside]-24-O-{[(α-D-glucopyranosyl-(1→4))-(α-D-glucopyranosyl-(1→4))-β-D-glucopyranosyl-(1→2)]-β-D-glucopyranoside}. This compound is related to Mogroside IIIE but differs from it by two additional glucose units (GlcVII and GlcVIII) attached to GlcIII via 1→4 sugar linkage.

Example 8: Preparation, Purification and Characterization of CC-00478

CC-00478 and CC-00485 were isolated from a mixture of mogrosides from bioconversion of Mogroside IIIE.

All the materials for the medium were purchased from Fisher Scientific; Gene and vector were synthesized and supplied by Gene Universal Inc.; Tuner™ DE3 competent cell-Novagen was purchased from Millipore Sigma; Dextranase was purchased from Sigma-Aldrich.

Construction of Expression Strain for Dextran Sucrase

Gene dexYG (GenBank: DQ345760.1) was cloned into the vector pET-28a(+) with cloning site BamHI and HindIII. The plasmid pET-28a(+)-dexYG was then transformed into Tuner™ DE3 competent cell to obtain recombinant E. coli BL21 Tuner DE3/pETdex.

Cells of E. coli BL21 Tuner DE3/pETdex were incubated in 10 ml LB medium with resistance 50 ug/ml Kanamycin, 37° C., 220 rpm, overnight. Then the culture was transferred into 1 L fermentation medium$^1$ and Kanamycin (1 ml, 100 mg/ml), 37° C., 300 rpm, 23 hs; 1M IPGT 1 ml was added at 24° C., with supplementary medium 20 mL/h, O$_2$ 10 L/min, 24° C., 300 rpm, 25 hs. During the fermentation, the pH was maintained at 7.0. The cells were harvested at 5000 rpm, 4° C., 20 mins.

$^1$Fermentation medium: Tryptone (10 g), CaCl2)(0.5M, 0.5 mL), KH2PO4 (3 g), MgSO4·7H2O (0.3M, 13 mL), Glucose (20 g)
$^2$Supplementary medium: Glucose (100 g), KH$_2$PO$_4$ (0.75 g), (NH$_4$)$_2$HPO$_4$ (5 g), NaH$_2$PO$_4$ (2 g), (NH$_4$)$_2$SO$_4$ (2.5 g), Lactose (10 g), MgSO$_4$·7H$_2$O (0.3 M, 30 mL), CaCl$_2$) (0.55 M 12.5 mL)

The cells were re-suspended in 320 ml 50 mM pH5.5 sodium acetate buffer, separated into 8 tubes, 40 mL each tube. It cells were then sonicated on ice for 3 secs on/3 secs off for 30 mins. The lysate was centrifuged at 13000 rpm, 4° C. for 40 mins. The supernatant was used for the enzyme reaction.

Dextran Sucrase Reaction:

Sucrose 8 g, Mog IIIE 2 g, 0.1 M CaCl$_2$) 2 ml, acetate buffer pH 5.5 50 mL, 2 tubes (40 mL*2) supernatants from above, 30° C., 180 rpm, 2 days. The reaction was monitored by TLC. Dextranase was added when sucrose was no longer detected.

Dextranase Reaction:

Added 2.5 ml dextranase (purchased from Sigma Aldrich) for each 2 g Mog IIIE, 30° C., 180 rpm, 2 days. The reaction was monitored by TLC and MALDI-TOF. After the reaction was complete, the reaction mixture was boiled for 10 mins and centrifuged 12000 rpm, 40 mins. The supernatant was collected and evaporated and purified by silica gel chromatography (3 EtOAc/1 MeOH).

HPLC Analysis. HPLC analyses were performed on a Waters 2695 Alliance System coupled to a Waters 996 Photo Diode Array (PDA) detector. In addition, sample purities were assessed using an ESA Corona plus Charged Aerosol Detector (CAD). Sample analysis was performed using the method conditions described in Table 53.

TABLE 53

Analytical HPLC Conditions for all Fraction analysis and Final purity analysis.

| Parameter | Description |
|---|---|
| Column (Dimensions) | Phenomenex Synergi Hydro RP-80A (250 × 4.60 mm, 4 µm) |
| Column Temperature (° C.) | Ambient |
| Sample Temperature (° C.) | Ambient |
| Mobile Phases | (A) Water |
| | (B) Acetonitrile (MeCN) |
| Flow Rate (mL/min) | 1.0 |
| Detection | UV at 210 nm and CAD |

| Gradient | | |
|---|---|---|
| Time (min) | % A | % B |
| 0.0-50.0 | 80 | 20 |
| 50.50-57.0 | 10 | 90 |
| 57.50-67.0 | 80 | 20 |

Primary Preparative HPLC Method. The primary processing of Lot #20180501 (1.5 g) was performed using a Phenomenex Synergi Hydro RP-80A column (50×250 mm, 10 µm). The purification process was performed using a Waters Delta Prep 2000/4000 system coupled to a Waters 2487 UV-Vis detector. Details of the preparative methods are summarized in Table 54. The fraction of interest was KTC-D-68(16), with a retention time of 42-47 minutes. Fractions were analyzed using the analytical method above.

TABLE 54

Conditions for Primary Preparative HPLC Method.

| Parameter | Description |
|---|---|
| Column (Dimensions) | Phenomenex Synergi Hydro RP-80A (250 × 50 mm, 10 µm) |
| Flow Rate (mL/min) | 118.0 |
| Detection | UV at 210 nm |
| Mobile Phases | (A) 80:20 Water/MeCN |
| | (B) 10:90 Water/MeCN |
| Gradient | Isocratic hold of 100% MP-A for 60 min, then 10 min flush of 100% MP-B |

Secondary Preparative HPLC Method. The secondary processing of pooled fraction KTC-D-68(16) was performed using a Phenomenex Synergi Hydro RP-80A column (50× 250 mm, 10 µm). The purification process was performed using a Waters 2545 Quaternary Gradient Module system coupled to a Waters 2489 UV-Vis detector. Details of the preparative method are summarized in Table 55. The fraction of interest, KTC-D-76(7), had a retention time of 45-50 minutes. Fractions were analyzed using the analytical method above. Collected fraction KTC-D-76(7), retention time approximately 49 min shown on HPLC trace was deemed sufficiently pure for structural elucidation via NMR.

TABLE 55

Conditions for Secondary Preparative HPLC Method.

| Parameter | Description |
|---|---|
| Column (Dimensions) | Phenomenex Synergi Hydro RP-80A (250 × 50 mm, 10 μm) |
| Flow Rate (mL/min) | 118.0 |
| Detection | UV at 210 nm |
| Mobile Phases | (A) 80:20 Water/MeCN |
|  | (B) 10:90 Water/MeCN |
| Gradient: | Isocratic hold of 100% MP-A for 55 min, then 10 min flush of 100% MP-B |

Final Batch Preparation. Fraction Lot #KTC-D-76(7) was concentrated by rotary evaporation and further dried via lyophilization for 24 hours. The final yield of the batch KTC-D-76(7) was 41.9 mg. The final purity was determined using the analytical method summarized above and found to be 92.0% (AUC, CAD) with a retention time of 49.5 min.

Mass Spectrometry. The ESI-TOF mass spectrum acquired by infusing a sample of CC-00478 showed a [M−H]⁻ ion at m/z 1123.5554. The mass of the [M−H]⁻ ion was in good agreement with the molecular formula $C_{54}H_{92}O_{24}$ (calcd for $C_{54}H_{91}O_{24}$: 1123.5900, error: −1.2 ppm) expected. The MS data confirmed that CC-00478 had a nominal mass of 1124 Daltons with the molecular formula, $C_{54}H_{92}O_{24}$. The ions observed at m/z 1169.5630 and 1237.5564 was likely due to [M−H+HCOOH]⁻ and [M−H+TFA]⁻, respectively.

The MS/MS spectrum of CC-00478, selecting the [M−H]⁻ ion at m/z 1123.0 for fragmentation, indicated sequential loss of four glucose units at m/z 961.5377, 799.4740, 637.4214, and 475.3722 indicated presence of four glucose units in the structure. The ion observed at m/z 383.1174 was most likely due to the loss of four glucose and C-24 isopropyl hydroxyl units.

NMR Spectroscopy. A series of NMR experiments including ¹H NMR, ¹³C NMR, ¹H-¹H COSY, HSQC-DEPT, HMBC, ROESY, and 1D TOCSY were acquired to allow assignment of CC-00478.

The 1D and 2D NMR data indicated that the central core of the glycoside is a triterpene. A summary of the ¹H and ¹³C chemical shifts for the aglycone are found in Table 56.

TABLE 56

¹H and ¹³C NMR (500 and 125 MHz, CD₃OD), assignments of the CC-00478 aglycone.

| Position | ¹³C | ¹H |
|---|---|---|
| 1 | 27.2 | 1.50 m |
|  |  | 2.21 m |
| 2 | 29.6 | 1.92 m |
|  |  | 1.95 m |
| 3 | 88.5 | 3.41 m |
| 4 | 42.9 | — |
| 5 | 145.0 | — |
| 6 | 119.6 | 5.48 brd (5.8) |
| 7 | 25.1 | 1.80 m |
|  |  | 2.38 brd (18.4, 7.2) |
| 8 | 44.7 | 1.66 m |
| 9 | 40.9 | — |
| 10 | 37.3 | 2.48 brd (12.2) |
| 11 | 79.4 | 3.84 m |
| 12 | 41.0 | 1.81 m |
|  |  | 1.86 m |
| 13 | 48.3 | — |
| 14 | 50.6 | — |
| 15 | 35.3 | 1.13 m |
|  |  | 1.21 m |
| 16 | 29.3 | 1.32 m |
|  |  | 1.99 m |
| 17 | 51.7 | 1.62 m |
| 18 | 17.2 | 0.91 s |
| 19 | 26.2 | 1.10 s |
| 20 | 37.5 | 1.45 m |
| 21 | 19.3 | 0.98 d (6.1) |
| 22 | 34.6 | 1.39 m |
|  |  | 1.54 m |
| 23 | 29.2 | 1.50 m |
|  |  | 1.64 m |
| 24 | 88.1 | 3.50 m |
| 25 | 73.8¥ | — |
| 26 | 26.6† | 1.15 s† |
| 27 | 24.9† | 1.18 s† |
| 28 | 27.9 | 1.07 s |
| 29 | 26.3 | 1.18 s |
| 30 | 19.9 | 0.87 s |

†Assignments can be interchanged.
¥Three carbon resonances at 73.8 ppm (73.75 and 73.82 ppm; two carbon resonances overlap at 73.82 ppm), hence chemical shifts could not be unequivocally assigned.

A summary of the ¹H and ¹³C chemical shifts for the glycoside at C-3 are found in Table 57.

TABLE 57

¹H and ¹³C NMR (500 and 125 MHz, CD₃OD), assignments of the CC-00478 C-3 glycoside.

| Position | ¹³C | ¹H |
|---|---|---|
| Glc$_{IV}$-1 | 106.5 | 4.27 d (7.8) |
| Glc$_{IV}$-2 | 75.6 | 3.18 m |
| Glc$_{IV}$-3 | 78.2 | 3.31 m |
| Glc$_{IV}$-4 | 71.7-71.8§ | 3.28 m |
| Glc$_{IV}$-5 | 77.6 | 3.20 m |
| Glc$_{IV}$-6 | 62.5-62.9€ | 3.65 m, 3.81 m |

§Three carbon resonances at 71.7-71.8 ppm (71.70 and 71.77 ppm; two carbons overlap at 71.77 ppm), hence chemical shifts could not be unequivocally assigned.
€Three carbon resonances at 62.5-62.9 ppm (62.54, 62.63 and 62.85 ppm), hence chemical shifts could not be unequivocally assigned.

A summary of the ¹H and ¹³C chemical shifts for the glycoside at C-24 are found in Table 58.

TABLE 58

¹H and ¹³C NMR (500 and 125 MHZ, CD₃OD), assignments of the CC-00478 C-24 glycoside.

| Position | ¹³C | ¹H |
|---|---|---|
| Glc$_I$-1 | 102.1 | 4.49 d (7.3) |
| Glc$_I$-2 | 82.2 | 3.58 m |
| Glc$_I$-3 | 78.1 | 3.54 m |
| Glc$_I$-4 | 71.5 | 3.33 m |
| Glc$_I$-5 | 78.0 | 3.25 m |
| Glc$_I$-6 | 62.5-62.9€ | 3.64 m, 3.85 m |
| Glc$_{III}$-1 | 105.0 | 4.64 d (7.7) |
| Glc$_{III}$-2 | 75.5 | 3.31 m |
| Glc$_{III}$-3 | 77.9 | 3.37 m |
| Glc$_{III}$-4 | 71.7-71.8§ | 3.39 m |
| Glc$_{III}$-5 | 76.9 | 3.46 m |
| Glc$_{III}$-6 | 68.3 | 3.75 m, 3.94 dd (11.1, 4.3) |
| Glc$_{VI}$-1 | 100.2 | 4.88 d (3.7) |
| Glc$_{VI}$-2 | 73.8¥ | 3.35 m |
| Glc$_{VI}$-3 | 75.3 | 3.64 m |
| Glc$_{VI}$-4 | 71.7-71.8§ | 3.29 m |

TABLE 58-continued $^1$H and $^{13}$C NMR (500 and 125 MHZ, CD$_3$OD), assignments of the CC-00478 C-24 glycoside.

| Position | $^{13}$C | $^1$H |
|---|---|---|
| Glc$_{VI}$-5 | 73.8$^¥$ | 3.64 m |
| Glc$_{VI}$-6 | 62.5-62.9$^€$ | 3.68 m, 3.80 m |

$^€$Three carbon resonances at 62.5-62.9 ppm (62.54, 62.63 and 62.85 ppm), hence chemical shifts could not be unequivocally assigned.

$^§$Three carbon resonances at 71.7-71.8 ppm (71.70 and 71.77 ppm; two carbons overlap at 71.77 ppm), hence chemical shifts could not be unequivocally assigned.

$^¥$Three carbon resonances at 73.8 ppm (73.75 and 73.82 ppm; two carbon resonances overlap at 73.82 ppm), hence chemical shifts could not be unequivocally assigned.

The structure of CC-00478 was determined to be mogro-3-O-[β-D-glucopyranoside]-24-O-{[α-D-glucopyranosyl-(1→6)-β-D-glucopyranosyl-(1→2)]-β-D-glucopyranoside}.

Example 9: Preparation, Purification and Characterization of CC-00485

CC-0485 was isolated from a mixture of mogrosides from bioconversion of Mogroside IIIE as described in Example 8.

HPLC Analysis. HPLC analyses were performed on a Waters 2695 Alliance System coupled to a Waters 996 Photo Diode Array (PDA) detector. In addition, sample purities were assessed using an ESA Corona plus Charged Aerosol Detector (CAD). Sample analysis was performed using the method conditions described in Table 59.

TABLE 59

Analytical HPLC Conditions for all Fraction analysis and Final purity analysis.

| Parameter | Description |
|---|---|
| Column (Dimensions) | Phenomenex Synergi Hydro RP-80A (250 × 4.60 mm, 4 μm) |
| Column Temperature (° C.) | Ambient |
| Sample Temperature (° C.) | Ambient |
| Mobile Phases | (A) Water |
|  | (B) Acetonitrile (MeCN) |
| Flow Rate (mL/min) | 1.0 |
| Detection | UV at 210 nm and CAD |
| Diluent/Injection Vol. | Water/10 μL |

| Time (min) | % A | % B |
|---|---|---|
| 0.0-20.0 | 78 | 22 |
| 20.1-30.0 | 10 | 90 |
| 30.1-37.0 | 78 | 22 |

Primary Preparative HPLC Method. The primary processing of Lot #GM-3604-046-3 (8.5 g) was performed using a Phenomenex Synergi Hydro RP-80A column (50×250 mm, 10 μm). The purification process was performed using a Waters Delta Prep 2000/4000 system coupled to a Waters 2487 UV-Vis detector. Details of the preparative methods are summarized in Table 60. Fractions with retention time of 11-19 minutes were pooled into a single fraction labelled KTC-D-123. CC-00485 had a retention time of 19 minutes in the analytical HPLC method.

TABLE 60

Conditions for Primary Preparative HPLC Method.

| Parameter | Description |
|---|---|
| Column (Dimensions) | Phenomenex Synergi Hydro RP-80A (250 × 50 mm, 10 μm) |
| Flow Rate (mL/min) | 118.0 |
| Detection | UV at 210 nm |
| Mobile Phases | (A) 78:22 Water/MeCN |
|  | (B) 10:90 Water/MeCN |
| Sample Load | 8.5 g of Lot # GM-3604-046-3 was dissolved in 150 mL of water and injected |
| Gradient | Isocratic hold of 100% A for 25 min, then 15 min flush of 100% B |

Secondary Preparative HPLC Method. The secondary processing of combined fraction KTC-D-123 was performed using a Phenomenex Synergi Hydro RP-80A column (50× 250 mm, 10 μm). The purification process was performed using a Waters 2545 Quaternary Gradient Module system coupled to a Waters 2489 UV-Vis detector. Details of the preparative method are summarized in Table 61. Fractions having a retention time of 25-28 minutes were pooled and renamed KTC-D-124(5).

TABLE 61

Conditions for Secondary Preparative HPLC Method.

| Parameter | Description |
|---|---|
| Column (Dimensions) | Phenomenex Synergi Hydro RP-80A (250 × 50 mm, 10 μm) |
| Flow Rate (mL/min) | 118.0 |
| Detection | UV at 210 nm |
| Mobile Phases | (A) 78:22 Water/MeCN |
|  | (B) 10:90 Water/MeCN |
| Sample Load | ~20 mL of sample was diluted up to 100 mL with water and injected |
| Gradient: | Isocratic hold of 100% A for 27 min, then 10 min flush of 100% B |

Isolation Procedure. Lot KTC-D-124(5) was concentrated by rotary evaporation and further dried via lyophilization for 24 h. The final yield of the batch was 240 mg. Purity was determined to be 91.1% (AUC, CAD).

MS and MS/MS. MS and MS/MS data were generated with a Waters QTof Premium mass spectrometer equipped with an electrospray ionization source. The sample was analyzed by negative ESI. The sample (~0.2 mg) was diluted with 50:50 ACN:H$_2$O to a concentration of ~0.2 mg/mL and introduced via direct infusion.

The ESI-TOF mass spectrum acquired by infusing a sample of CC-00485 showed a [M−H]$^−$ ion at m/z 1123.5056. The mass of the [M−H]$^−$ ion was in good agreement with the molecular formula $C_{54}H_{92}O_{24}$ (calcd for $C_{54}H_{91}O_{24}$: 1123.5900, error: −5.0 ppm) expected. The MS data confirmed a nominal mass of 1124 Daltons with the molecular formula, $C_{54}H_{92}O_{24}$. The ion observed at m/z 1237.5260 was likely due to [M−H+TFA]$^−$.

The MS/MS spectrum of CC-00485, selecting the [M−H]$^−$ ion at m/z 1123.6 for fragmentation, indicated sequential loss of four glucose units at m/z 961.5027, 799.4667, 637.4043 and 475.3762 indicated presence of four glucose units in the structure. Following the loss of one sugar from the structure another fragmentation pathway was also observed in the spectrum which corresponded to loss of water molecule from the central triterpene core to give m/z 943.4355 followed by sequential loss of three glucose units at m/z 781.4574, 619.3746 and 457.3538.

NMR. The sample was prepared by dissolving 3.0 mg in 150 μL of CD$_3$OD and NMR data were acquired on a Bruker Avance 500 MHz instrument equipped with a 2.5 mm inverse probe and a 5 mm broad band probe. The $^1$H NMR spectrum was referenced to the CHD$_2$OD resonance at $\delta_H$ 3.30 and $^{13}$C NMR spectrum was referenced to the CD$_3$OD resonance at $\delta_C$ 49.0.

A series of NMR experiments including $^1$H NMR, $^{13}$C NMR, $^1$H–$^1$H COSY, HSQC-DEPT, HMBC, ROESY, and 1D TOCSY were acquired to allow assignment of CC-00485.

The 1D and 2D NMR data indicated that the central core of the glycoside is a triterpene. A summary of the $^1$H and $^{13}$C chemical shifts for the aglycone are found in Table 62.

TABLE 62

$^1$H and $^{13}$C NMR (500 and 125 MHz, CD$_3$OD), assignments of the CC-00485 aglycone.

| Position | $^{13}$C | $^1$H |
|---|---|---|
| 1 | 27.2 | 1.51 m |
|   |      | 2.19 m |
| 2 | 29.3$^\epsilon$ | 1.88 m |
|   |      | 1.92 m |
| 3 | 88.9 | 3.42 m |
| 4 | 42.8 | — |
| 5 | 144.8$^\S$ | — |
| 6 | 119.5 | 5.48 brd (5.9) |
| 7 | 25.1 | 1.81 m |
|   |      | 2.38 m |
| 8 | 44.6 | 1.66 m |
| 9 | 40.9 |  |
| 10 | 37.2 | 2.48 brd (11.8) |
| 11 | 79.4 | 3.84 m |
| 12 | 40.9 | 1.80 m |
|   |      | 1.85 m |
| 13 | 48.2 | — |
| 14 | 50.6 | — |
| 15 | 35.3 | 1.13 m |
|   |      | 1.20 m |
| 16 | 29.3$^\epsilon$ | 1.31 m |
|   |      | 1.97 m |
| 17 | 51.6 | 1.61 m |
| 18 | 17.1 | 0.91 s |
| 19 | 26.2 or 26.3 | 1.10 s |
| 20 | 37.5 | 1.46 m |
| 21 | 19.3 | 0.97 brd (5.3) |
| 22 | 34.4 | 1.47 m |
|   |      | 1.51 m |
| 23 | 29.3$^\epsilon$ | 1.46 m |
|   |      | 1.62 m |
| 24 | 89.5 | 3.47 m |
| 25 | 73.7 or 73.8 | — |
| 26 | 26.6$^\dagger$ | 1.14 s$^\dagger$ |
| 27 | 24.7$^\dagger$ | 1.17 s$^\dagger$ |
| 28 | 27.9 | 1.07 s |
| 29 | 26.2 or 26.3 | 1.19 s |
| 30 | 19.9 | 0.87 s |

$^\dagger$Assignments can be interchanged.
$^\epsilon$Three carbon resonances at 29.3 ppm (29.27 and 29.32 ppm; two carbon resonances overlap at 29.27 ppm), hence chemical shifts could not be unequivocally assigned.

A summary of the $^1$H and $^{13}$C chemical shifts for the glycoside at C-3 are found in Table 63.

TABLE 63

$^1$H and $^{13}$C NMR (500 and 125 MHz, CD$_3$OD), assignments of the CC-00485 C-3 glycoside.

| Position | $^{13}$C | $^1$H |
|---|---|---|
| Glc$_{IV}$-1 | 106.3 | 4.28 d (7.8) |
| Glc$_{IV}$-2 | 75.5 | 3.20 m |
| Glc$_{IV}$-3 | 77.9-78.4$^\Psi$ | 3.32 m |
| Glc$_{IV}$-4 | 71.3-71.7$^\S$ | 3.37 m |

TABLE 63-continued $^1$H and $^{13}$C NMR (500 and 125 MHz, CD$_3$OD), assignments of the CC-00485 C-3 glycoside.

| Position | $^{13}$C | $^1$H |
|---|---|---|
| Glc$_{IV}$-5 | 76.1 | 3.43 m |
| Glc$_{IV}$-6 | 67.6 | 3.63 m |
|              |      | 3.91 dd (10.7, 4.9) |
| Glc$_{VI}$-1 | 100.1 | 4.83 d (3.7) |
| Glc$_{VI}$-2 | 73.7 or 73.8 | 3.36 m |
| Glc$_{VI}$-3 | 75.1 | 3.64 m |
| Glc$_{VI}$-4 | 71.3-71.7$^\S$ | 3.31 m |
| Glc$_{VI}$-5 | 73.4 | 3.62 m |
| Glc$_{VI}$-6 | 62.5 | 3.67 m, 3.78 m |

$^\Psi$Five carbon resonances at 77.9-78.4 ppm (77.94, 78.03, 78.21, 78.35 and 78.37 ppm), hence chemical shifts could not be unequivocally assigned.
$^\S$Three carbon resonances at 71.3-71.7 ppm (71.31, 71.57 and 71.68 ppm), hence chemical shifts could not be unequivocally assigned.

A summary of the $^1$H and $^{13}$C chemical shifts for the glycoside at C-24 are found in Table 64.

TABLE 64

$^1$H and $^{13}$C NMR (500 and 125 MHz, CD$_3$OD), assignments of the CC-00485 C-24 glycoside.

| Position | $^{13}$C | $^1$H |
|---|---|---|
| Glc$_I$-1 | 102.8 | 4.47 d (7.2) |
| Glc$_I$-2 | 82.4 | 3.52 m |
| Glc$_I$-3 | 77.9-78.4$^\Psi$ | 3.55 m |
| Glc$_I$-4 | 71.3-71.7$^\S$ | 3.32 m |
| Glc$_I$-5 | 77.9-78.4$^\Psi$ | 3.26 m |
| Glc$_I$-6 | 62.5 | 3.63 m, 3.85 m |
| Glc$_{III}$-1 | 105.1 | 4.66 d (7.8) |
| Glc$_{III}$-2 | 75.7 | 3.27 m |
| Glc$_{III}$-3 | 77.9-78.4$^\Psi$ | 3.36 m |
| Glc$_{III}$-4 | 72.1 | 3.23 m |
| Glc$_{III}$-5 | 77.9-78.4$^\Psi$ | ~3.26 m |
| Glc$_{III}$-6 | 63.3 | 3.64 m, 3.85 m |

$^\Psi$Five carbon resonances at 77.9-78.4 ppm (77.94, 78.03, 78.21, 78.35 and 78.37 ppm), hence chemical shifts could not be unequivocally assigned.
$^\S$Three carbon resonances at 71.3-71.7 ppm (71.31, 71.57 and 71.68 ppm), hence chemical shifts could not be unequivocally assigned.

The structure of CC-00485 was determined to be mogro-3-O-{[α-D-glucopyranosyl-(1→6)]-β-D-glucopyranoside}-24-O-{[β-D-glucopyranosyl-(1→2)]-β-D-glucopyranoside}.

Example 10: Preparation, Purification and Characterization of CC-00467

601.6 mg of Mogroside IV (final concentration 1.0 mM) was dissolved in a reaction mixture containing 100 mM of Potassium Phosphate buffer pH 7.0, 3 mM of MgC$_2$, 0.25 M of Sucrose, 0.25 mM of UDP-glucose, 10 vol % of UGT-2/BcGT-1 lysate and 1 vol % of AtSUS lysate (expressing *A. thaliana* sucrose synthase). The final volume was 500 mL. The reaction mixture was allowed to stir magnetically at 30° C. while taking 500 µL samples at regular intervals. These samples were quenched with 40 µL of 2 N H$_2$SO$_4$ and 460 µL of 80% methanol. After centrifugation at 13000×g for 2 minutes, the samples were analyzed by HPLC. After 24 h the reaction mixture was acidified with 2 N H$_2$SO$_4$ to reach a final pH of 3.0. After centrifugation at 5000 rpm for 10 min, the supernatant was isolated and the residue after centrifugation was suspended in 60 mL of water. This suspension was centrifugated for 10 min at 5000 rpm and the supernatants were combined. 50 g of Diaion HP-20 resin were added and the resulting mixture was stirred for 1 h. The resin was washed twice by stirring with 500 mL of water for 1 h. Desorption was performed by stirring three times with 500 mL of 80% ethanol for 1 h. The combined desorption phases were evaporated to dryness providing a waxy solid that contained CC-00464, CC-00467 and CC-00468

HPLC Analysis. HPLC analyses were performed on an Agilent 1200 system coupled with variable wavelength detector (VWD) detector. Samples from multiple process and final purity evaluation were performed using the method conditions described in Table 65.

TABLE 65

Analytical HPLC conditions for fraction analysis in multiple processes and final purity evaluation

| Column: | Phenomenex Polar RP 80A (250 × 4.6 mm, 4 μm) |
|---|---|
| Column Temperature | 55° C. |
| Sample Temperature | Ambient |
| Mobile Phase A and B | A: Water and B: Acetonitrile |
| Flow Rate | 1 mL/min |
| Injection Volume | 20 μL |
| Detection @ UV | 210 nm |
| Runtime | 38 min |

| Gradient | | |
|---|---|---|
| Time (min) | % A | % B |
| 0 | 95 | 5 |
| 7 | 75 | 25 |
| 17 | 70 | 30 |
| 27 | 25 | 75 |
| 27.5 | 5 | 95 |
| 32.5 | 5 | 95 |
| 35 | 95 | 5 |
| 38 | 95 | 5 |

Primary Preparative HPLC Analysis. Primary processing was performed using Kinetex EVO C18 100 A° column (250×21.2 mm, 5 μm) on Agilent preparative HPLC coupled with UV-Vis detector. Details of preparative primary processing method conditions are summarized in Table 66. Approximately 1 g of #GM-3604-022-2 was processed using the primary preparative HPLC method. The purity of the fraction was determined using the analytical method summarized in above.

TABLE 66

Preparative HPLC method conditions for primary processing of # GM-3604-022-2

| Column | Kinetex EVO C18 100 A° (250 × 21.2 mm, 5 μm) |
|---|---|
| Detection | UV @ 210 nm |
| Mobile Phase: A | MilliQ-water |
| Mobile Phase: B | Acetonitrile |
| Elution | Gradient |
| Flow Rate | 15.0 mL/min |
| Sample preparation | 1 g dissolved in ~8.0 mL of diluent (milli-Q-water:Acetonitrile; 8:2 v/v) |
| Injection volume | 300 μL |
| Run time | 35.0 min |

| Gradient | Time | % A | % B |
|---|---|---|---|
| | 0 | 80 | 20 |
| | 30 | 75 | 25 |
| | 31 | 80 | 20 |
| | 35 | 80 | 20 |

| Time region for collected | 19.0 to 20.5 min |
|---|---|
| Target fraction | (Peak ID:GM-3604-022-2-P11) |

Secondary HPLC Processing Method: The secondary processing of Peak ID: GM-3604-022-2-P11 was performed using Kinetex EVO C18 100 A° column (250×21.2 mm, 5 μm) on Agilent preparative HPLC coupled with UV-Vis detector. Details of preparative secondary processing method conditions are summarized in Table 67. Approximately 37 mg of GM-3604-022-2-P11 (Lot #IN-SSB-C-116-11) was processed. The final yield of Peak ID: GM-3604-022-2-P11-B (Lot #IN-SSB-C-118-12) was 12 mg with purity 92.9% (area %).

TABLE 67

Preparative HPLC method conditions for secondary processing of Peak ID: GM-3604-022-2-P11 (Lot # IN-SSB-C-116-11)

| Column | Kinetex EVO C18 100 A° (250 × 21.2 mm, 5 μm) |
|---|---|
| Detection | UV@210 nm |
| Mobile Phase: A | Water |
| Mobile Phase: B | Acetonitrile |
| Elution | Isocratic |
| Flow Rate | 15.0 mL/min |
| Sample preparation | 37 mg dissolved in ~1 mL of diluent (Milli-Q-water:Acetonitrile ; 8:2 v/v) |
| Injection volume | 200 μL |
| Run time | 45 min |

| Time | % A | % B |
|---|---|---|
| 45 | 80 | 20 |

| Time region for collected | 34.0 to 36.0 min |
|---|---|
| Target fraction | (Peak ID:GM-3604-022-2-P11-B) |

Isolation Procedure: The collected fractions from the preparative processing were pooled up and lyophilized using Labconco Lyopholizer, (collector temperature maintained at −44° C. under vacuum).

MS and MS/MS. MS and MS/MS data were generated using a Waters QTof Premier mass spectrometer equipped with an electrospray ionization source. The sample was analyzed by negative ESI. The sample (~0.2 mg) was diluted with 50:50 ACN:$H_2O$ to a concentration of ~0.2 mg/mL and introduced via direct infusion.

The ESI-TOF mass spectrum acquired by infusing a sample of CC-00467 showed a [M−H]$^-$ ion at m/z 1285.6426. The mass of the [M−H]$^-$ ion was in good agreement with the molecular formula $C_{60}H_{102}O_{29}$ (calcd for $C_{60}H_{101}O_{29}$: 1285.6429, error: −0.2 ppm) expected. The MS data confirmed a nominal mass of 1286 Daltons with the molecular formula, $C_{60}H_{102}O_{29}$. The ions observed at m/z 1331.6481 and 1399.6356 were likely due to [M−H+HCOOH]$^-$ and [M−H+TFA]$^-$, respectively.

The MS/MS spectrum of CC-00467, selecting the [M−H]$^-$ ion at m/z 1285.6 for fragmentation, indicated sequential loss of five glucose units at m/z 1123.6056, 961.5544, 799.4907, 637.4368, and 475.3901 indicated presence of five glucose units in the structure. Following the loss of one sugar from the structure, another fragmentation pathway was also observed in the spectrum, which corresponded to loss of water molecule from the central triterpene core to give m/z 1105.6382 followed by sequential loss of four glucose units at m/z 943.5493, 781.4868, 619.4215 and 459.3535. The ion observed at m/z 383.1249 was likely due to the loss of five glucose, water and C-24 isopropyl hydroxyl units.

NMR. The sample was prepared by dissolving ~1.0 mg in 130 μL of $CD_3OD$ and NMR data were acquired on a Bruker Avance 500 MHz instrument equipped with a 2.5 mm inverse probe and a 5 mm broad band probe. The $^1$H NMR spectrum was referenced to the CHD$_2$OD resonance at $\delta_H$ 3.30 and $^{13}$C NMR spectrum was referenced to the CD$_3$OD resonance at $\delta_C$ 49.0.

A series of NMR experiments including $^1$H NMR, $^3$C NMR, $^1$H-$^1$H COSY, HSQC-DEPT, HMBC, ROESY, and 1D TOCSY were acquired to allow assignment of CC-00467.

A summary of the $^1$H and $^{13}$C chemical shifts for the aglycone are found in Table 68:

TABLE 68

$^1$H and $^{13}$C NMR (500 and 125 MHz, CD$_3$OD), assignments of the CC-00467 aglycone.

| Position | $^{13}$C | $^1$H |
|---|---|---|
| 1 | 27.2 | 1.49 m |
|  |  | 2.22 m |
| 2 | 29.5 | 1.89 m |
|  |  | 1.93 m |
| 3 | 88.3 | 3.47 m |
| 4 | 42.8 | — |
| 5 | 144.9 | — |
| 6 | 119.6 | 5.47 brd (5.8) |
| 7 | 25.1 | 1.81 m |
|  |  | 2.38 m |
| 8 | 44.7 | 1.66 m |
| 9 | 40.9 | — |
| 10 | 37.2 | 2.49 brd (12.0) |
| 11 | 79.4 | 3.85 m |
| 12 | 41.1 | 1.81 m |
|  |  | 1.86 m |
| 13 | 48.3 | — |
| 14 | 50.6 | — |
| 15 | 35.4 | 1.13 m |
|  |  | 1.21 m |
| 16 | 29.3 | 1.32 m |
|  |  | 1.99 m |
| 17 | 51.6 | 1.63 m |
| 18 | 17.2 | 0.91 s |
| 19 | 26.2 or 26.3 | 1.11 s |
| 20 | 37.5 | 1.47 m |
| 21 | 19.3 | 0.97 brd (4.9) |
| 22 | 34.5 | 1.47 m |
|  |  | 1.52 m |
| 23 | 29.3 | 1.47 m |
|  |  | 1.64 m |
| 24 | 89.4 | 3.47 m |
| 25 | 73.7 | — |
| 26 | 26.6† | 1.14 s† |
| 27 | 24.7† | 1.17 s† |
| 28 | 27.9 | 1.07 s |
| 29 | 26.2 or 26.3 | 1.18 s |
| 30 | 19.9 | 0.88 s |

†Assignments can be interchanged.

A summary of the $^1$H and $^{13}$C NMR for the C-3 glycoside is provided in Table 69.

TABLE 69

$^1$H and $^{13}$C NMR (500 and 125 MHz, CD$_3$OD), assignments of the C-3 glycoside.

| Position | $^{13}$C | $^1$H |
|---|---|---|
| Glc$_{II}$-1 | 106.0 | 4.33 d (7.8) |
| Glc$_{II}$-2 | 75.0 | 3.39 m |
| Glc$_{II}$-3 | 87.8 | 3.50 m |
| Glc$_{II}$-4 | 70.0 | 3.43 m |
| Glc$_{II}$-5 | 77.0 | 3.45 m |
| Glc$_{II}$-6 | 69.6 | 4.06 brd (11.2) |
|  |  | 3.83 m |
| Glc$_{I'}$-1 | 104.9 | 4.43 d (7.8) |
| Glc$_{I'}$-2 | 75.2 | 3.18 m |

TABLE 69-continued $^1$H and $^{13}$C NMR (500 and 125 MHz, CD$_3$OD), assignments of the C-3 glycoside.

| Position | $^{13}$C | $^1$H |
|---|---|---|
| Glc$_{I'}$-3 | 77.8-78.2§ | 3.35 m |
| Glc$_{I'}$-4 | 71.6 or 71.7 | 3.28 m |
| Glc$_{I'}$-5 | 77.8-78.2§ | 3.25 m |
| Glc$_{I'}$-6 | 62.6-63.3€ | 3.85 m, 3.65 m |
| Glc$_{VI}$-1 | 105.2† | 4.55 d (7.9) |
| Glc$_{VI}$-2 | 75.5 | 3.25 m |
| Glc$_{VI}$-3 | 77.8-78.2§ | 3.37 m |
| Glc$_{VI}$-4 | 71.6 or 71.7 | 3.26 m |
| Glc$_{VI}$-5 | 77.8-78.2§ | 3.30 m |
| Glc$_{VI}$-6 | 62.6-63.3€ | 3.87 m, 3.63 m |

§Seven carbon resonances in the range of 77.8-78.2 ppm (77.82, 77.88, 77.98, 78.05, 78.17 and 78.21 ppm; two carbons resonances overlap at 77.98 ppm), hence chemical shifts could not be unequivocally assigned.
€Four carbon resonances at 62.6-63.3 ppm (62.57, 62.65, 62.78 and 63.34 ppm), hence chemical shifts could not be unequivocally assigned.
†Two carbon resonances at 105.2 ppm (105.16 and 105.18 ppm).

A summary of the $^1$H and $^{13}$C NMR for the C-24 glycoside is provided in Table 70:

TABLE 70

$^1$H and $^{13}$C NMR (500 and 125 MHz, CD3OD), assignments of the C-24 glycoside.

| Position | $^{13}$C | $^1$H |
|---|---|---|
| Glc$_I$-1 | 102.7 | 4.47 d (7.2) |
| Glc$_I$-2 | 82.5 | 3.52 m |
| Glc$_I$-3 | 78.4 | 3.55 m |
| Glc$_I$-4 | 71.4 | 3.32 m |
| Glc$_I$-5 | 77.8-78.2§ | 3.27 m |
| Glc$_I$-6 | 62.6-63.3€ | 3.85 m, 3.63 m |
| Glc$_{III}$-1 | 105.2† | 4.65 d (8.1) |
| Glc$_{III}$-2 | 75.7 | 3.27 m |
| Glc$_{III}$-3 | 77.8-78.2§ | 3.36 m |
| Glc$_{III}$-4 | 72.1 | ~3.25 m |
| Glc$_{III}$-5 | 77.8-78.2§ | ~3.24 m |
| Glc$_{III}$-6 | 62.6-63.3€ | 3.85 m, 3.65 m |

§Seven carbon resonances in the range of 77.8-78.2 ppm (77.82, 77.88, 77.98, 78.05, 78.17 and 78.21 ppm; two carbons resonances overlap at 77.98 ppm), hence chemical shifts could not be unequivocally assigned.
€Four carbon resonances at 62.6-63.3 ppm (62.57, 62.65, 62.78 and 63.34 ppm), hence chemical shifts could not be unequivocally assigned.
†Two carbon resonances at 105.2 ppm (105.16 and 105.18 ppm).

The structure of CC-00467 was determined to be mogro-3-O-{[β-D-glucopyranosyl (1→3)]-[β-D-glucopyranosyl-(1→6)]-β-D-glucopyranoside}-24-O-[β-D-glucopyranosyl-(1→2)]-β-D-glucopyranoside}.

Example 11: Preparation, Purification and Characterization of CC-00483

483.8 mg of Mogroside IIIe (final concentration 1.0 mM) was dissolved in a reaction mixture containing 100 mM of Potassium Phosphate buffer pH 7.0, 3 mM of MgCl$_2$, 0.25 M of Sucrose, 0.25 mM of UDP-glucose, 10 vol % of UGT-2 lysate and 1 vol % of AtSUS containing lysate (expressing *A. thaliana* sucrose synthase). The final volume was 500 mL. The reaction mixture was allowed to stir magnetically at 30° C. while taking 500 μL samples at regular intervals. These samples were quenched with 40 μL of 2 N H$_2$SO$_4$ and 460 μL of 80% methanol. After centrifugation at 13000 g for 2 minutes the samples were analyzed by HPLC.

After 24 h the reaction mixture was acidified with 2 N H$_2$SO$_4$ to reach a final pH of 3.0. 500 mL of ethanol was added and the resulting suspension was stored overnight at 4° C. After centrifugation at 10000×g* for 10 min, the supernatant was isolated and evaporated under reduced pressure until 200 mL. The volume of the concentrate was adjusted with water until 500 mL and 20 g of Diaion HP-20 resin was added and the resulting mixture was stirred for 1 h. The resin was washed twice by stirring with 200 mL of water for 1 h. Desorption was performed by stirring three times with 200 mL of 80% ethanol for 1 h. The combined desorption phases were evaporated to dryness to provide a waxy solid.

HPLC. Preparative HPLC analyses were performed on an Agilent preparative HPLC coupled with a UV-Vis detector using a Kinetex EVO C18 100 A° column (250×21.2 mm, 5 µm). Approximately 0.5 g was processed using the preparative HPLC method described in Table 71. The purity of the fraction was determined using the analytical method summarized in Table 72 (performed on an Agilent 1200 system coupled with variable wavelength detector (VWD)). Fraction of Peak ID: GM-3502-169-3-F5 (target fraction time region: 16.00 to 17.00 min), collected from the processing of whole quantity was pooled and lyophilized. The final yield of Peak ID: GM-3502-169-3-F5 was 4 mg with purity 89.9% (area %).

TABLE 71

Preparative HPLC method conditions

| | |
|---|---|
| Column: | Kinetex Evo C18 |
| | (250 × 21.2 mm, 5 µm) |
| Mobile Phase A and B | A: Water and B: Acetonitrile |
| Flow Rate | 15.0 mL/min |
| Injection Volume | 500 µL |
| Detection @ UV | 210 nm |
| Runtime | 35.0 min |
| Diluent | Water:Acetonitrile(80:20; % v/v) |
| Sample preparation | 0.5 g in 5.0 mL of diluent |
| | (After adding diluent to the sample, solution was filtered through 0.45 um filter) |

Gradient elution

| Time (min) | % A | % B |
|---|---|---|
| 0 | 80 | 20 |
| 25 | 70 | 30 |
| 27 | 20 | 80 |
| 29 | 20 | 80 |
| 30 | 80 | 20 |
| 35 | 80 | 20 |

| | |
|---|---|
| Time Region for collected Target fraction | RT 16.00 to 17.00 min (Peak ID: GM-3502-169-3-F5; Lot#IN-GKR-B-33-5) |

TABLE 72

Analytical HPLC conditions for fraction analysis in multiple processes and final purity evaluation

| | |
|---|---|
| Column: | Phenomenex Polar RP 80A |
| | (250 × 4.6 mm, 4 µm) |
| Column Temperature | 55° C. |
| Sample Temperature | Ambient |
| Mobile Phase A and B | A: Water and B: Acetonitrile |
| Flow Rate | 1 mL/min |
| Injection Volume | 20 µL |
| Detection @ UV | 210 nm |
| Runtime | 38 min |

Gradient

| Time (min) | % A | % B |
|---|---|---|
| 0 | 95 | 5 |
| 7 | 75 | 25 |
| 17 | 70 | 30 |
| 27 | 25 | 75 |
| 27.5 | 5 | 95 |
| 32.5 | 5 | 95 |
| 35 | 95 | 5 |
| 38 | 95 | 5 |

Isolation Procedure: The collected fractions from the preparative processing were pooled up and lyophilized using Labconco Lyopholizer, (collector temperature maintained at −44° C. under vacuum). Mass Spectrometry: The ESI mass spectrum acquired by infusing a sample of isolated CC-00483 showed a [M−H]$^-$ ion at m/z 1123.51.

Figure 2:
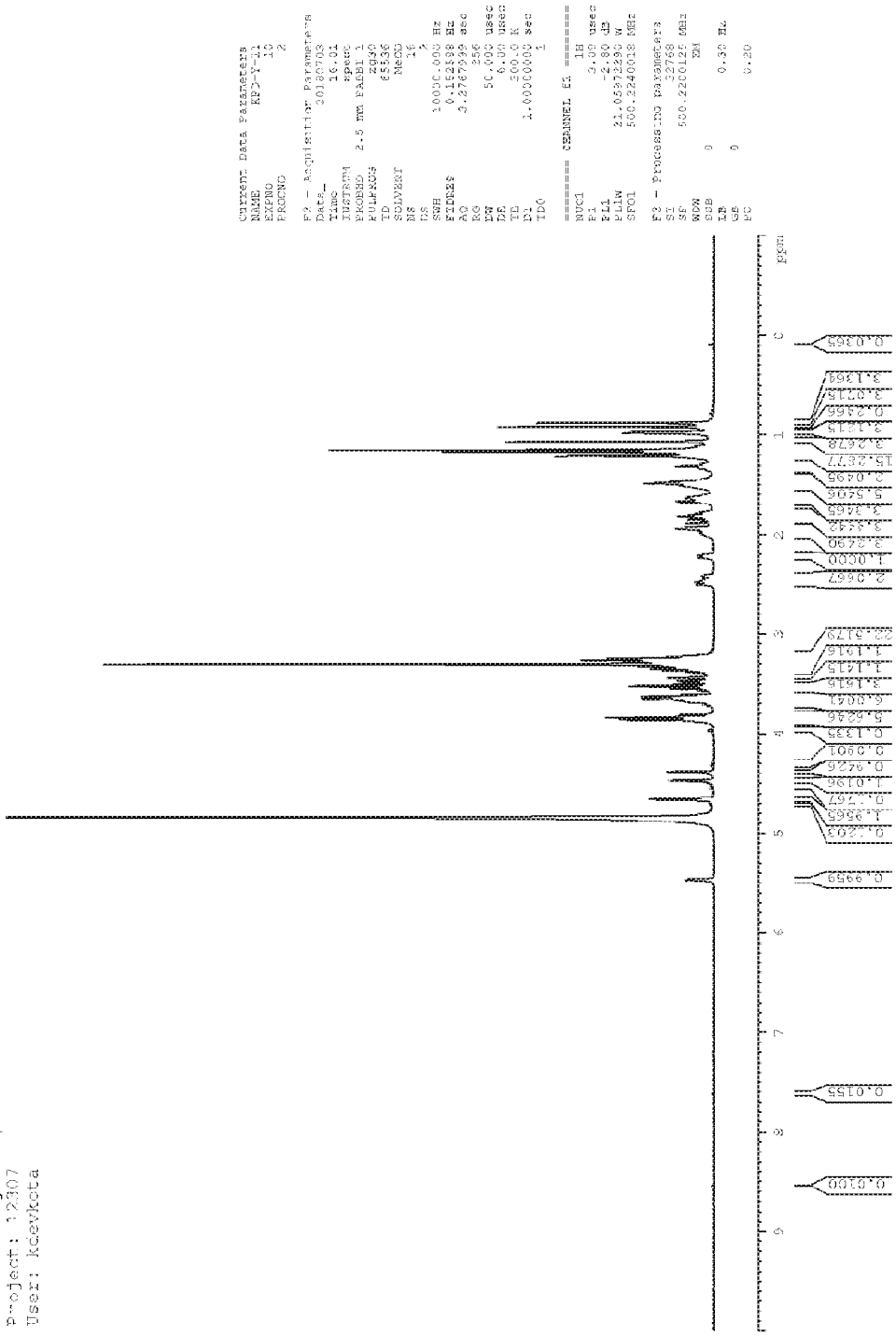
FIG. 2: Shows the $^1$H NMR Spectrum (500 MHz, 300K) of CC-00483 in $CD_3OD$.
Figure 3:
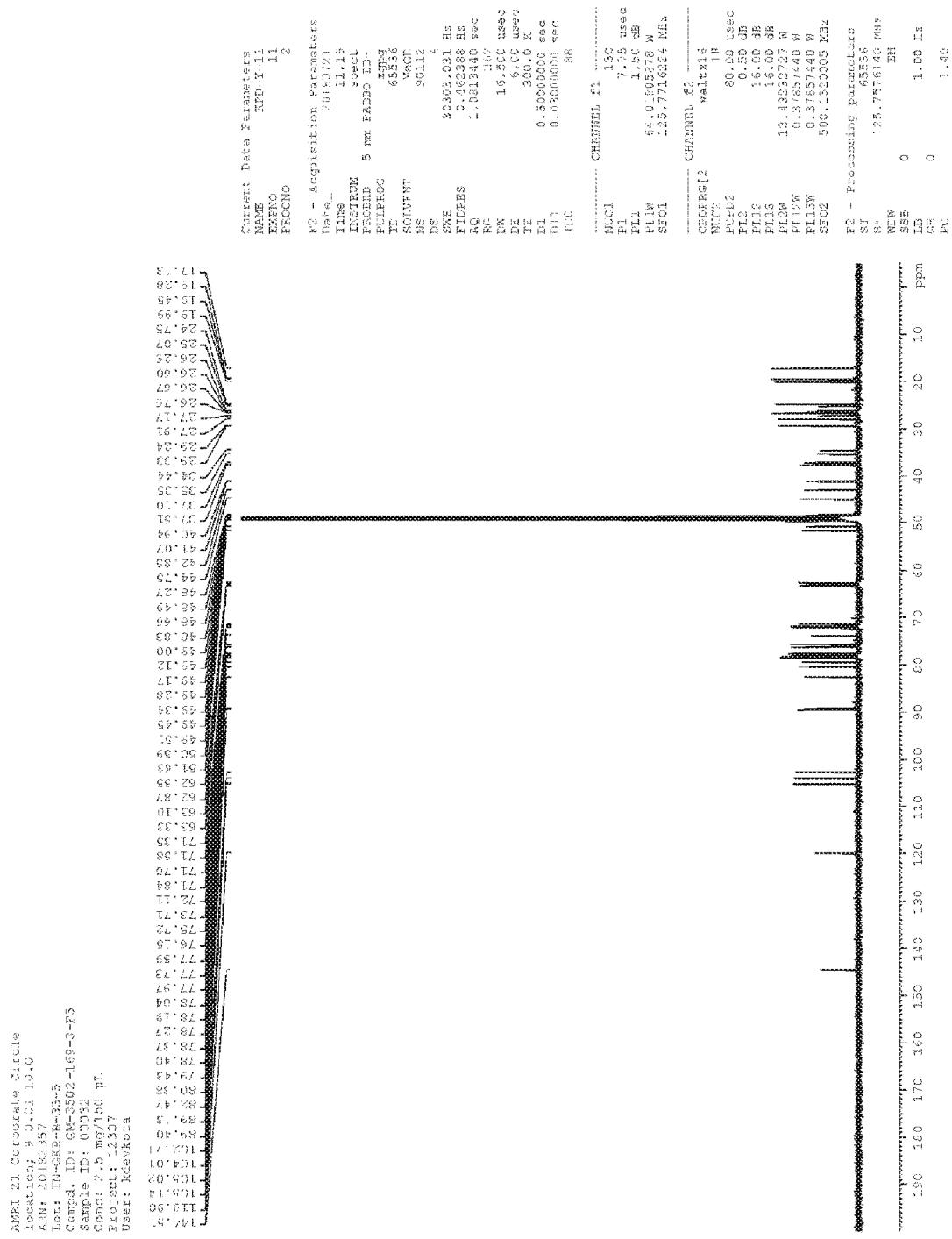
FIG. 3: Shows the $^{13}$C NMR Spectrum (125 MHz, 300K) of CC-00483 in $CD_3OD$.

NMR spectral analyses (FIG. 2 and FIG. 3) were performed to elucidate the structure of CC-00483.

Example 12: Preparation, Purification and Characterization of CC-00468

CC-00468 was isolated from the reaction product of Example 10. The reaction product was purified by HPLC using the analytical and preparative methods described in Example 10. The target fraction using the primary preparative HPLC method had a retention time of 20.50 to 21.50 minutes. The target fraction in the secondary preparative HPLC method had a retention time of 30.50 to 32.00 minutes. The final yield was 2.5 mg with purity 96.8% (area %). The collected fractions from preparative processing were pooled and lyophilized using Labconco Lyopholizer, (collector temperature maintained at −44° C. under vacuum).

Mass Spectrometry: The ESI mass spectrum acquired by infusing a sample of isolated CC-00468 showed a [M−H]$^-$ ion at m/z 1285.0.

Figure 4:
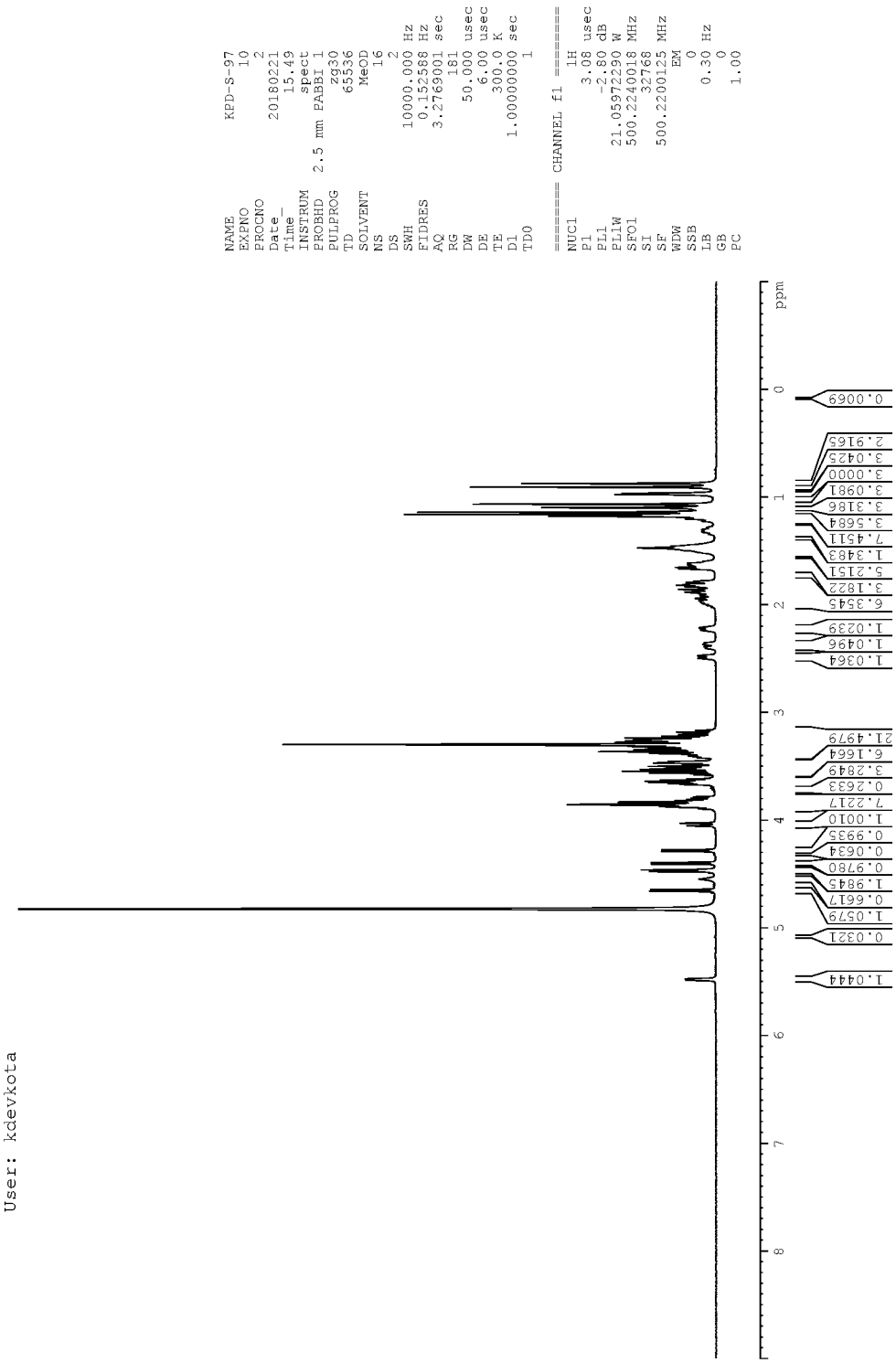
FIG. 4: Shows the $^1$H NMR Spectrum (500 MHz, 300K) of CC-00468 in $CD_3OD$.
Figure 5:
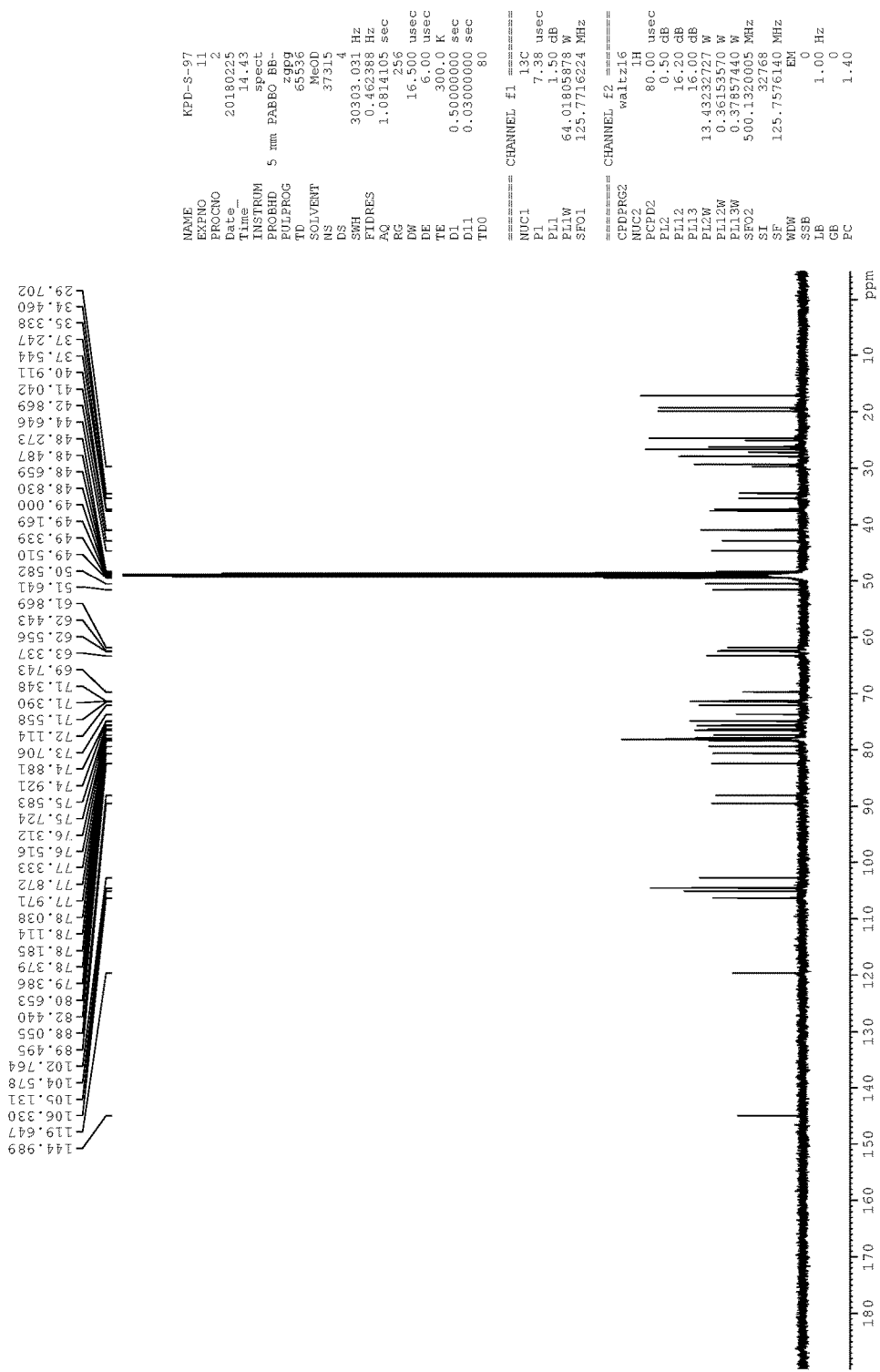
FIG. 5: Shows the $^{13}$C NMR Spectrum (125 MHz, 300K) of CC-00468 in $CD_3OD$.

NMR spectral analyses (FIG. 4 and FIG. 5) were performed to elucidate the structure of CC-00468.

Example 13: Preparation, Purification and Characterization of CC-00464

CC-00464 was isolated from the reaction product of Example 10. The reaction product was purified by HPLC using the analytical and preparative methods described in Example 10. The target fraction using the primary preparative HPLC method had a retention time of 12.21 to 13.00 minutes. The target fraction in the secondary preparative HPLC method had a retention time of 15.30 to 16.30 minutes. The final yield was 5.4 mg with purity 98.9% (area %). The collected fractions from preparative processing were pooled up and lyophilized using Labconco Lyopholizer, (collector temperature maintained at −44° C. under vacuum).

Mass Spectrometry. The ESI mass spectrum acquired by infusing a sample of isolated CC-00464 showed a [M−H]$^-$ ion at m/z 1447.92.

Figure 6:
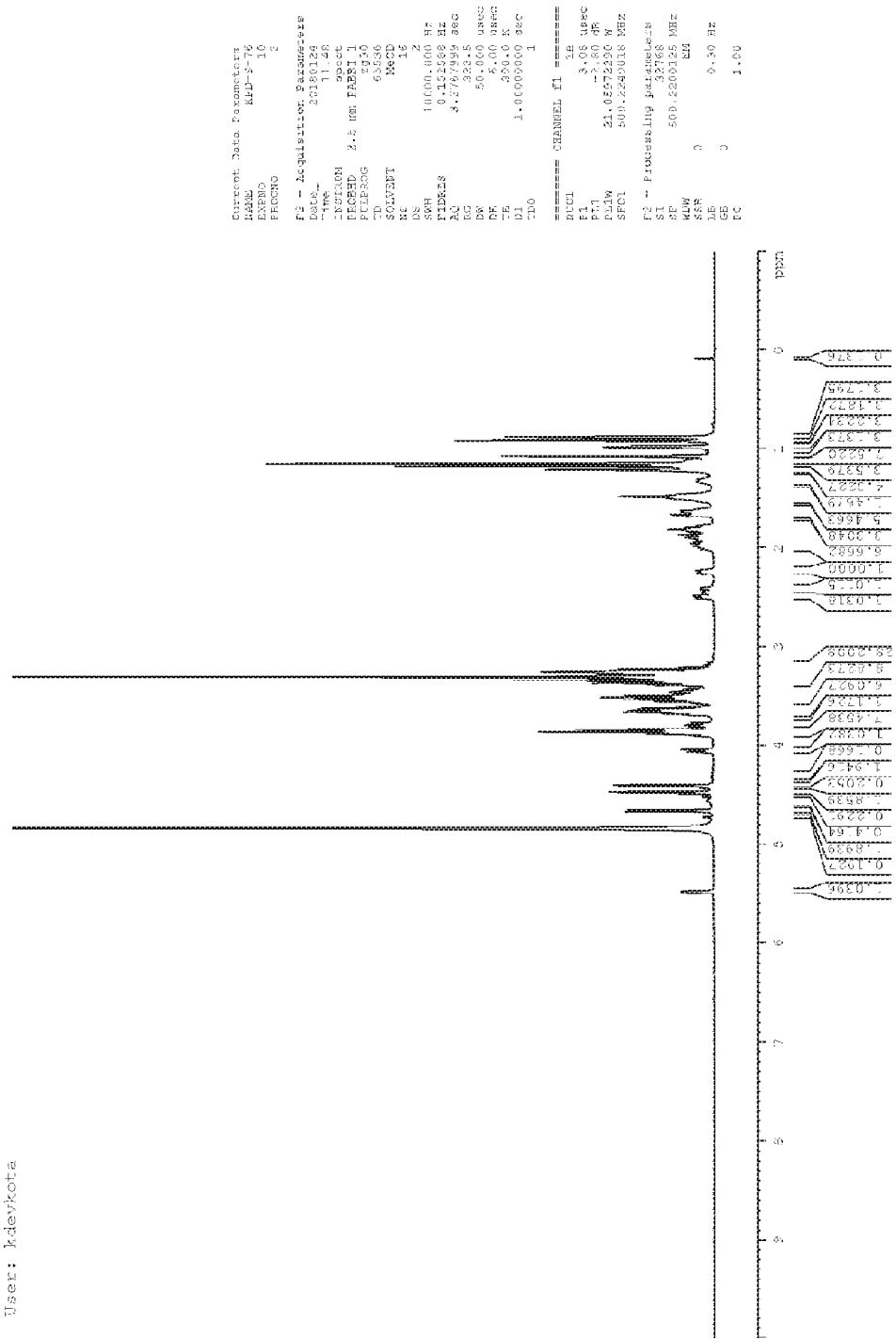
FIG. 6: Shows the $^1$H NMR Spectrum (500 MHz, 300K) of CC-00464 in $CD_3OD$.
Figure 7:
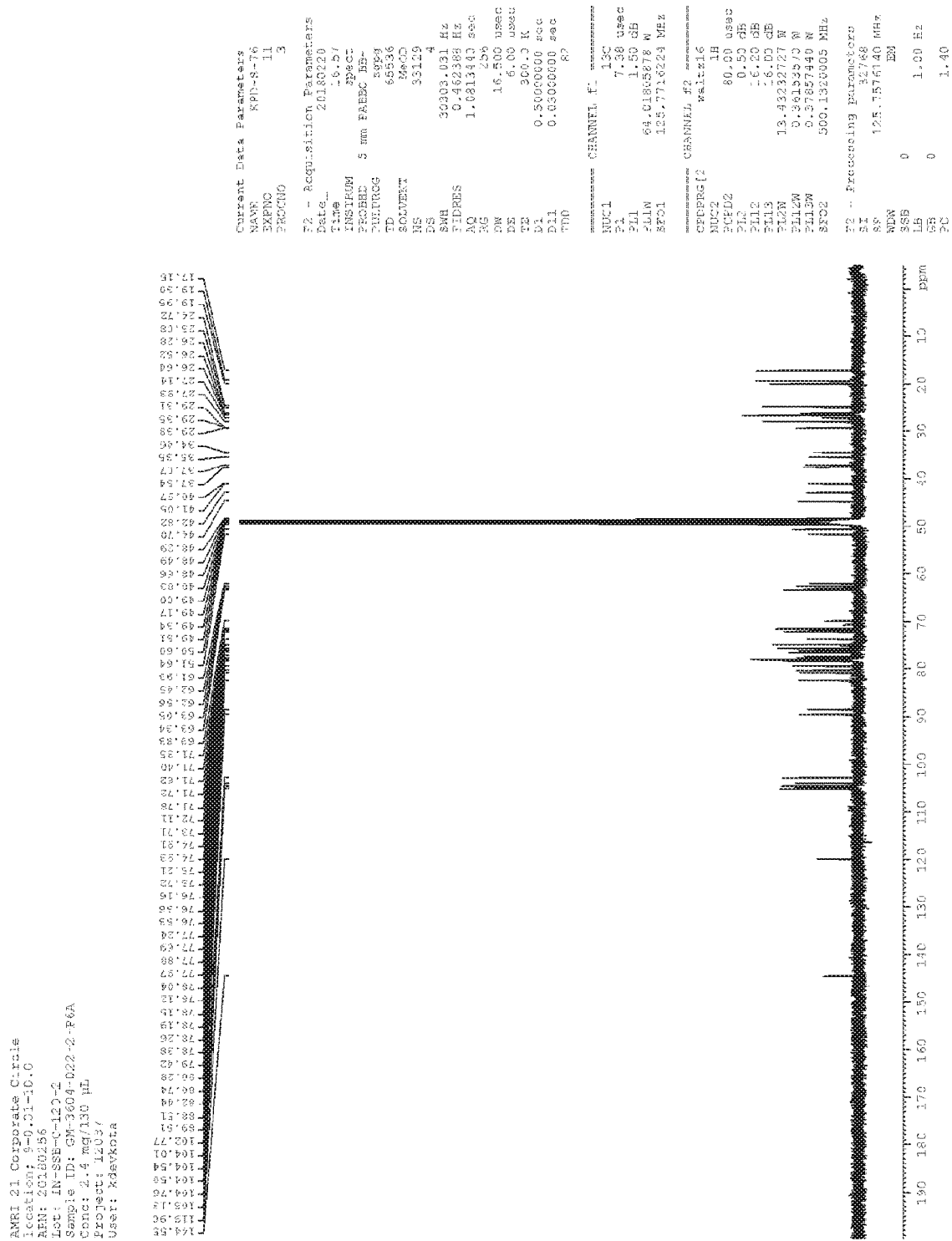
FIG. 7: Shows the $^{13}$C NMR Spectrum (125 MHz, 300K) of CC-00464 in $CD_3OD$.

NMR spectral analyses (FIG. 6 and FIG. 7) were performed to elucidate the structure of CC-00464.

Example 14: Preparation, Purification and Characterization of CC-00458

652.2 mg of Mogroside V (final concentration 1.0 mM) was dissolved in a reaction mixture containing 100 mM of Potassium Phosphate buffer pH 7.0, 3 mM of MgCl$_2$, 0.25 M of Sucrose, 0.25 mM of UDP-glucose, 10 vol % of UGT-2/BcGT-1 lysate and 1 vol % of AtSUS lysate (expressing *A. thaliana* sucrose synthase). The final volume was 500 mL. The reaction mixture was allowed to stir magnetically at 30° C. while taking 500 μL samples at regular intervals. These samples were quenched with 40 μL of 2 N $H_2SO_4$ and 460 μL of 80% methanol. After centrifugation at 13000 g for 2 minutes the samples were analyzed by HPLC.

After 24 h the reaction mixture was acidified with 2 N $H_2SO_4$ to reach a final pH of 3.0. After centrifugation at 5000 rpm for 10 min, the supernatant was isolated and the residue after centrifugation was suspended in 60 mL of water. This suspension was centrifugated for 10 min at 5000 rpm and the supernatants were combined. 50 g of Diaion HP-20 resin was added and the resulting mixture was stirred for 1 h. The resin was washed twice by stirring with 500 mL of water for 1 h. Desorption was performed by stirring three times with 500 mL of 80% ethanol for 1 h. The combined desorption phases were evaporated to dryness providing a waxy solid.

The reaction product was purified by HPLC using the analytical and primary preparative methods described in Example 10. The target fraction using the primary preparative HPLC method had a retention time of 14.00 to 15.00 minutes. The secondary preparative HPLC method used is shown in Table 73.

TABLE 73

Preparative HPLC method conditions for secondary processing

| Parameter | Description | | |
|---|---|---|---|
| Column | Kinetex EVO C18 (250 × 21.2 mm, 5 μm) | | |
| Detection | UV@210 nm | | |
| Mobile Phase: A | Milli-Q-water | | |
| Mobile Phase: B | Acetonitrile | | |
| Elution | Gradient | | |
| Flow Rate | 15.0 mL/min | | |
| Sample preparation | 11.0 mg dissolved in ~1.0 mL of diluent (Milli-Q-water) | | |
| Injection Volume | 0.3 mL | | |
| Run time | 35.0 minutes | | |
| Gradient | Time | % A | % B |
| | 0 | 80 | 20 |
| | 30 | 75 | 25 |
| | 31 | 80 | 20 |
| | 35 | 80 | 20 |
| Time Region for collected Target fraction | RT 12.55 min to 13.50 min (Peak ID: GM-3604-022-3-P6-B; Lot#IN-SSB-C-111-2) | | |

Figure 8:
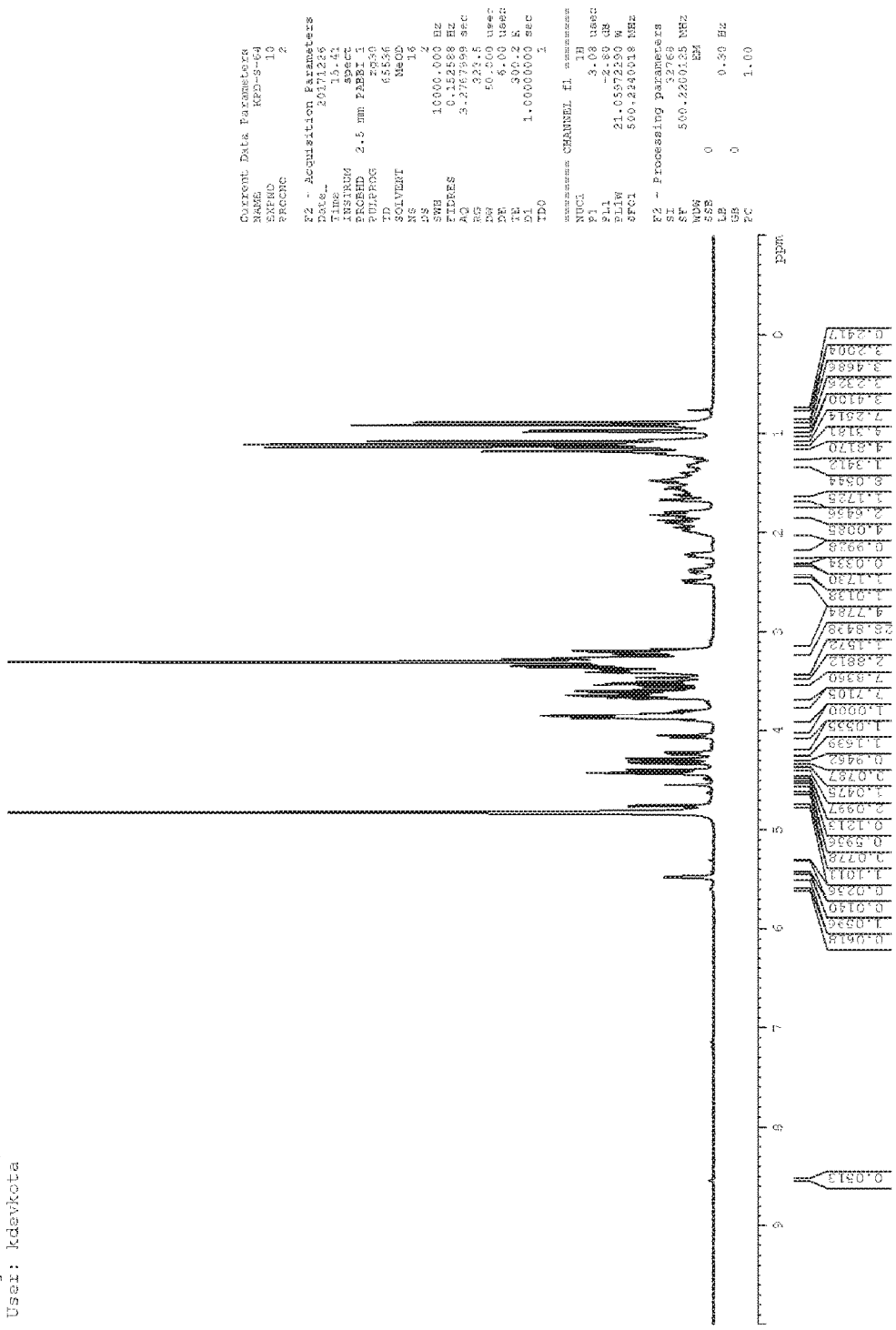
FIG. 8: Shows the $^1$H NMR Spectrum (500 MHz, 300K) of CC-00458 in $CD_3OD$.
Figure 9:
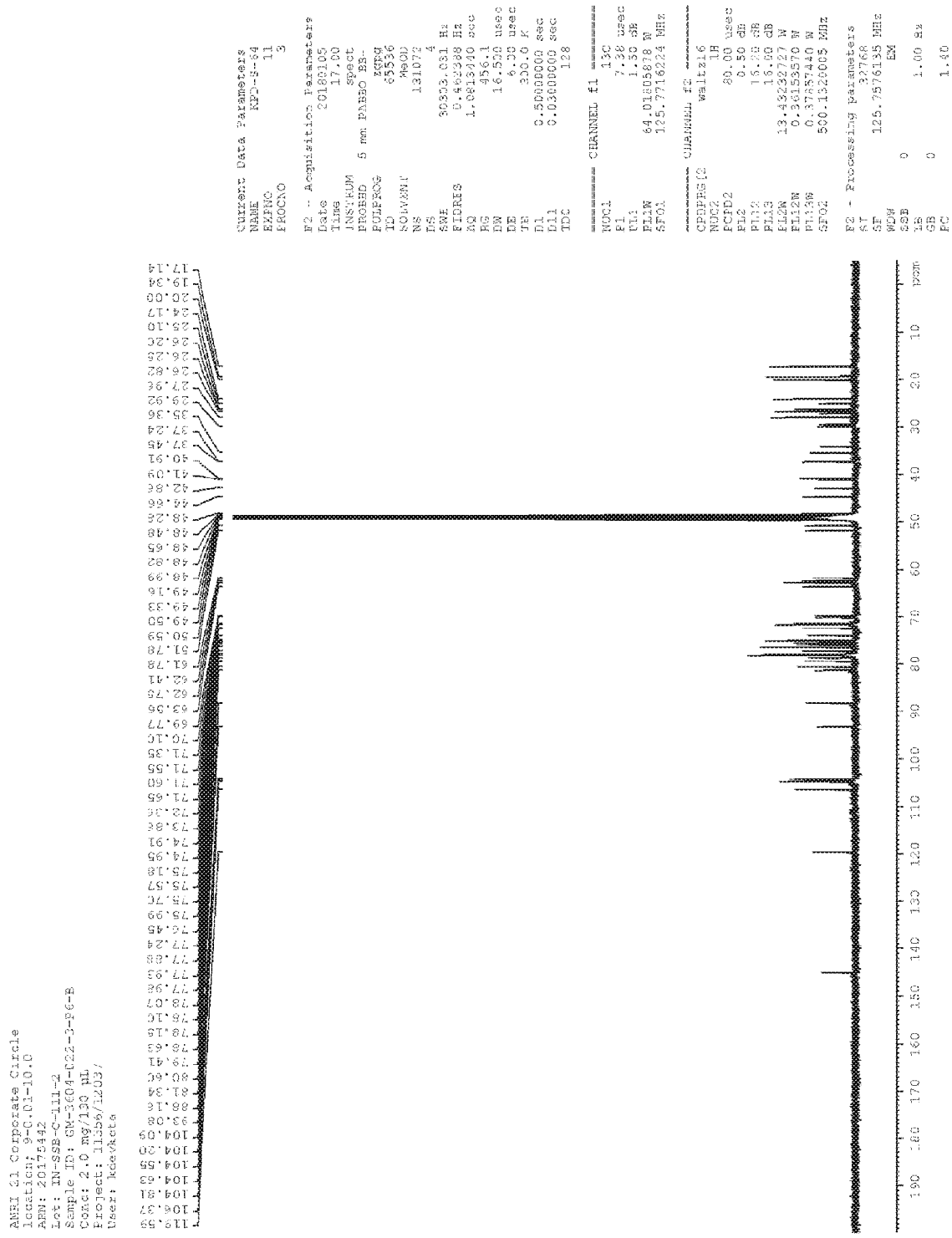
FIG. 9: Shows the $^{13}$C NMR Spectrum (125 MHz, 300K) of CC-00458 in $CD_3OD$.

NMR spectral analyses (FIG. 8 and FIG. 9) were performed to elucidate the structure of CC-00458.

The final yield was 3.0 mg with purity 76.9% (area %). The collected fractions from preparative processing were pooled up and lyophilized using Labconco Lyopholizer, (collector temperature maintained at −44° C. under vacuum).

Mass Spectrometry: The ESI mass spectrum acquired by infusing a sample of isolated CC-00458 showed a [M−H]⁻ ion at m/z 1448.11.

Example 15: Sensory Evaluation of CC-00367 and CC-00371

The following mock beverage samples were prepared:

TABLE 74

| Sweetener | Concentration (ppm) | Matrix | Temperature Tested |
|---|---|---|---|
| Reb M 95% | 400 | Water | 4° C. |
| Mog V | 400 | Water | 4° C. |
| CC-00371 | 400 | Water | 4° C. |
| CC-00367 | 400 | Water | 4° C. |

A trained sensory panel conducted the taste test. Samples were served at approximately 4° C. Panelists were instructed to take 1 sip of the sample, hold in mouth for 5 seconds, expectorate, and rate the given attributes. A 5 minute break was placed between each sample and panelists were instructed to cleanse their palates with at least 1 bite of unsalted cracker and 2 sips of filtered water. Samples were randomized within each session for each panelist.

The following attributes were evaluated:

Sweet taste intensity: maximum level of sweetness in mouth during 5 seconds

Bitter taste intensity: maximum level of bitterness in mouth during 5 seconds

Overall maximum sweet intensity: maximum sweet intensity experienced from the time the sip is taken up to 1 minute Overall maximum bitter intensity: maximum sweet intensity experienced from the time the sip is taken up to 1 minute Sweet linger intensity: sweet intensity 1 minute after tasting the sample Bitter aftertaste intensity: bitter intensity 1 minute after tasting the sample An ANOVA, with Sample as fixed effects and Panelist as random effects was used to determine significance between the samples for each attribute at the 90% and 95% Confidence Level, two-tailed. Fishers LSD was used to determine significant differences between mean scores.

The results are shown in Table 75 and depicted in FIG. 1:

TABLE 75

| Sample | Sweet Intensity In Mouth | Bitter Intensity In Mouth | Overall Max Sweetness | Overall Max Bitterness** | Sweet Linger Intensity | Bitter Aftertaste Intensity |
|---|---|---|---|---|---|---|
| Reb M 95% | 8.0 A | 1.0 B | 9.2 A | 2.0 B | 5.3 A | 1.7 B |
| Mog V | 7.0 | 0.5 | 8.5 | 1.1 | 3.5 | 0.4 |
| CC-00371 | 7.5 A | 0.9 B | 9.3 A | 2.1 B | 5.8 A | 1.5 B |
| CC-00367 | 3.8 B | 1.3 B | 4.9 B | 2.2 B | 2.6 B | 1.4 B |

*A 3-way ANOVA (Panelist, Sample, Panelist *Sample) was used to compare the sweeteners for each attribute at $p < 0.05$

*Within a column, means with a different uppercase letter beside them are significantly different at $p < 0.05$

Example 16: Sensory Evaluation of CC-00401 and CC-00403

The following mock beverage samples were prepared:

TABLE 76

| Sweetener | Concentration | Matrix | Temperature Tested |
|---|---|---|---|
| Reference: 7% Sucrose | n/a | Water | 4° C. |
| CC-00401 | 400 ppm | Water | 4° C. |
| CC-00403 | 400 ppm | Water | 4° C. |

A trained sensory panel conducted the taste test. Samples were served at approximately 4° C. Panelists were instructed to take 1 sip of the sample, hold in mouth for 5 seconds, expectorate, and rate the given attributes. A 5 minute break was placed between each sample and panelists were instructed to cleanse their palates with at least 1 bite of unsalted cracker and 2 sips of filtered water. Samples were randomized within each session for each panelist.

The following attributes were evaluated:

Sweet taste intensity: maximum level of sweetness in mouth during 5 seconds

Bitter taste intensity: maximum level of bitterness in mouth during 5 seconds

Overall maximum sweet intensity: maximum sweet intensity experienced from the time the sip is taken up to 1 minute Overall maximum bitter intensity: maximum sweet intensity experienced from the time the sip is taken up to 1 minute Sweet linger intensity: sweet intensity 1 minute after tasting the sample Bitter aftertaste intensity: bitter intensity 1 minute after tasting the sample An ANOVA, with Sample as fixed effects and Panelist as random effects was used to determine significance between the samples for each attribute at the 90% and 95% Confidence Level, two-tailed. Fishers LSD was used to determine significant differences between mean scores.

The results are shown in Table 77:

TABLE 77

Means table of Sweetness and Bitterness Perception for CC-00401, CC-00403, & 7% Sucrose at 4° C.

| Sample | Sweetness | | | Bitterness | | |
|---|---|---|---|---|---|---|
| | In Mouth | Overall Max | Linger (~60 sec) | In Mouth | Overall Max | Linger (~60 sec) |
| Reference: 7% Sucrose | 7.2 ± 0.9 | 7.4 ± 0.8 | 2.1 ± 1.8 | 2.3 ± 2.3 | 2.8 ± 2.1 | 0.8 ± 1.1 |
| CC-00401 | 6.2 ± 2.3 | 6.9 ± 2.5 | 2.5 ± 2.2 | 2.9 ± 2.6 | 3.9 ± 2.9 | 2.3 ± 2.7 |
| CC-00403 | 6.3 ± 1.4 | 7.0 ± 1.5 | 3.1 ± 2.5 | 2.6 ± 3.0 | 5.0 ± 3.4 | 2.2 ± 3.4 |

*Overall Maximum Sweetness and Bitterness includes Sweet and Bitter Intensity in Mouth scores if the attribute peaks while in mouth; Standard deviation

Example 17: Sensory Evaluation of CC-00436

The following mock beverages were prepared:

TABLE 78

| Sample Description | | | |
|---|---|---|---|
| Sweetener | Concentration | Matrix | Temperature Tested |
| Reference: 5% Sucrose | n/a | Water | 4° C. |
| CC-00436 | 400 ppm | Water | 4° C. |

A trained sensory panel conducted the taste test. Samples were served at approximately 4° C. Panelists were instructed to take 1 sip of the sample, hold in mouth for 5 seconds, expectorate, and rate the given attributes. A 5 minute break was placed between each sample and panelists were instructed to cleanse their palates with at least 1 bite of unsalted cracker and 2 sips of filtered water. Samples were randomized within each session for each panelist.

The following attributes were evaluated:

Sweet taste intensity: maximum level of sweetness in mouth during 5 seconds

Bitter taste intensity: maximum level of bitterness in mouth during 5 seconds

Overall maximum sweet intensity: maximum sweet intensity experienced from the time the sip is taken up to 1 minute Overall maximum bitter intensity: maximum sweet intensity experienced from the time the sip is taken up to 1 minute Sweet linger intensity: sweet intensity 1 minute after tasting the sample Bitter aftertaste intensity: bitter intensity 1 minute after tasting the sample

TABLE 79

Means table of Sweetness and Bitterness Perception
for CC-00436, & 5% Sucrose at 4° C.

| | Sweetness | | | Bitterness | | |
|---|---|---|---|---|---|---|
| Sample | In Mouth | Overall Max | Linger (~60 sec) | In Mouth | Overall Max | Linger (~60 sec) |
| Reference: 5% Sucrose | 4.3 ± 2.1 | 4.5 ± 1.9 | 1.6 ± 1.8 | 0.15 ± 0.2 | 0.3 ± 0.3 | 0.1 ± 0.1 |
| CC-00436 0.3 ± 0.3 | 5.2 ± 2.1 | 5.7 ± 2.1 | 2.9 ± 2.5 | 1.5 ± 1.9 | 2.1 ± 1.7 | 0.7 ± 0.8 |

*Overall Maximum Sweetness and Bitterness includes Sweet and Bitter Intensity in Mouth scores if the attribute peaks while in mouth; Standard deviation

We claim:

1. A mogroside of Formula I, Formula II or Formula III:

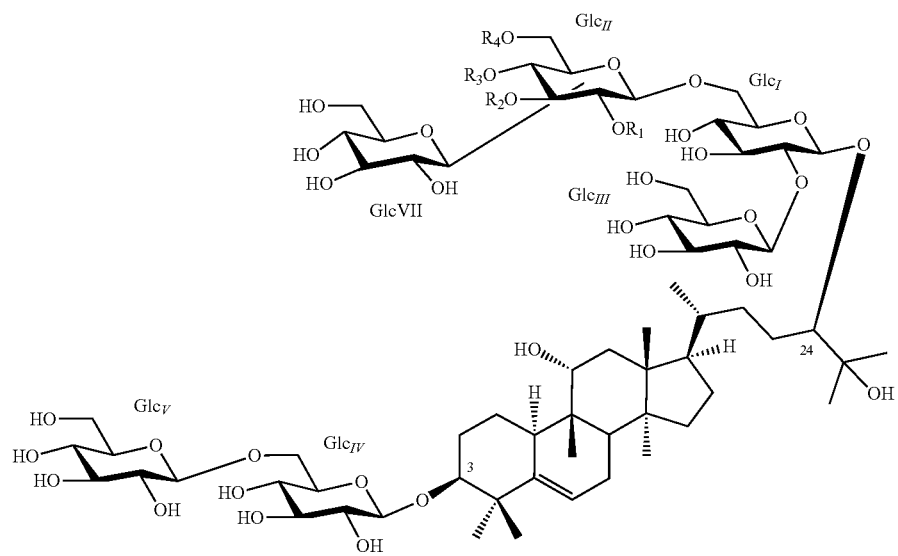

Formula I wherein GlcII and GlcVII are bonded at one of the $R_1$, $R_2$ or $R_3$ positions, and the other positions are hydrogen;

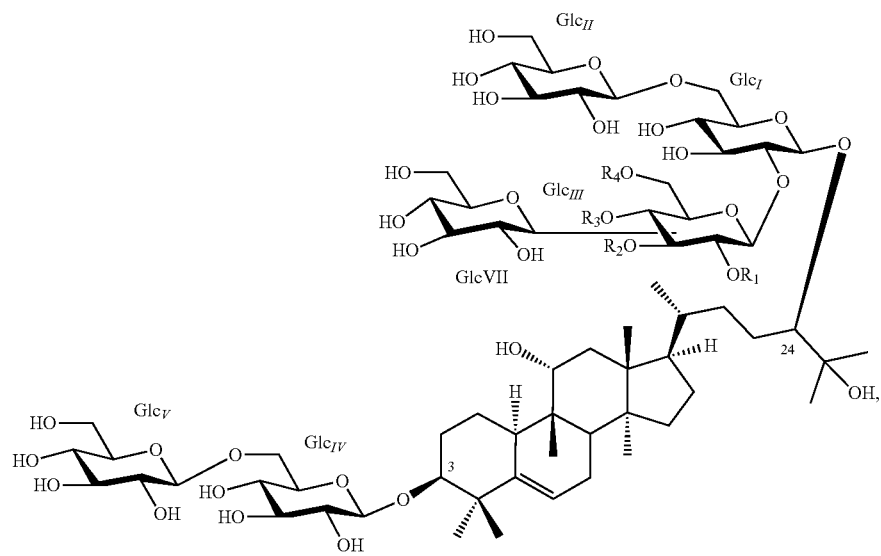

Formula II wherein GlcIII and GlcVII are bonded at one of the $R_2$, $R_3$ or $R_4$ positions, and the other positions are hydrogen; and

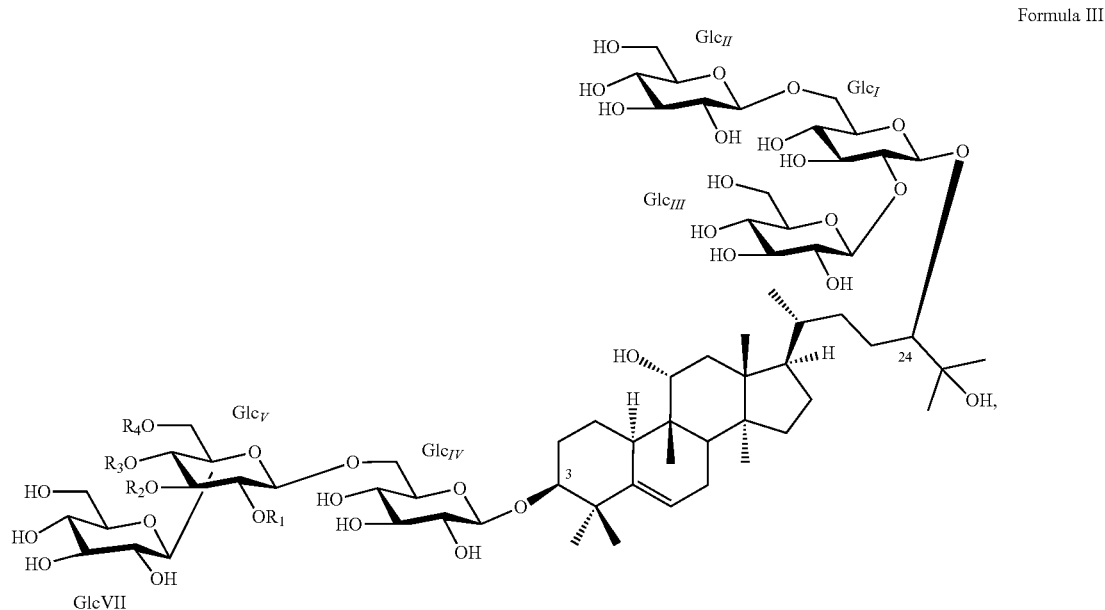

Formula III wherein GlcV and GlcVII are bonded at one of the $R_1$, $R_2$ or $R_3$ positions, and the other positions are hydrogen.

2. A mogroside of Formula IV or Formula V:

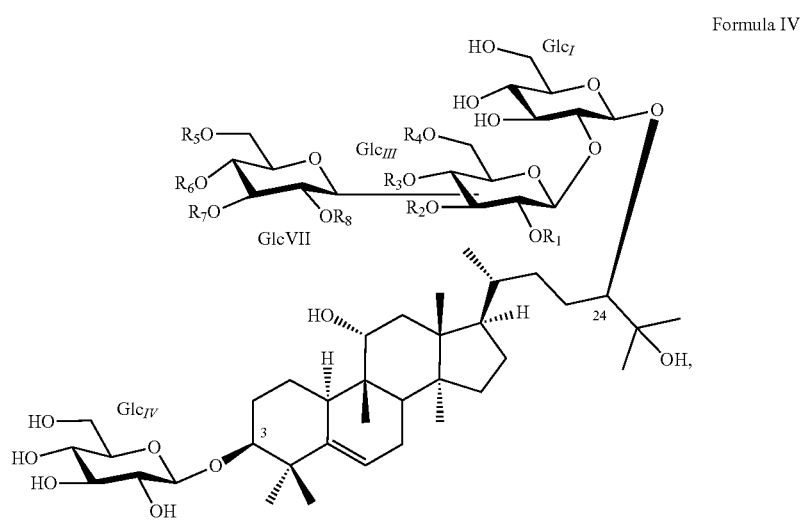

Formula IV wherein GlcIII and GlcVII are bonded at one of the $R_1$ or $R_4$ positions, and the other positions are hydrogen; and wherein $R_5$, $R_6$, $R_7$ and $R_8$ are each independently selected from hydrogen and glucose;

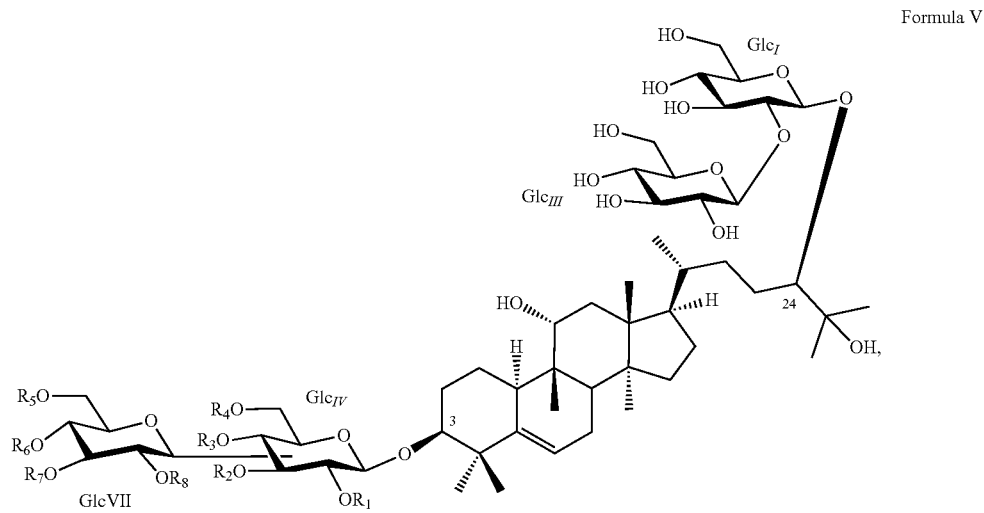

Formula V wherein GlcIV and GlcVII are bonded at the $R_1$ position, and the other positions are hydrogen; and wherein $R_5$, $R_6$, $R_7$ and $R_8$ are each independently selected from hydrogen and glucose.

3. A mogroside of Formula VI, Formula VII or Formula VIII:

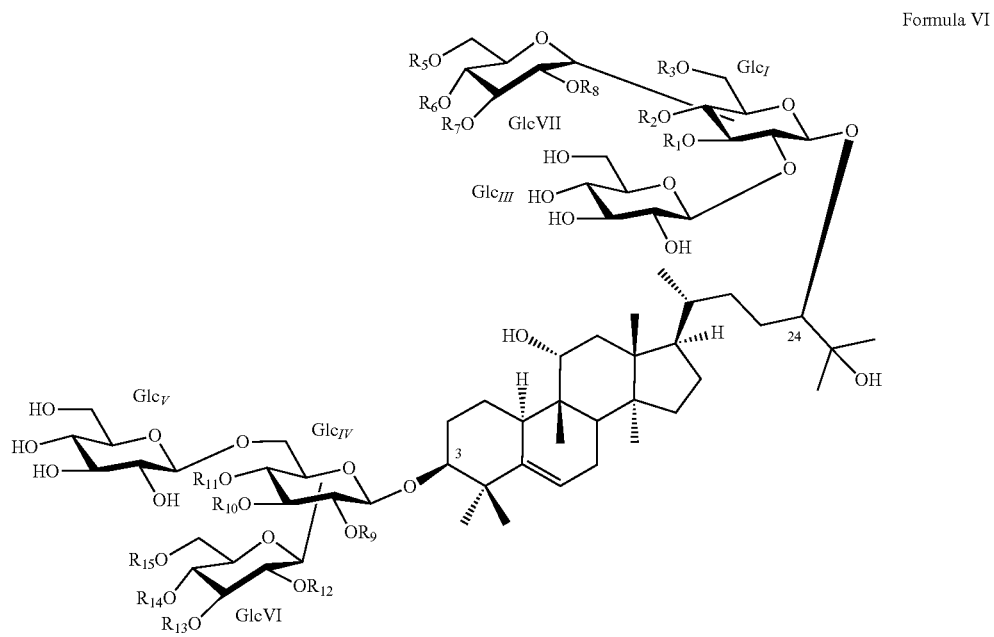

Formula VI wherein GlcI and GlcVII are bonded at one of the $R_1$ or $R_2$ positions and the other positions are hydrogen; GlcIV and GlcVI are bonded at one of the $R_{10}$ or $R_{11}$ positions and the other positions are hydrogen; and $R_5$, $R_6$, $R_7$, $R_8$, $R_9$, $R_{12}$, $R_{13}$, $R_{14}$ and $R_{15}$ are each independently selected from hydrogen and glucose;

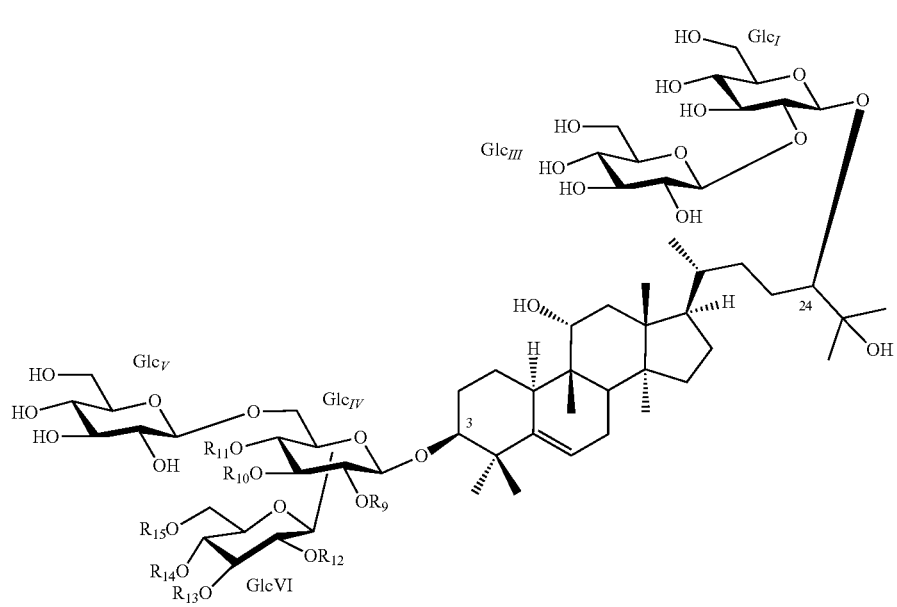

Formula VII wherein GlcIV and GlcVI are bonded at one of the $R_{10}$ or $R_{11}$ positions and the other positions are hydrogen; and $R_{12}$, $R_{13}$, $R_{14}$ and $R_{15}$ are each independently selected from hydrogen and glucose;

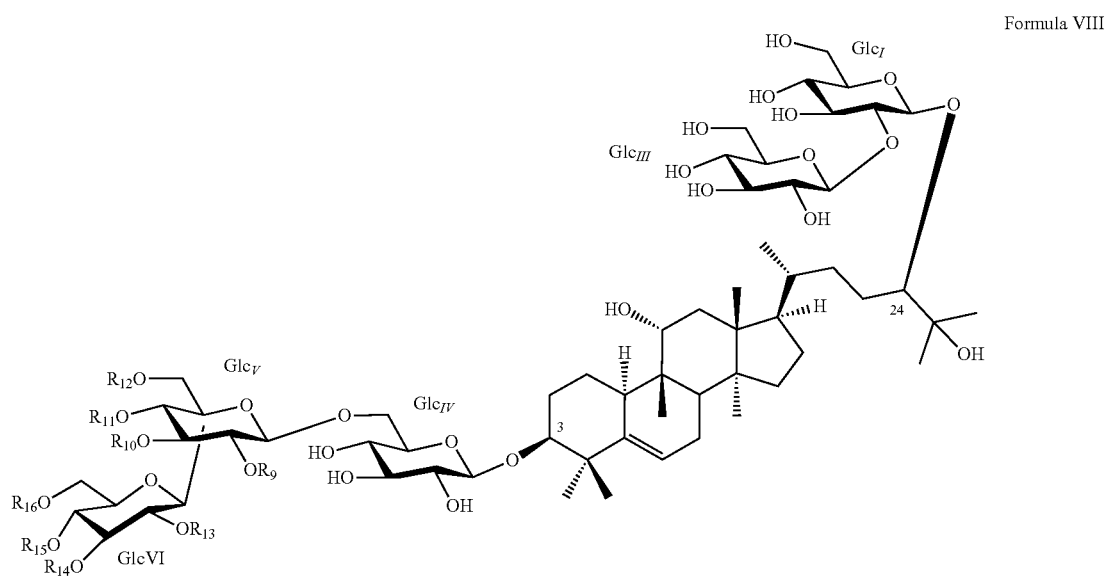

Formula VIII wherein GlcV and GlcVI are bonded at one of the $R_9$, $R_{10}$ or $R_{11}$ positions and the other positions are hydrogen; and $R_{13}$, $R_{14}$, $R_{15}$ and $R_{16}$ are each independently selected from hydrogen and glucose.

4. The mogroside of claim 1, wherein the mogroside is selected from the group consisting of CC-00403, CC-00367, CC-00371, CC-00401, CC-00436, and CC-00458.

5. The mogroside of claim 2, wherein the mogroside is isolated and purified.

6. A composition comprising a mogroside of claim 1.

7. The composition of claim 6, wherein the composition is selected from a sweetener composition and a consumable.

8. The composition of claim 7, wherein the consumable is a beverage or beverage product.

9. A method for preparing a target mogroside of claim 1 comprising contacting a medium comprising a starting mogroside selected from Mogroside V with a biocatalyst and co-substrate, thereby producing a composition comprising the target mogroside.

10. The method of claim 9, wherein the co-substrate is selected from the group consisting of sucrose, glucose-1-phosphate, α-D-glucose-1-fluoride, dextrin, starch and UDP-glucose.

11. The method of claim 10, wherein the starting mogroside is Mogroside V, the target mogroside is CC-00371, the biocatalyst is a Beta-galactosidase or variant thereof and the co-substrate is α-D-glucose-1-fluoride.

12. The method of claim 10, wherein the starting mogroside is Mogroside V, the target mogroside is CC-00367, the biocatalyst is a Beta-galactosidase or variant thereof and the co-substrate is α-D-glucose-1-fluoride.

13. The method of claim 10, wherein the starting mogroside is Mogroside V, the target mogroside is CC-00458, the biocatalyst is a UDP-glycosyltransferase (UGT) and the co-substrate is UDP-glucose.

14. The method of claim 9, wherein the medium further comprises a sucrose synthase and sucrose to catalytically recycle UDP.

15. The method of claim 10, further comprising separating the target mogroside from the medium to provide a separated target mogroside composition.

16. The method of claim 15, further comprising purifying the separated target mogroside composition to provide a purified target mogroside composition.

17. The method of claim 16, wherein the target mogroside is present in a purity of about 80% or greater by weight.

18. A beverage comprising a mogroside of Formula I, Formula II or Formula III:

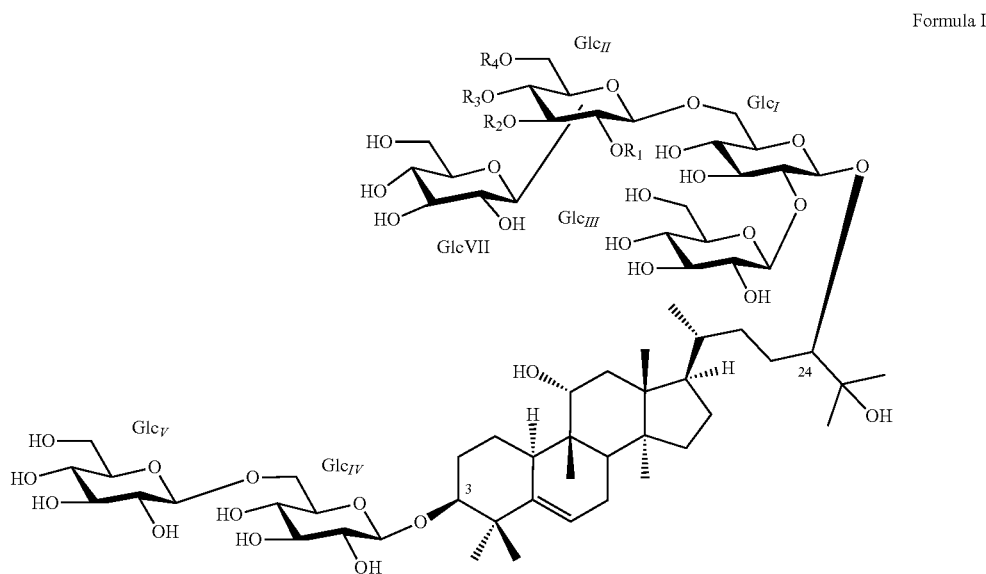

Formula I wherein GlcI and GlcVII are bonded at one of the $R_1$, $R_2$ or $R_3$ positions, and the other positions are hydrogen;

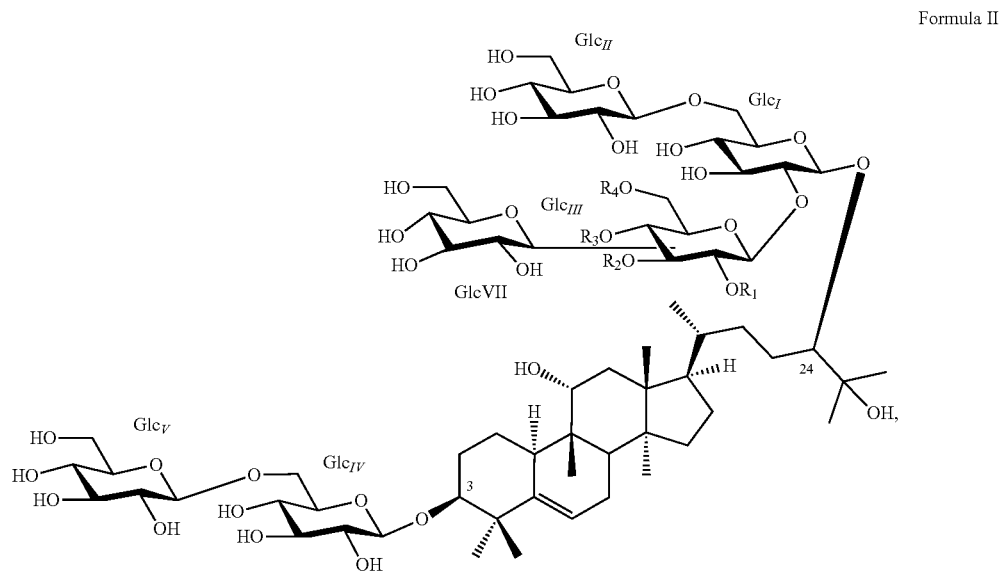

Formula II wherein GlcIII and GlcVII are bonded at one of the $R_2$, $R_3$ or $R_4$ positions, and the other positions are hydrogen; and

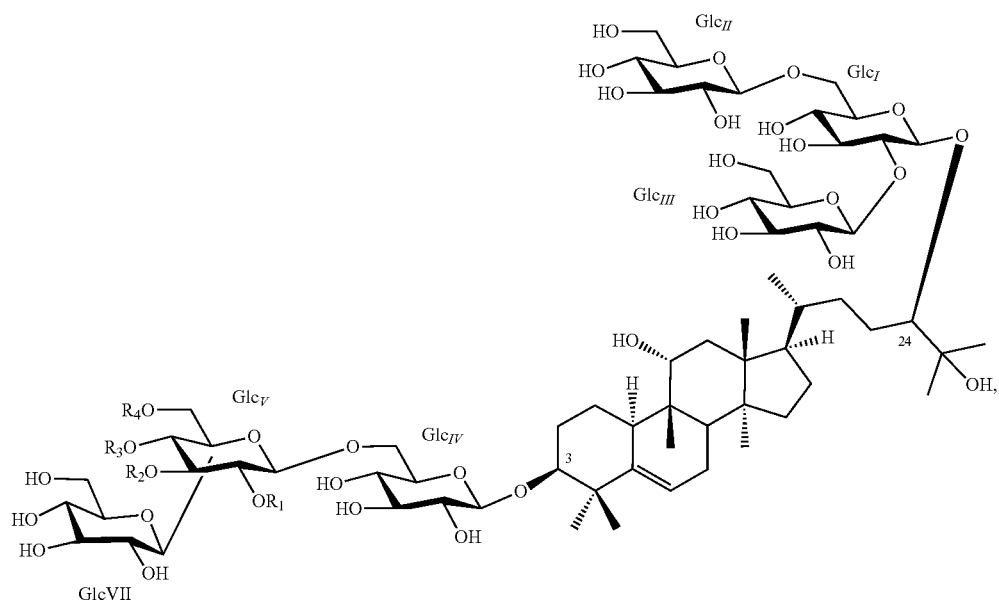

Formula III wherein GlcV and GlcVII are bonded at one of the $R_1$, $R_2$ or $R_3$ positions, and the other positions are hydrogen.

19. The beverage of claim 18, wherein the mogroside is present in the beverage in a concentration at or above its sweetness threshold concentration.

20. The beverage of claim 18, wherein the mogroside is present in the beverage in a concentration from about 25 ppm to about 600 ppm.

* * * * *